US011332528B2

(12) United States Patent
Eun et al.

(10) Patent No.: US 11,332,528 B2
(45) Date of Patent: May 17, 2022

(54) ANTI-CEACAM1 ANTIBODY AND USE THEREOF

(71) Applicants: MOGAM INSTITUTE FOR BIOMEDICAL RESEARCH, Yongin-si (KR); GREEN CROSS CORPORATION, Yongin-si (KR)

(72) Inventors: So-Young Eun, Yongin-si (KR); Miyoung Oh, Yongin-si (KR); Hye-Young Park, Yongin-si (KR); Mijung Lee, Yongin-si (KR); Aerin Yoon, Yongin-si (KR); Hye In Yum, Yongin-si (KR); Hyemi Nam, Yongin-si (KR); Eunhee Lee, Yongin-si (KR); Jongwha Won, Yongin-si (KR)

(73) Assignees: MOGAM INSTITUTE FOR BIOMEDICAL RESEARCH, Yongin-si (KR); GREEN CROSS CORPORATION, Yongin (KR)

( * ) Notice: Subject to any disclaimer, the term of this patent is extended or adjusted under 35 U.S.C. 154(b) by 160 days.

(21) Appl. No.: 16/496,777

(22) PCT Filed: Mar. 23, 2018

(86) PCT No.: PCT/KR2018/003419
§ 371 (c)(1),
(2) Date: Sep. 23, 2019

(87) PCT Pub. No.: WO2018/174629
PCT Pub. Date: Sep. 27, 2018

(65) Prior Publication Data
US 2020/0109196 A1    Apr. 9, 2020

(30) Foreign Application Priority Data

Mar. 24, 2017 (KR) .................. 10-2017-0037613
Nov. 30, 2017 (KR) .................. 10-2017-0162785

(51) Int. Cl.
C07K 16/28    (2006.01)
A61P 35/00    (2006.01)
A61K 35/17    (2015.01)
A61K 39/395   (2006.01)

(52) U.S. Cl.
CPC .......... *C07K 16/2803* (2013.01); *A61K 35/17* (2013.01); *A61K 39/3955* (2013.01); *A61P 35/00* (2018.01); *C07K 2317/33* (2013.01); *C07K 2317/565* (2013.01); *C07K 2317/73* (2013.01); *C07K 2317/92* (2013.01)

(58) Field of Classification Search
CPC ..... C07K 16/2803; A61P 35/00; A61K 35/17; A61K 39/3955
See application file for complete search history.

(56) References Cited

U.S. PATENT DOCUMENTS 9,512,220 B2    12/2016  Lee et al.
2014/0328841 A1 11/2014  Blumberg et al.
2016/0176966 A1  6/2016  Markel et al.
2017/0051058 A1  2/2017  Lang et al.

FOREIGN PATENT DOCUMENTS

WO    2013/054320 A1    4/2013
WO    2015166484 A1    11/2015

OTHER PUBLICATIONS

Lamminmaki et al. "Crystal structure of a recombinant anti-estradiol Fab fragment in complex with 17beta-estradiol", JBC 2001, 276:36687-36694 (Year: 2001).*
Rudikoff et al . "Single amino acid altering antigen-binding specificity", Proc Natl Acad Sci USA 1982 vol. 79 p. 1979 (Year: 1979).*
MacCallum et al. "Antibody-antigen Interactions: Contact Analysis and Binding Site Topography", J. Mol. Biol. (1996) 262, 732-745 (Year: 1996).*
Pascalis et al. "Grafting of "Abbreviated" Complementarity-Determining Regions Containing Specificity-Determining Residues Essential for Ligand Contact to Engineer a Less Immunogenic Humanized Monoclonal Antibody", The Journal of Immunology (2002) 169, 3076-3084 (Year: 2002).*
Casset et al. "A peptide mimetic of an anti-CD4 monoclonal antibody by rational design", BBRC 2003, 307:198-205 (Year: 2003).*
Vajdos et al. "Comprehensive functional maps of the antigen-binding site of an anti-ErbB2 antibody obtained with shotgun scanning mutagenesis", J. Mol. Biol. (2002) 320, 415-428 (Year: 2002).*
Chen et al. "Selection and analysis of an optimized anti-VEGF antibody: crystal structure of an affinity-matured Fab in complex with antigen", J. Mol. Bio. (1999) 293, 865-881 (Year: 1999).*
Wu et al. "Humanization of a murine monoclonal antibody by simultaneous optimization of framework and CDR residues", J. Mol. Biol. (1999) 294, 151-162 (Year: 1999).*
Padlan et al. "Structure of an antibody-antigen complex: crystal structure of the HyHEL-10 Fab-lysozyme complex", PNAS 1989, 86: 5938-5942 (Year: 1989).*
Dankner et al. "CEACAM1 as a multi-purpose target for cancer immunotherapy", OncoImmunology, 6:7, e1328336, DOI: 10.1080/2162402X.2017.1328336 (Year: 2017).*
International Search Report for PCT/KR2018/003419 dated Jul. 30, 2018 [PCT/ISA/210].
Written Opinion for PCT/KR2018/003419 dated Jul. 30, 2018 [PCT/ISA/237].

(Continued)

*Primary Examiner* — Chun W Dahle
*Assistant Examiner* — Peter Johansen
(74) *Attorney, Agent, or Firm* — Sughrue Mion, PLLC

(57) ABSTRACT

The present invention provides anti-CEACAM1 antibodies with improved binding abilities specific to CEACAM1, and a use thereof. Anti-CEACAM1 antibodies according to the present invention exhibit superior binding abilities specific to CEACAM1, and also activate the anti-cancer immune functions of cytotoxic T cells and natural killer cells, and thus, each one of them can be effectively used as an anti-cancer agent and a composition for treating cancer.

32 Claims, 26 Drawing Sheets

Specification includes a Sequence Listing.

(56) References Cited

OTHER PUBLICATIONS

R. Ortenberg et al., "Novel Immunotherapy for Malignant Melanoma with a Monoclonal Antibody That Blocks CEACAM1 Homophilic Interactions", Molecular Cancer Therapeutics, vol. 11, No. 6, Mar. 30, 2012, pp. 1300-1310 (11 p. total).

So-Young Eun, "Abstract 1645: CEACAM1-blockade for T-cell activation and antitumor T-cell Yesponse", Cancer Research, vol. 77, issue 13 supplement, Jul. 2017, 2 pages total.

* cited by examiner

[Fig. 1]
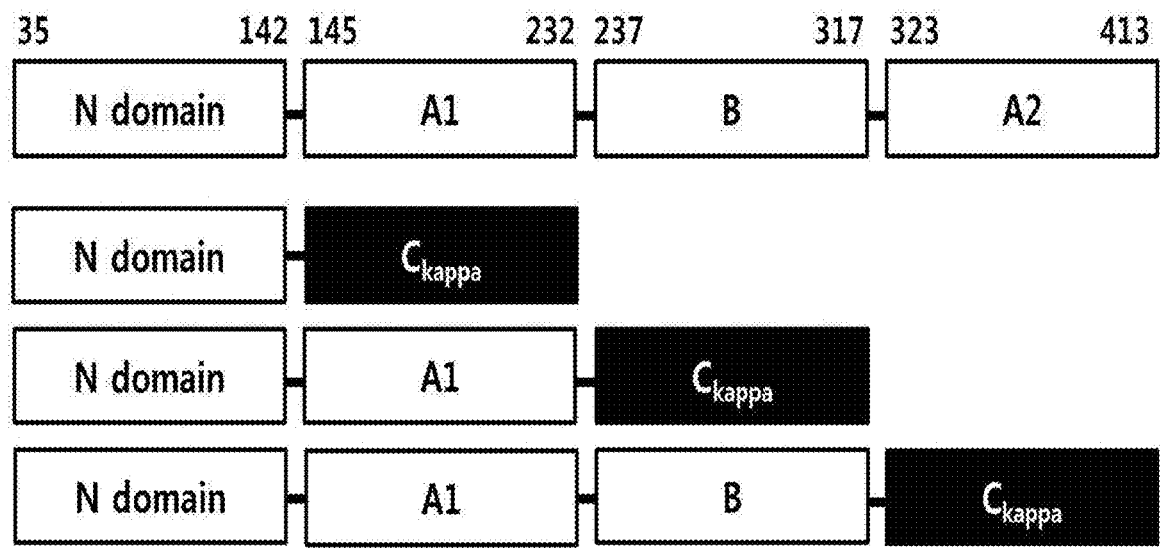
[Fig. 2]
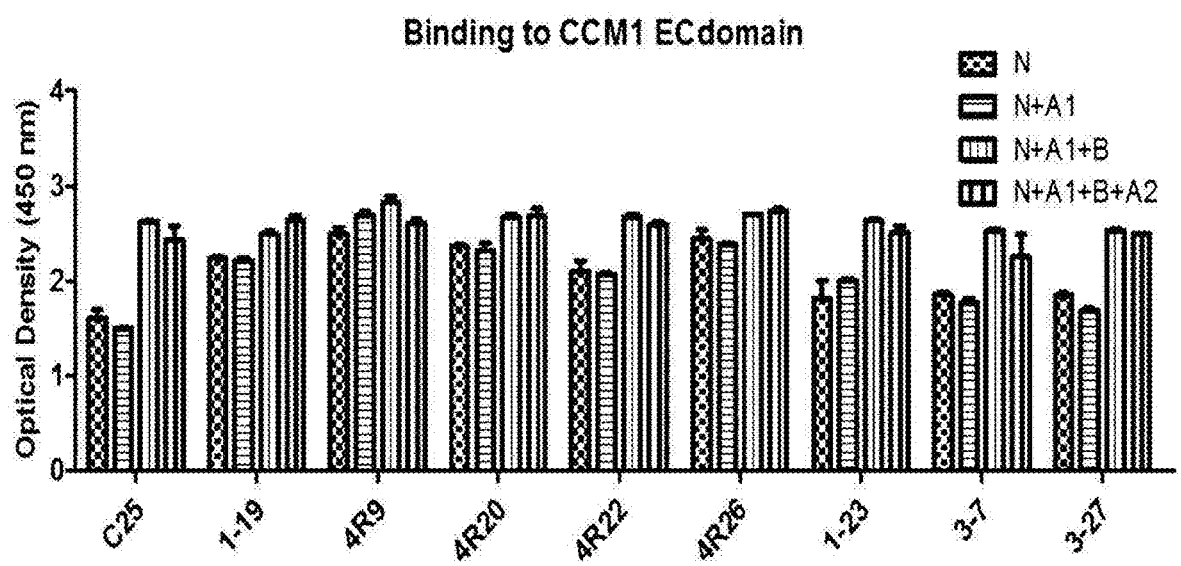

[Fig. 3]
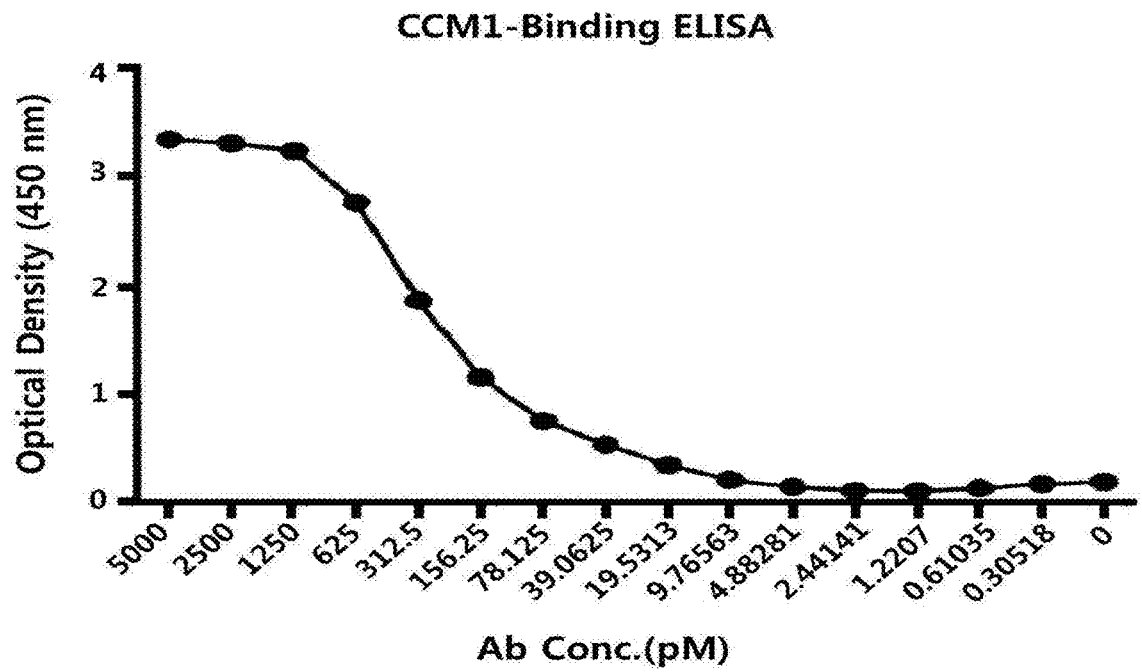
[Fig. 4]
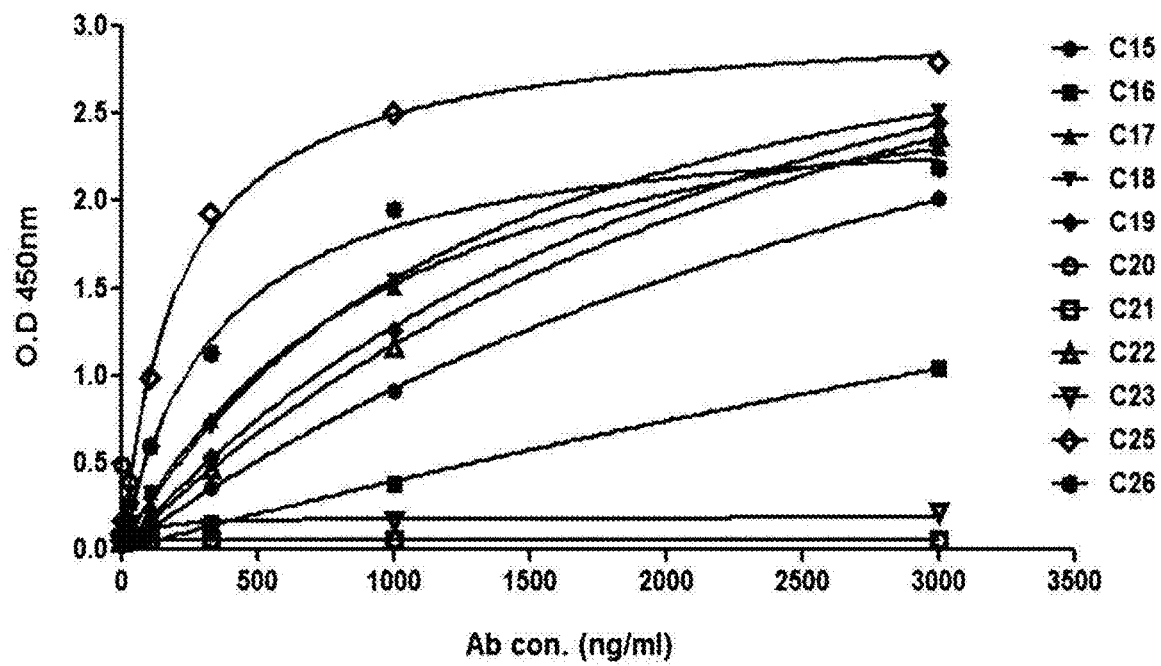

[Fig. 5(a)]
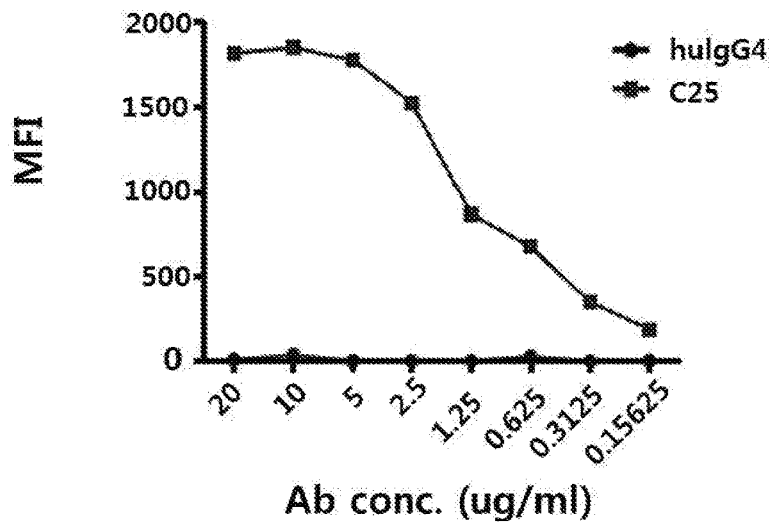
[Fig. 5(b)]
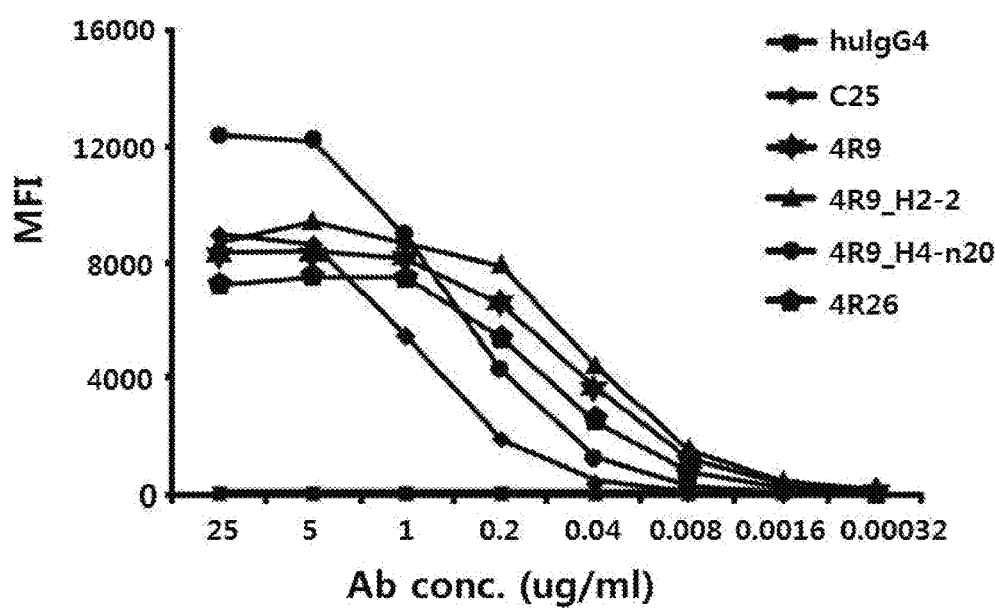

[Fig. 6]

| Clone | $K_D$ (M) | $k_{on}$ (1/Ms) | $K_{off}$ (1/s) |
|---|---|---|---|
| C25 | $3.49 \times 10^{-8}$ | $1.82 \times 10^4$ | $5.05 \times 10^{-4}$ |
| 4R9 | $3.39 \times 10^{-9}$ | $1.63 \times 10^5$ | $5.67 \times 10^{-4}$ |
| 4R26 | $1.82 \times 10^{-9}$ | $1.33 \times 10^5$ | $2.66 \times 10^{-4}$ |
| 4R9_H2-2 | $3.54 \times 10^{-9}$ | $1.69 \times 10^5$ | $6.27 \times 10^{-4}$ |
| 4R9_H4-n20 | $3.90 \times 10^{-9}$ | $2.61 \times 10^5$ | $3.33 \times 10^{-4}$ |
| 4R9_H4-n20HC +4R26LC | $2.57 \times 10^{-9}$ | $1.90 \times 10^5$ | $3.21 \times 10^{-4}$ |

[Fig. 7]
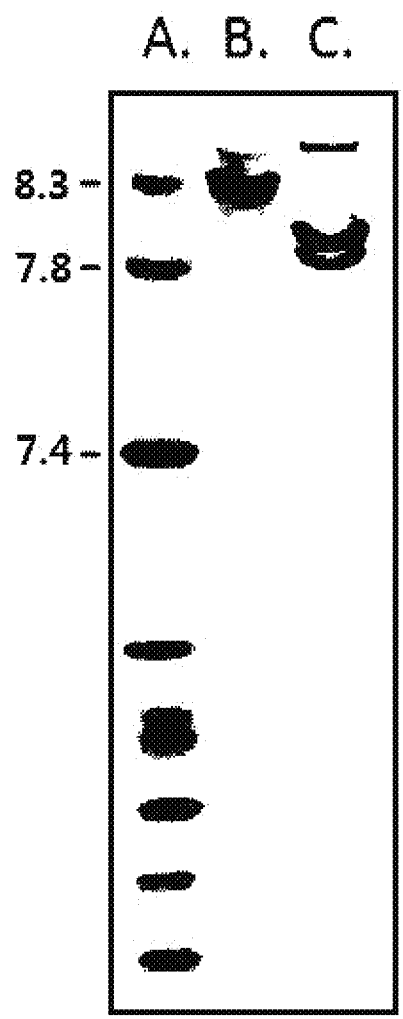

[Fig. 8]
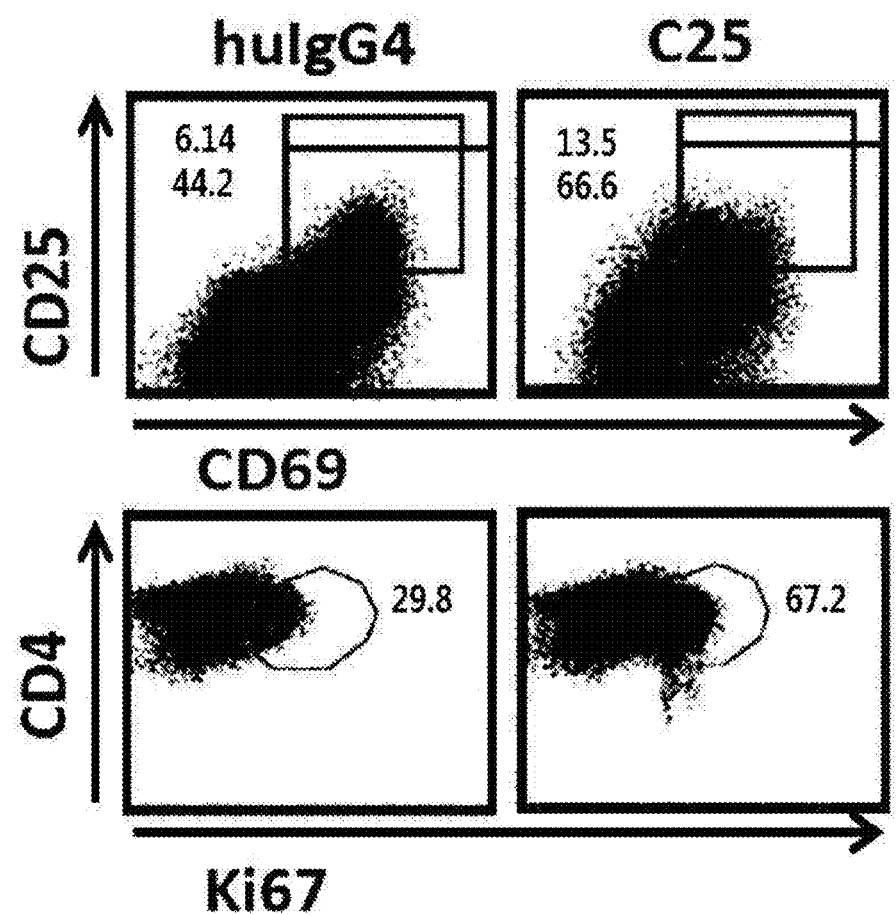

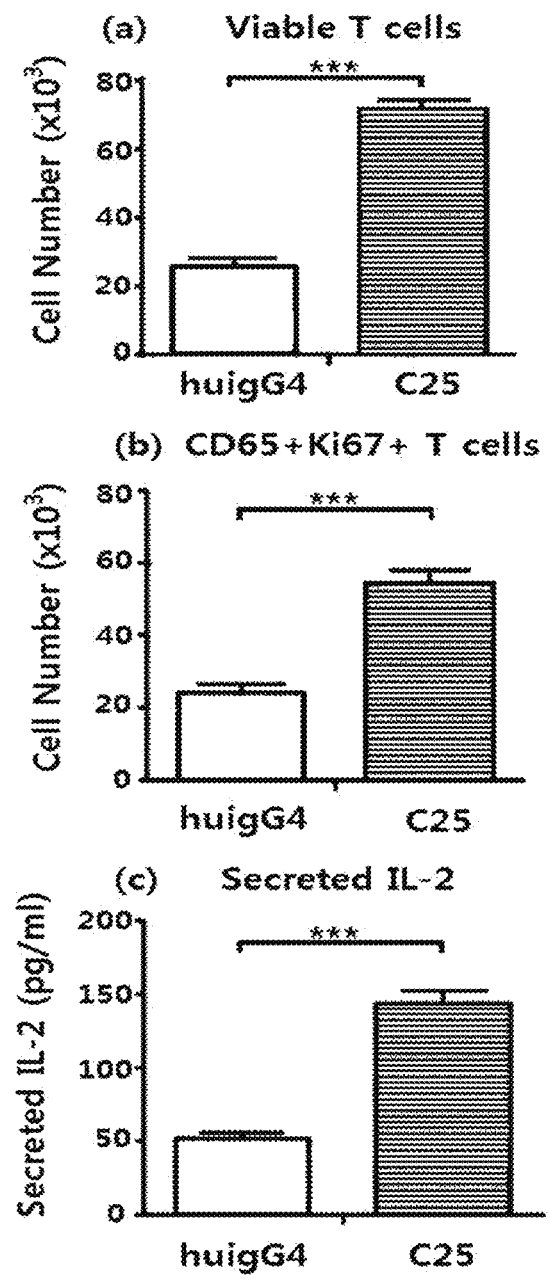
[Fig. 9]

[Fig. 10]
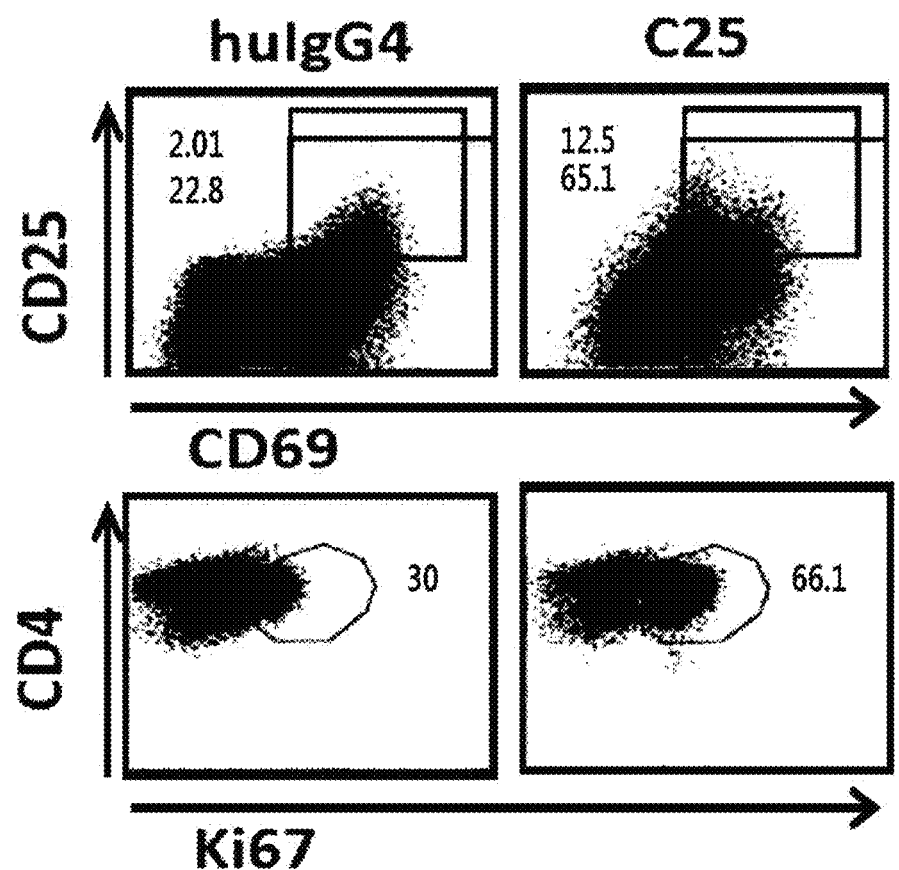

[Fig. 11]
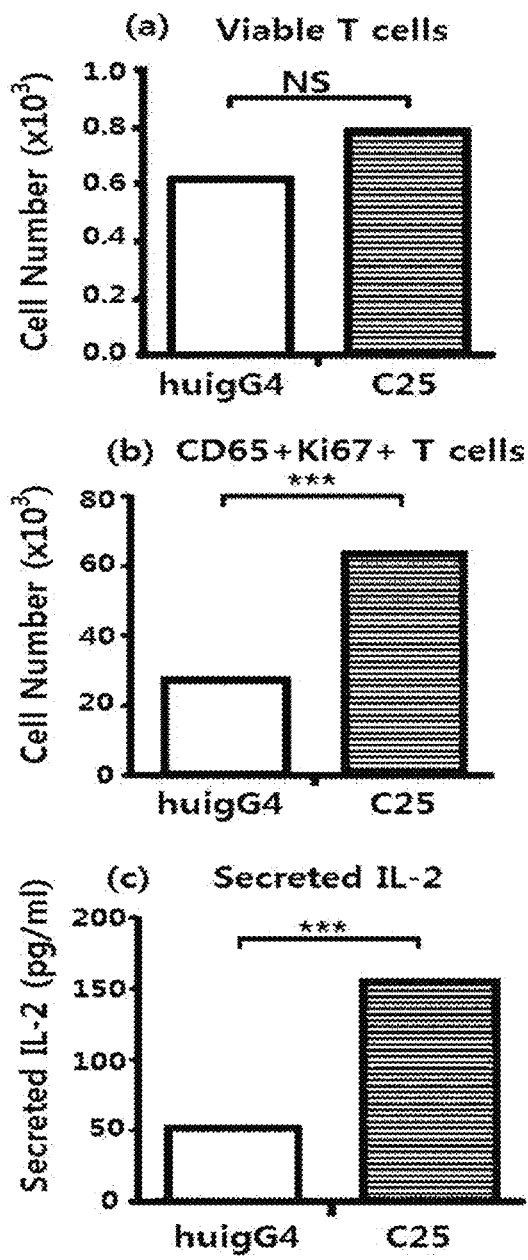

[Fig. 12]
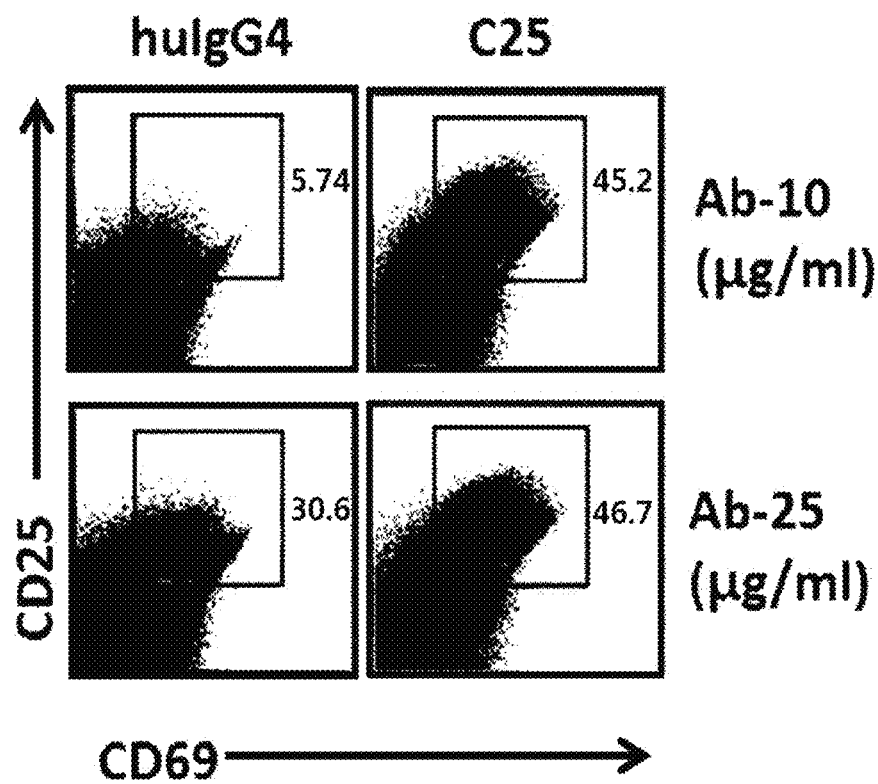

[Fig. 13]
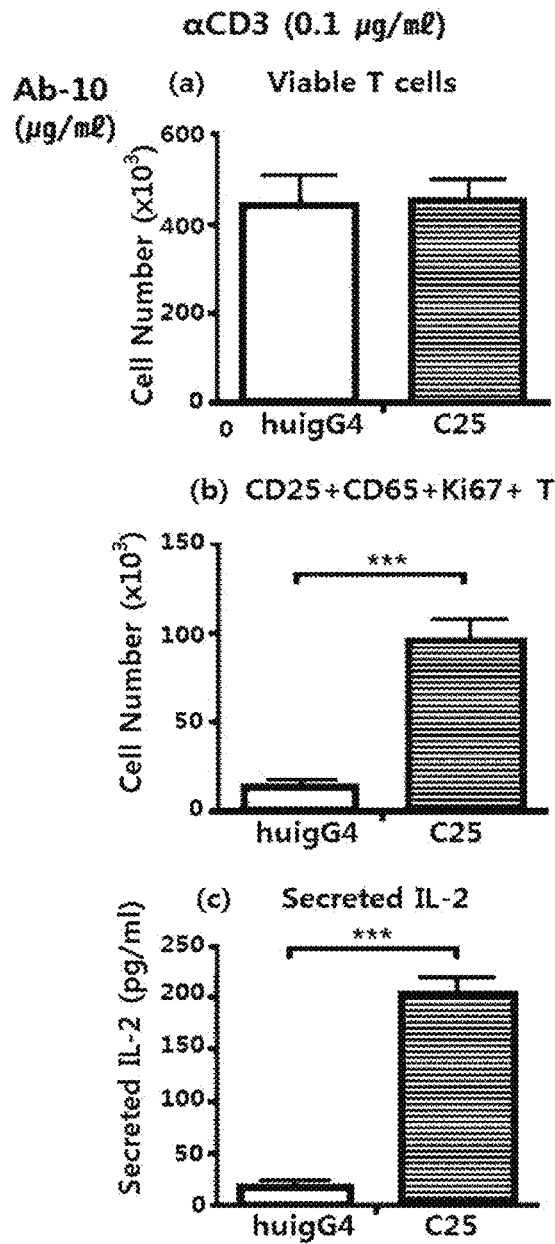

[Fig. 14]
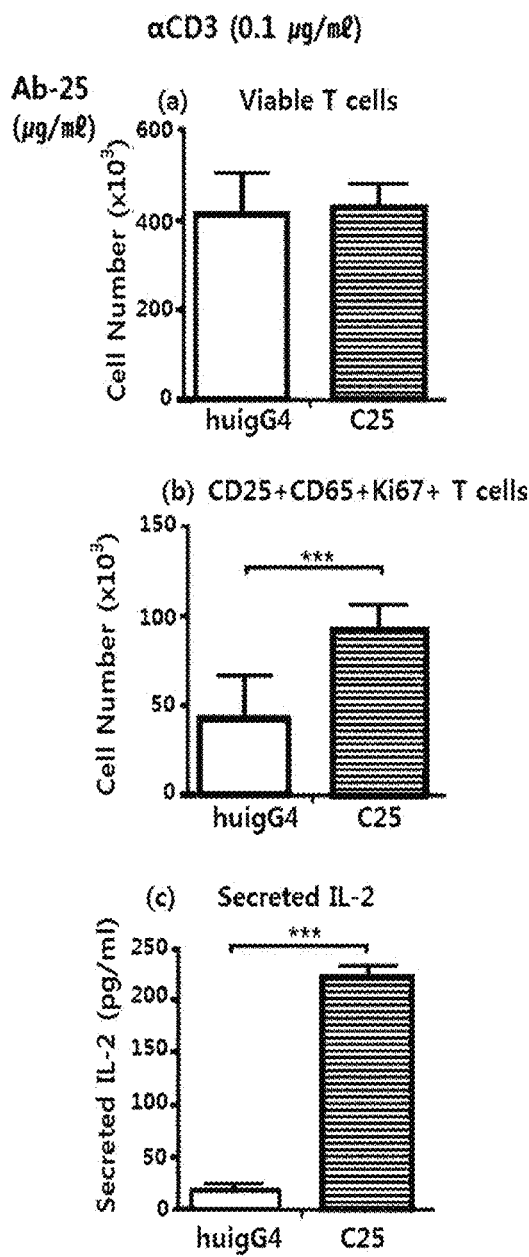

[Fig. 15]
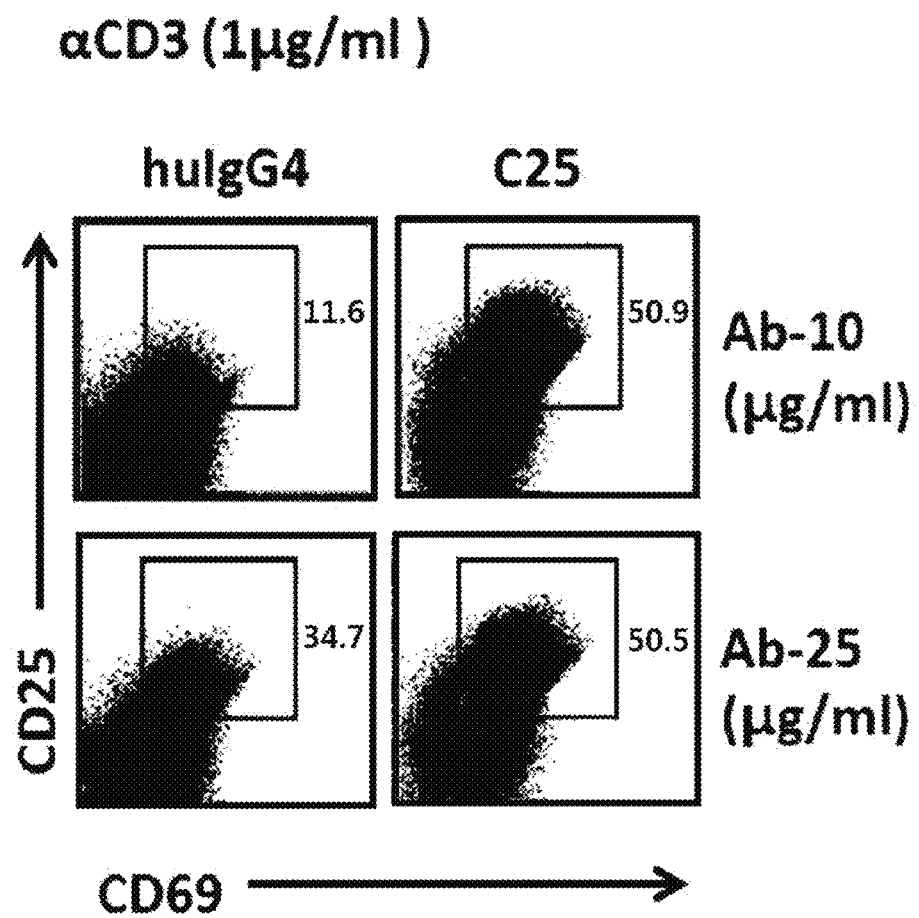

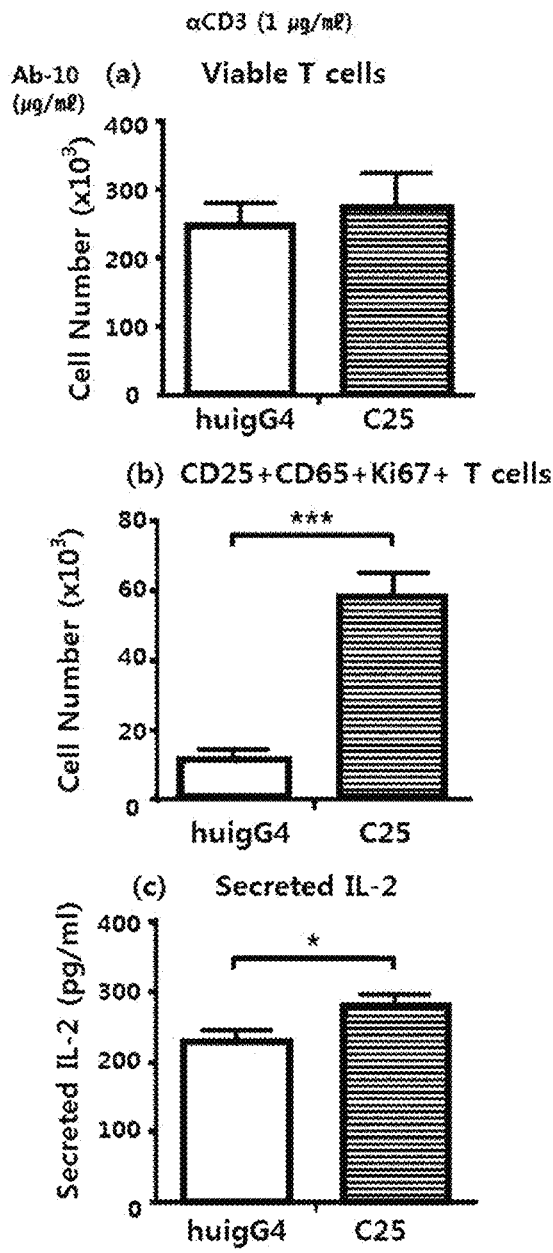
[Fig. 16]

[Fig. 17]
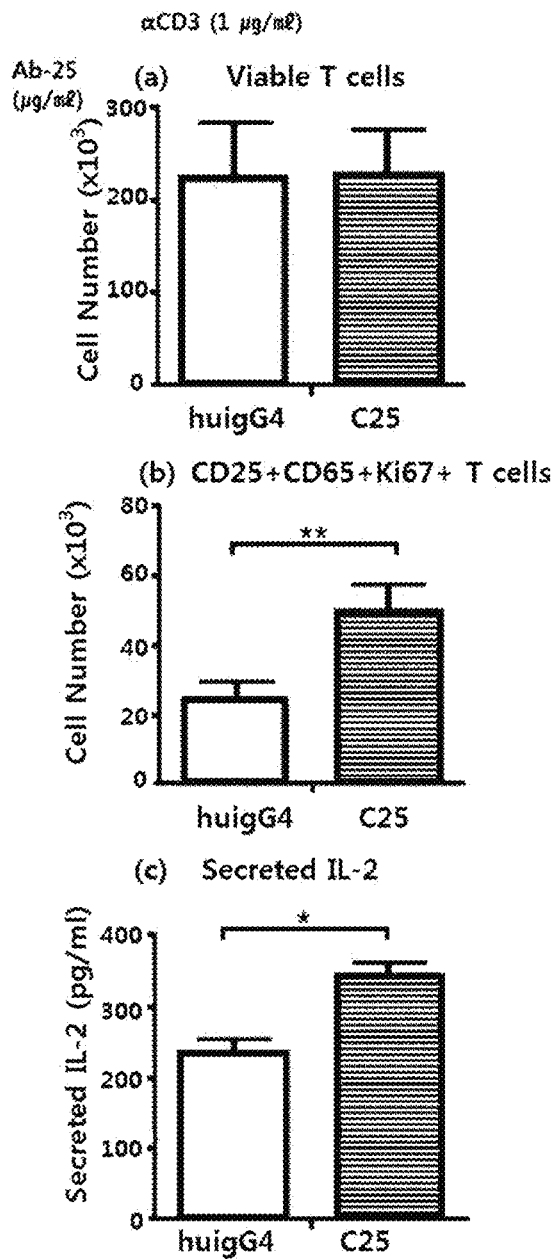

[Fig. 18]
(a) Jurkat-GFP/NFAT-Luc
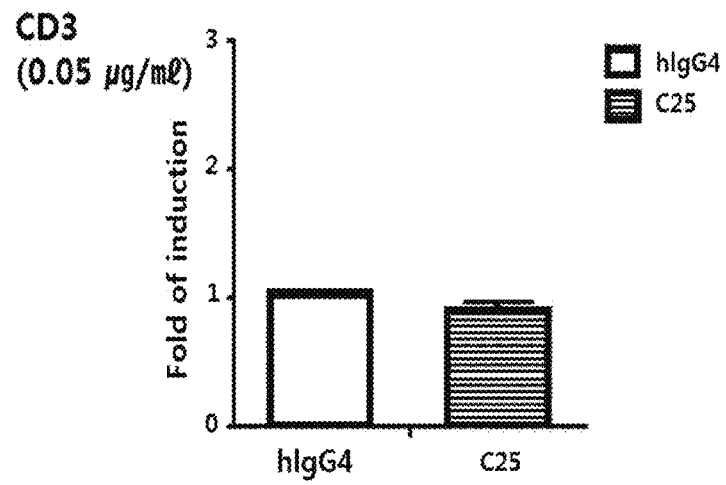
(b) Jurkat-CAECAM1-GFP/NFAT-Luc
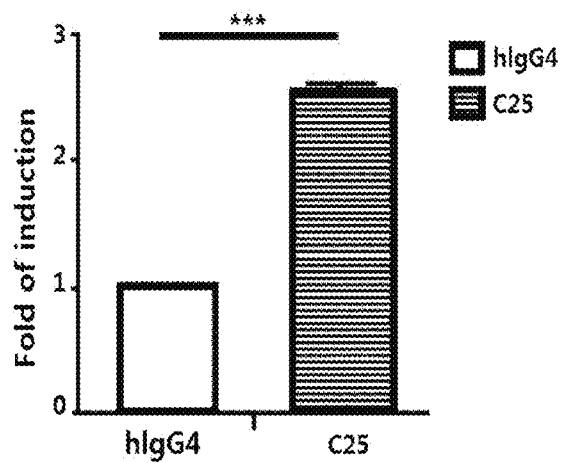

[Fig. 19]
(a) Jurkat-GFP/NFAT-Luc
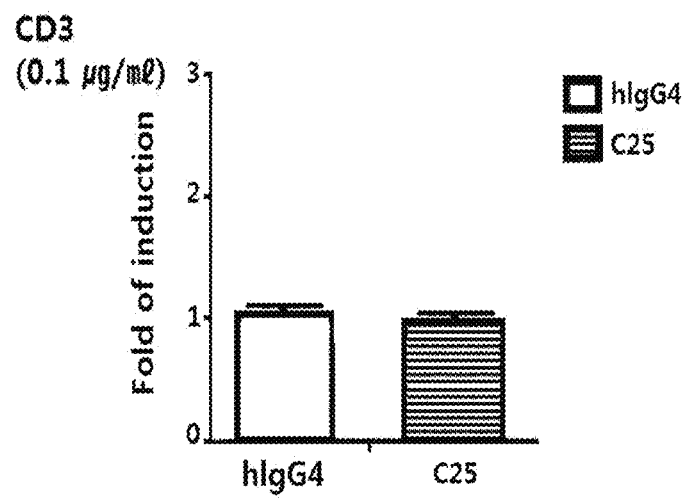
(b) Jurkat-CAECAM1-GFP/NFAT-Luc
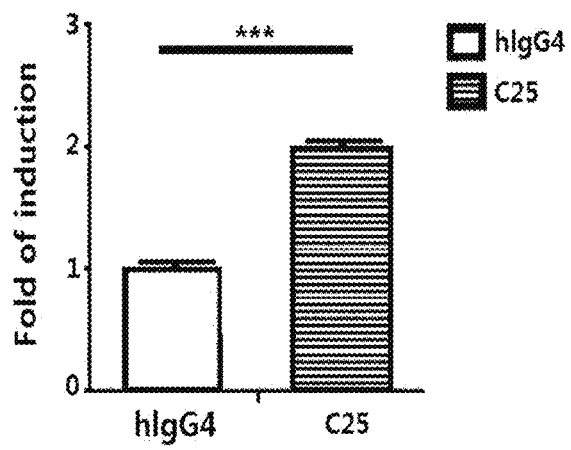

[Fig. 20]
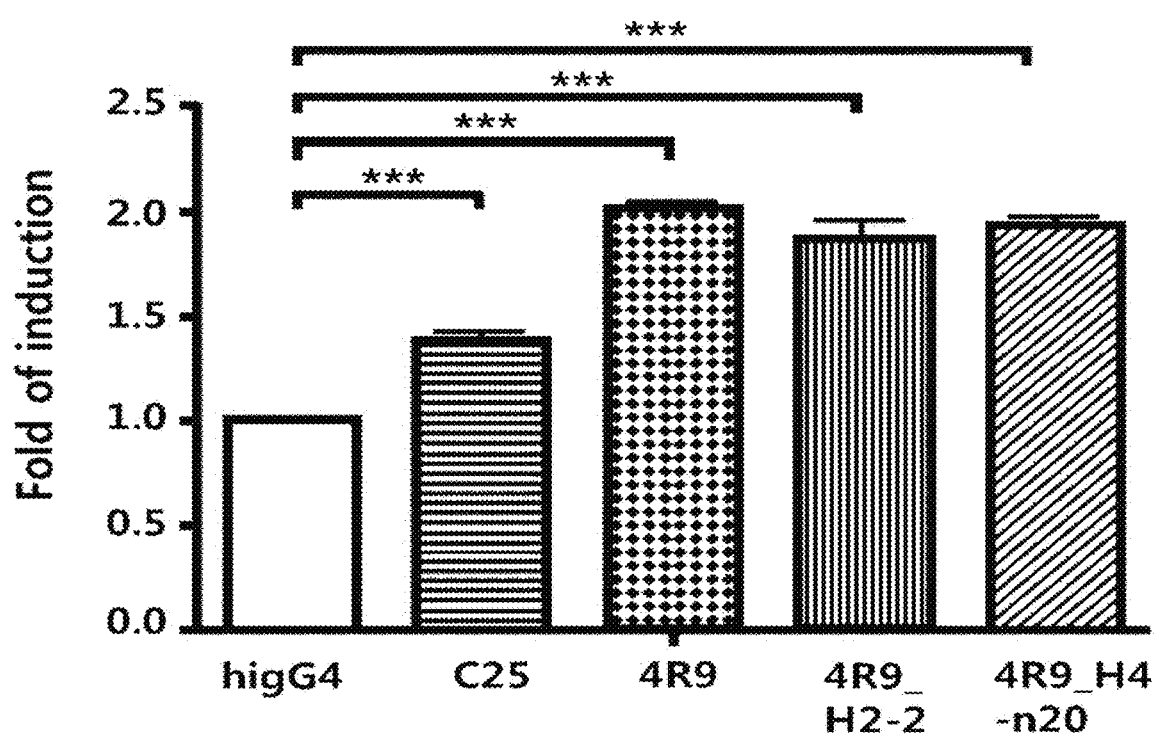

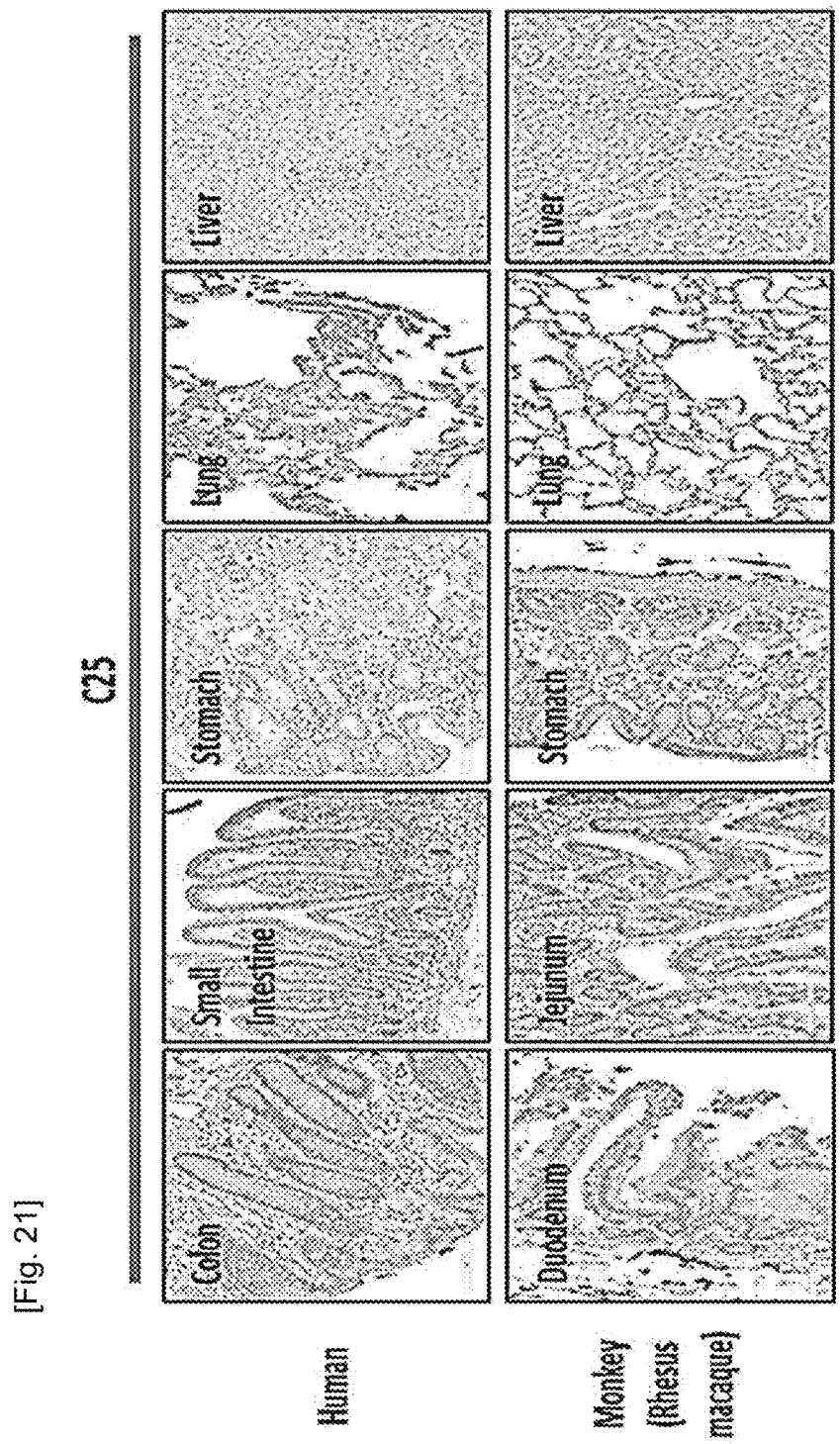
[Fig. 21]

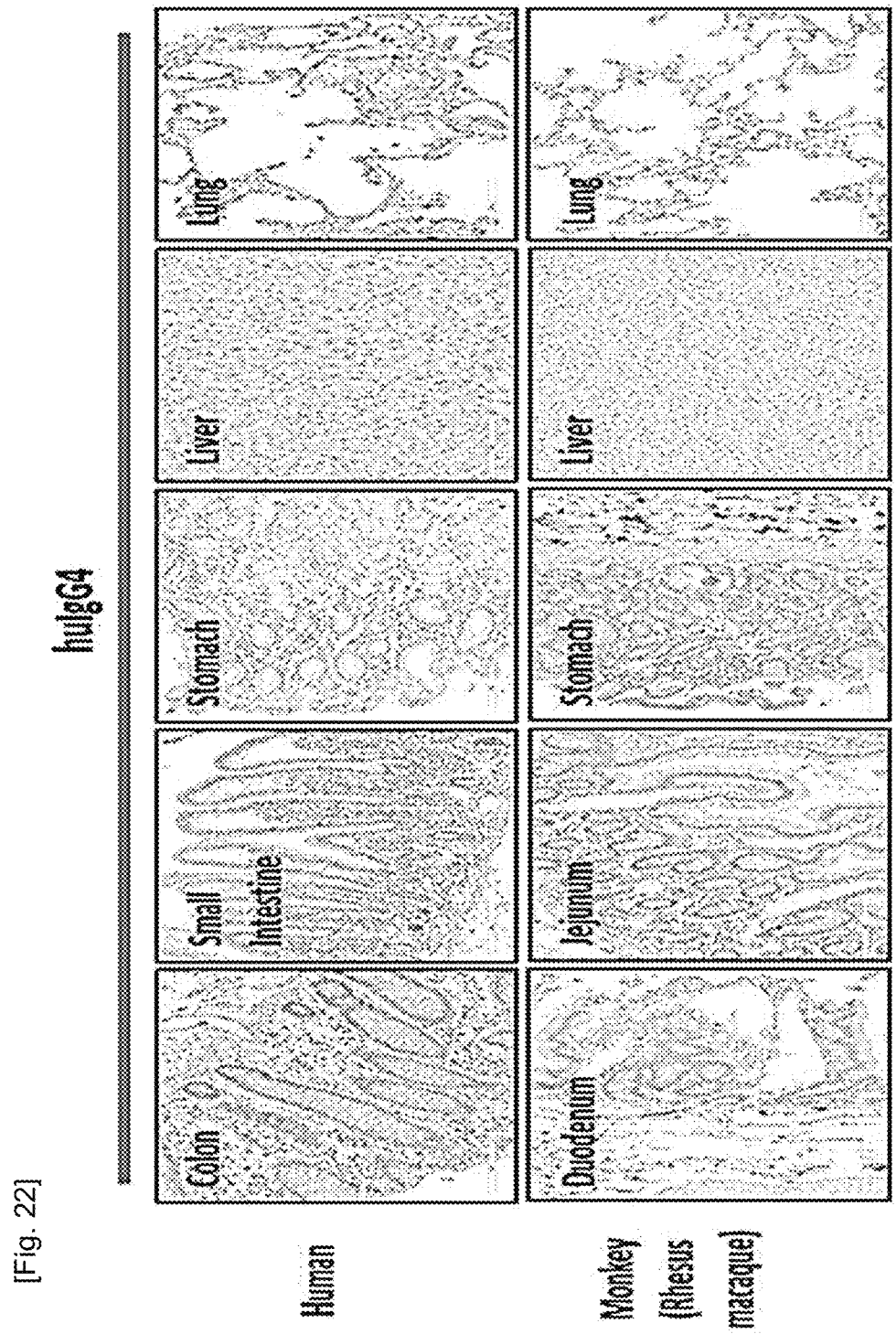
[Fig. 22]

[Fig. 23]
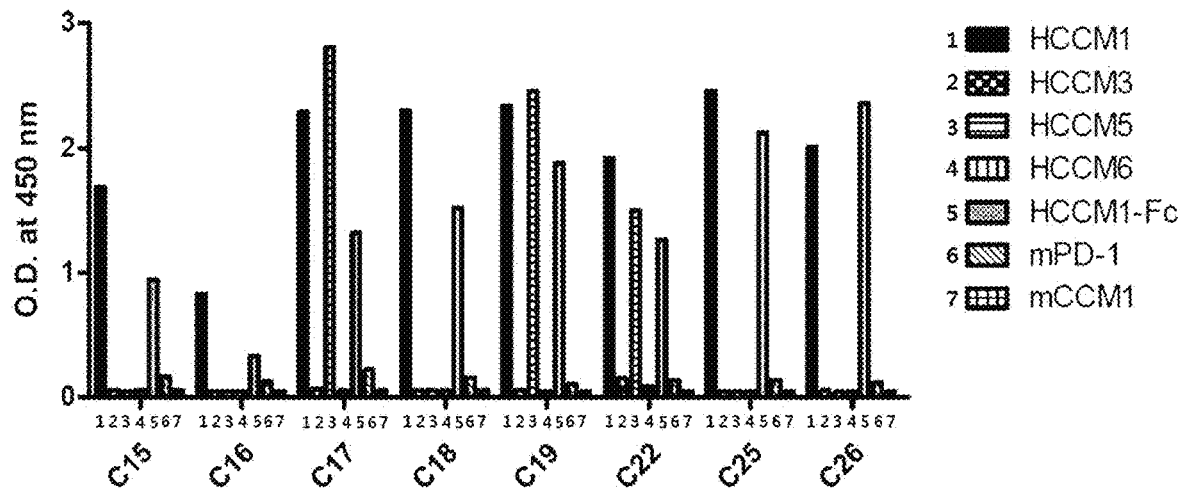
[Fig. 24]
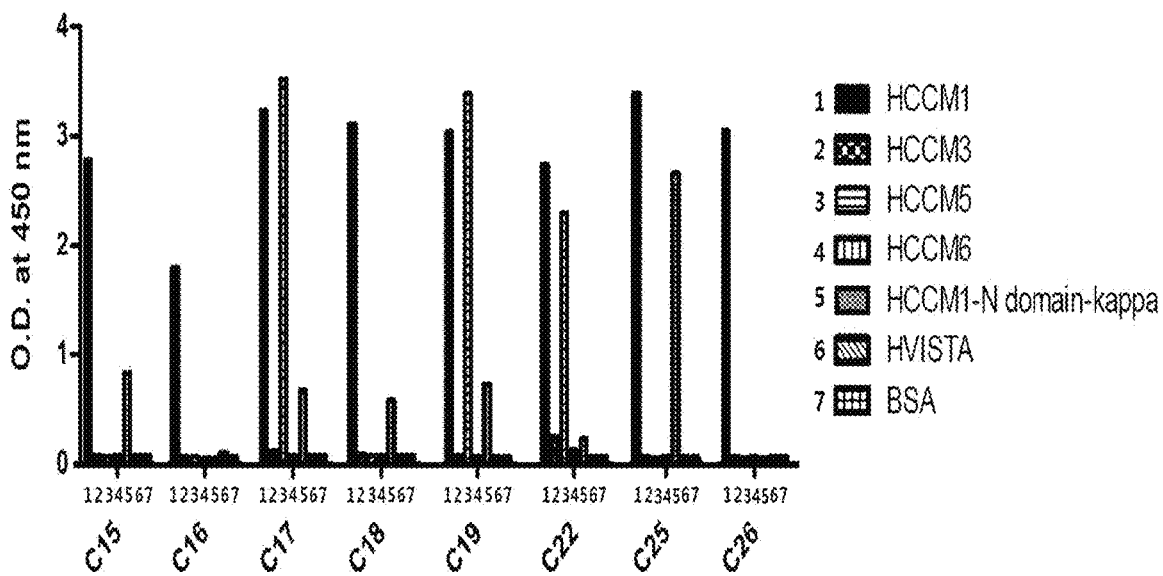

[Fig. 25]
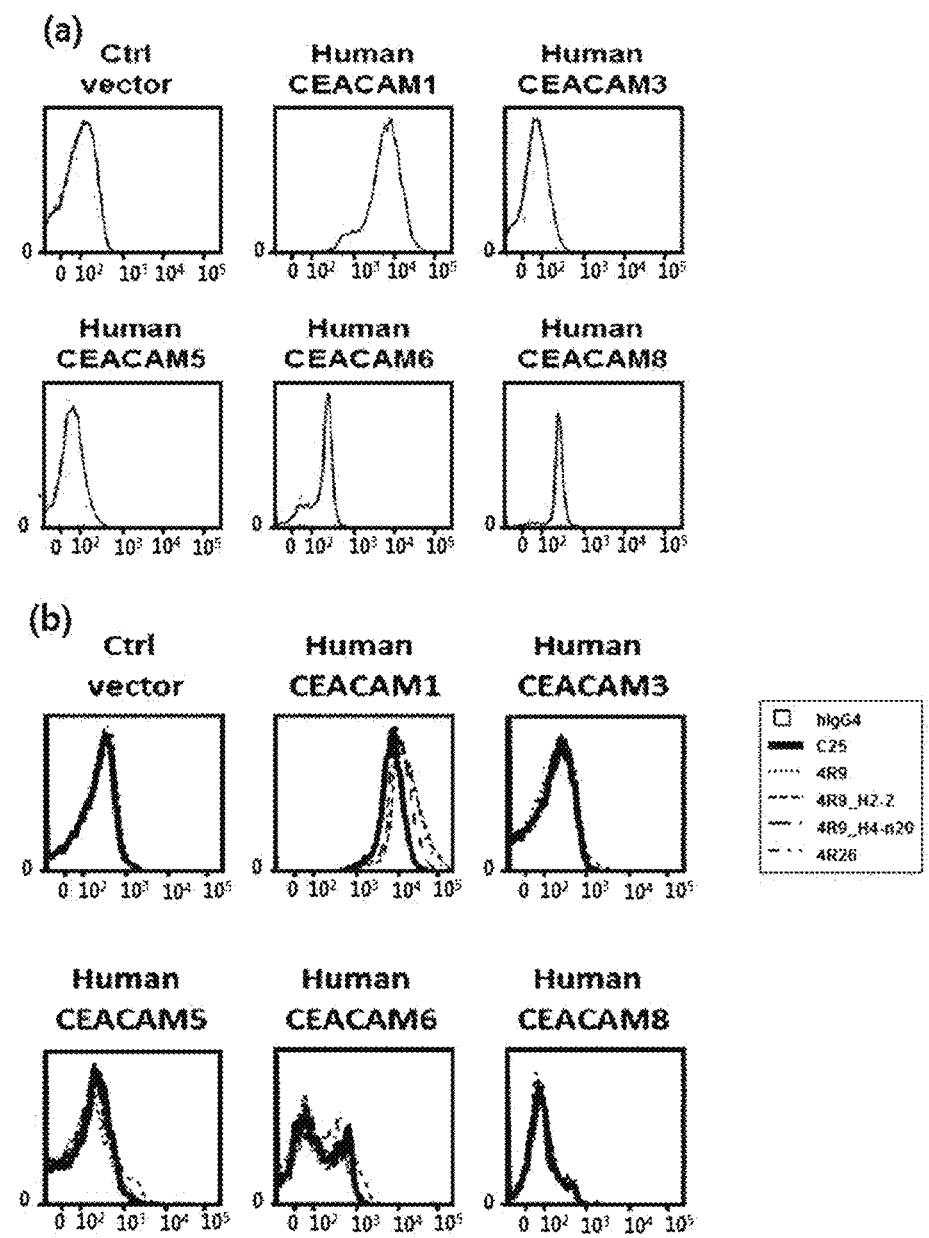

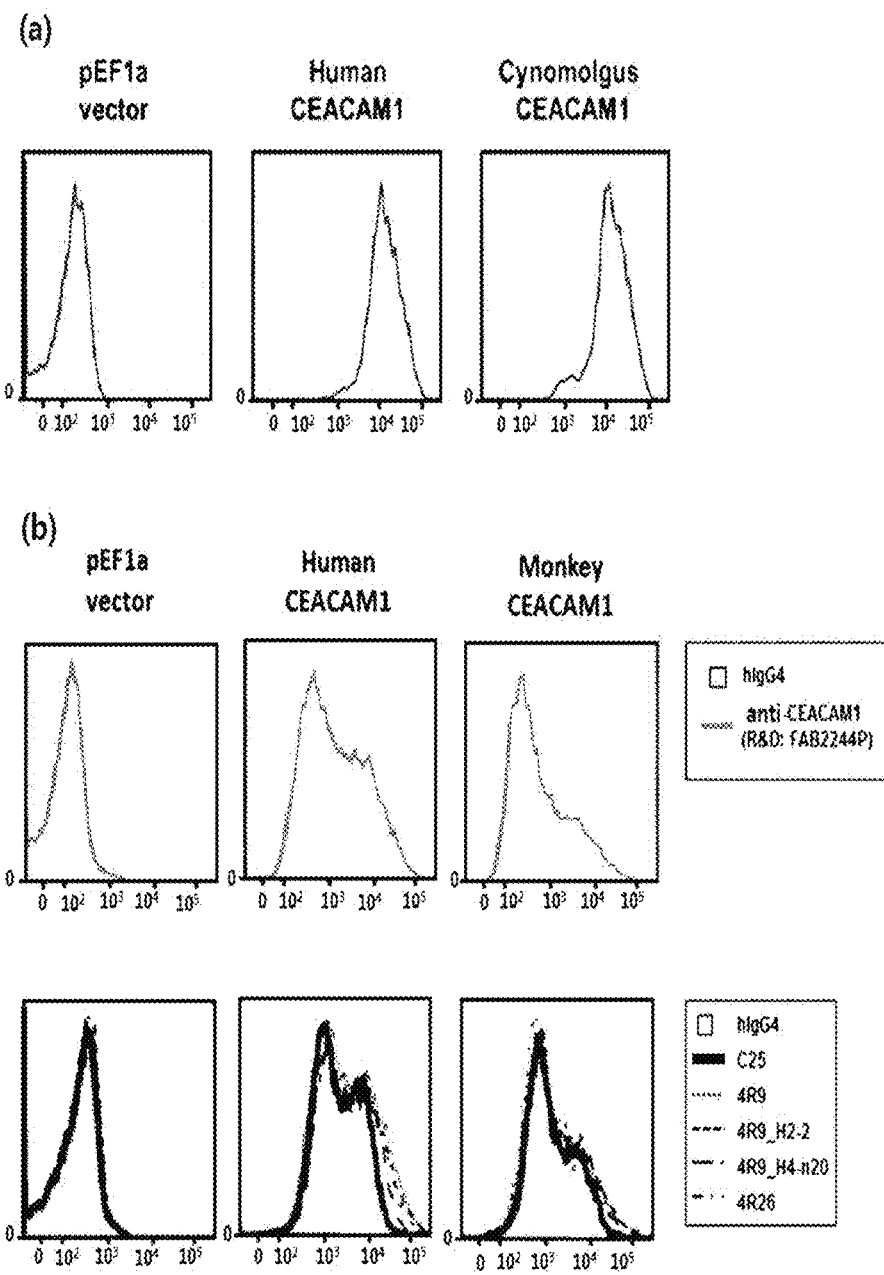
[Fig. 26]

[Fig. 27]
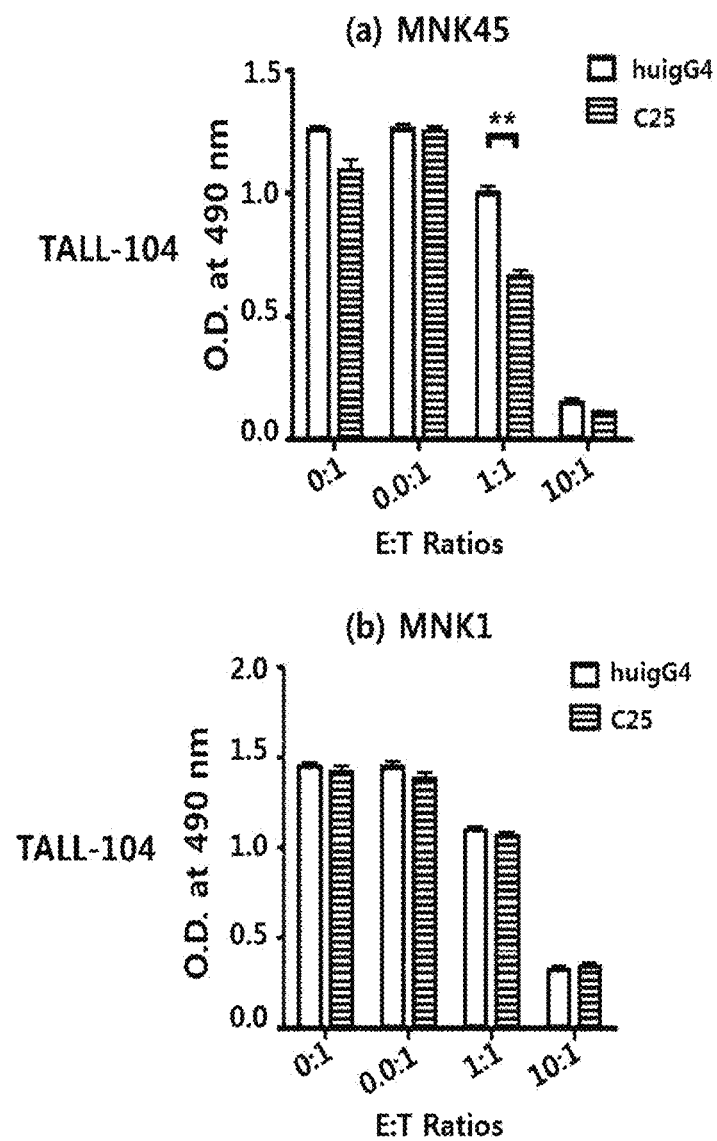

[Fig. 28]
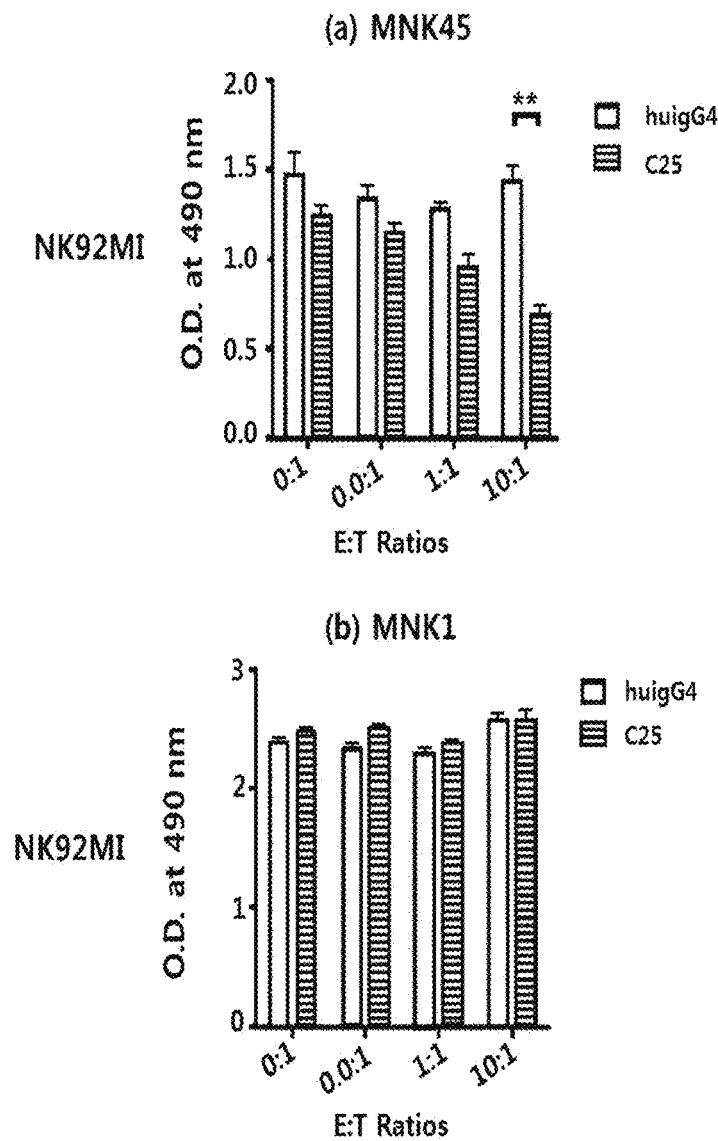

[Fig. 29]
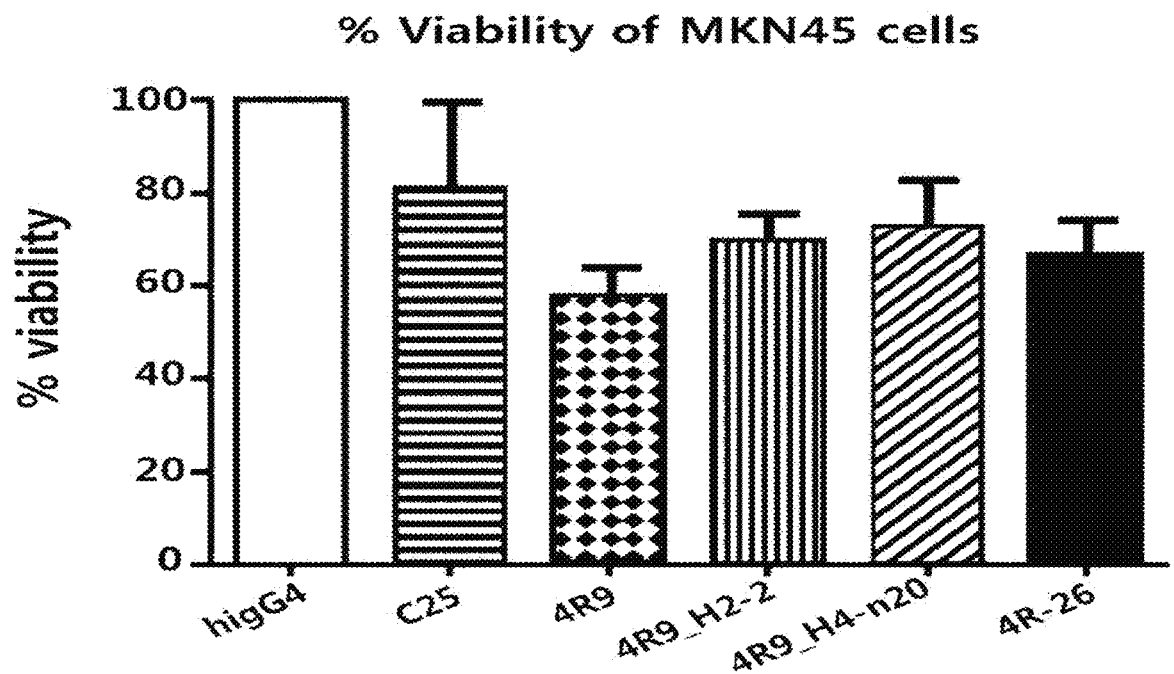

ANTI-CEACAM1 ANTIBODY AND USE THEREOF

TECHNICAL FIELD

The present invention relates to an anti-CEACAM1 antibody that specifically binds to CEACAM1, and a use thereof.

BACKGROUND ART

Carcinoembryonic antigen-related cell adhesion molecule 1 (hereinafter, referred to as CEACAM1), a transmembrane glycoprotein, belongs to the carcinoembryonic antigen (CEA) family. Among CEA family members, CEACAM1, CEACAM3, CEACAM4, CEACAM5, CEACAM6, CEACAM7 and CEACAM8 are expressed in humans. More importantly, CEACAM1 is the only member of CEA family expressed in lymphocyte populations including activated T cells and natural killer cells. CEACAM1 has been reported highly expressed in cancer cells. In addition, low levels of CEACAM1 expression has also been observed in epithelial cells, endothelial cells, and myeloid cells.

On the surface of lymphocytes, CEACAM1 plays a role in the regulation of immune responses. Specifically, CEACAM1 has turned out to be an inhibitory receptor for activated T cells including those contained within the human intestinal epithelium (Gray-Owen & Bloomberg, *Nat. Rev. Immunol.* 2006; 6:433-446; Morales et al., *J. Immunol*, 1999; 163: 1363-1370).

In particular, CEACAM1 is recognized as an immune checkpoint molecule similar to PD-1 and CTLA-4, playing a crucial role in modulating T cell activation. The immune checkpoint pathways protect tissues from immune-mediated damages under non-inflammatory physiological conditions. When CEACAM1 is activated on T lymphocytes, mainly upon CEACAM1-CEACAM1 trans-homophilic engagement, CEACAM1 signals to inhibit TCR-mediated inflammatory pathways by recruiting phosphatases to its own cytoplasmic ITIM motif (Chen et al., *J. Immunol.* 2008; 180: 6085-6093). Thus, suppression of immune checkpoint pathways in the context of cancer has emerged as a promising anti-cancer treatment strategy.

Studies on several human tumor types have reported that tumors can avoid immunity by inducing CEACAM1. In addition, in preclinical animal tumor models, it has been shown that blocking CEACAM1 interactions using monoclonal antibodies (mAbs) can enhance immune responses against tumors, promoting tumor suppression (Ortenberg et al., *Mol. Cancer Ther.* 2012; 11(6):1300-1310).

One of the biggest issues with conventional anti-cancer drugs is that treatment renders detrimental side effects as compared to their limited anti-cancer efficacies with high recurrence rates. On the other hand, a recently spotlighted approach, so-called immune checkpoint blockade, eliminates cancer by reactivating tumor-reactive exhausted T cells instead of directly killing cancer cells. This type of approach seems relatively safe and effective because it utilizes host immune functions to eliminate cancer with being able to keep irrelevant normal cells untouched. In the case of PD-1-targeting nivolumab from Bristol-Myers Squibb, the toxicity profile is in the manageable range as compared to those of conventional anti-cancer drugs, while its anti-cancer effects are dramatically higher than those of conventional drugs. In a phase III study of head-to-head comparison between nivolumab and dacarbazine, a standard chemotherapeutic agent, in treating metastatic melanoma patients, published in 2015, for example, nivolumab showed 40% objective response rate (95% CI, 33.3 to 47.0) compared to 13.9% ORR (95% CI, 9.5 to 19.4) by dacarbazine. The median progression-free survival was 5.1 months in the nivolumab group versus 2.2 months in the dacarbazine group. Toxicity profiling also convinced superiority of nivolumab to dacarbazine (Robert et al., *New Engl. J. Med.* 2015; 372:320-330).

Meanwhile, CEACAM1-blocking antibody acts on CEACAM1 expressed on the surface of cytotoxic T cells and of natural killer cells, interacting with CEACAM1 molecules overexpressed on tumor cells. Therefore, in case of CEACAM1-overexpressing tumors, CEACAM1-targeting antibody is expected to block CEACAM1-CEACAM1 homophilic suppressive interaction between T/NK cell and tumor cell, thereby reactivating anti-tumor T/NK cell responses. The CEACAM1-targeting antibody currently under development (a phase 1 clinical trial was prematurely terminated in February 2017) recognizes CEACAM3 and CEACAM5 in addition to CEACAM1. Such an off-target recognition property of this BMS clone may be due to its epitope sequences in N-domain that are highly homologous among human CEACAM1, CEACAM3 and CEACAM5.

DISCLOSURE OF INVENTION

Technical Problem

Therefore, in order to develop an anti-CEACAM1 antibody that specifically binds to CEACAM1, the present inventors have endeavored to find that an anti-CEACAM1 antibody binds to the N-domain of CEACAM1 and does not cross-react with CEACAM3, CEACAM5, CEACAM6 or CEACAM8, and have completed the present invention.

Solution to Problem

In accordance with one object of the present invention, there is provided an anti-CEACAM1 antibody or a fragment thereof comprising: light chain CDR1 comprising one of the amino acid sequences selected from the group consisting of SEQ ID NOS: 1 to 8; light chain CDR2 comprising one of the amino acid sequences selected from the group consisting of SEQ ID NOS: 9 to 16; light chain CDR3 comprising one of the amino acid sequences selected from the group consisting of SEQ ID NOS: 17 to 29; heavy chain CDR1 comprising one of the amino acid sequences selected from the group consisting of SEQ ID NOS: 30 to 38; heavy chain CDR2 comprising one of the amino acid sequences selected from the group consisting of SEQ ID NOS: 39 to 46; and heavy chain CDR3 comprising one of the amino acid sequences selected from the group consisting of SEQ ID NOS: 47 to 55.

In accordance with another object of the present invention, there is provided an anti-CEACAM1 antibody or a fragment thereof comprising: light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 23, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Further, in accordance with another object of the present invention, there is provided an anti-cancer agent comprising the anti-CEACAM1 antibody or a fragment thereof described above as an active ingredient.

Furthermore, in accordance with another object of a present invention, there is provided an anti-cancer adjuvant comprising the anti-CEACAM1 antibody or the fragment thereof described above as an active ingredient.

Also, in accordance with another object of the present invention, there is provided a composition for treating cancer comprising the anti-cancer adjuvant described above and a cell therapeutic agent.

Moreover, in accordance with another object of the present invention, there is provided a method for treating cancer comprising administering to a subject lymphocytes contacted with the anti-CEACAM1 antibody or a fragment thereof described above.

In addition, in accordance with another object of the present invention, there is provided a method for inhibiting proliferation of CEACAM1-expressing tumor cells, which comprises contacting the CEACAM1-expressing tumor cells with the anti-CEACAM1 antibody or a fragment thereof.

Advantageous Effects of Invention

An anti-CEACAM1 antibody according to the present invention specifically binds to CEACAM1, and thereby activates the anti-cancer immune functions of cytotoxic T cells and natural killer cells, and thus, it can be effectively used as an anti-cancer agent and a composition for treating cancer.

BRIEF DESCRIPTION OF DRAWINGS

FIG. 1 is a schematic diagram of the structure of recombinant CEACAM1 prepared according to one embodiment.

FIG. 2 shows the binding ability of anti-CEACAM1 antibodies depending on the constitutive domains of recombinant CEACAM1.

FIG. 3 illustrates comparative results of the binding of C25 to recombinant CEACAM1 depending on the concentrations of C25.

FIG. 4 demonstrates the binding of anti-CEACAM1 antibodies to CEACAM1 depending on the concentrations of anti-CEACAM1 antibodies.

FIG. 5 depicts the binding ability of CEACAM1 expressed on the surface of CEACAM1-Jurkat T cell line depending on the concentrations of C25 and C25-derived antibody clones:
(a) represents the binding ability to CEACAM1 expressed on the surface of a CEACAM1-Jurkat T cell line depending on the concentrations of C25; and (b) represents the binding ability to CEACAM1 expressed on the surface of a CEACAM1-Jurkat T cell line depending on the concentrations of C25-derived antibody clones.

FIG. 6 is a table showing the affinity of anti-CEACAM1 antibodies to CEACAM1. The affinity was obtained by the kinetic speed constant $K_{on}$ and $K_{off}$ and the equilibrium dissociation constant $K_D$.

FIG. 7 is a photograph showing the isoelectric point of C25. The first, second and third lanes are the results with IEF-Markers 3-10, huIgG4, and C25, respectively.

FIG. 8 shows the activation of the Jurkat E6.1 T cell line by C25 along with anti-CD3 (OKT3; 0.1 μg/ml) antibody through CD69, CD25 and Ki67 marker expressions. The concentrations of C25 and huIgG4 were 10 μg/ml.

FIG. 9 is a graph showing the number of the Jurkat E6.1 T cells activated by C25 along with OKT3 (0.1 μg/ml) and secretion levels of IL-2. The concentrations of C25 and huIgG4 were 10 μg/ml:
(a) represents the number of Jurkat E6.1 T cells proliferated by C25 along with OKT3; (b) shows the number of activated T cells expressing CD69 and Ki67 markers; and (c) shows the IL-2 secretion level of Jurkat E6.1 T cells activated by C25.

FIG. 10 illustrates the activation of Jurkat E6.1 T cell line by C25 along with OKT3 (0.1 μg/ml) through CD69, CD25 and Ki67 marker expression. The concentrations of C25 and huIgG4 were 25 μg/ml.

FIG. 11 is a graph showing the number of the Jurkat E6.1 T cells activated by C25 along with OKT3 (0.1 μg/ml) and secretion levels of IL-2. The concentrations of C25 and huIgG4 were 25 μg/ml:
(a) represents the number of Jurkat E6.1 T cells proliferated by C25 along with OKT3; (b) shows the number of activated T cells expressing CD69 and Ki67 markers; and (c) shows the IL-2 secretion level of Jurkat E6.1 T cells activated by C25 along with OKT3. The concentration of OKT3 was 0.1 μg/ml.

FIG. 12 demonstrates the activation of CEACAM1-overexpressing Jurkat E6.1 T cell line by C25 along with OKT3 through CD69, CD25 and Ki67 marker expression. The concentration of OKT3 was 0.1 μg/ml.

FIG. 13 is a graph showing the number of the CEACAM1-overexpressing Jurkat E6.1 T cells activated by C25 and secretion levels of IL-2. The concentrations of OKT3 and C25 or control Ab were 0.1 μg/ml and 10 μg/ml, respectively:
(a) represents the number of CEACAM1-overexpressing Jurkat E6.1 T cells proliferated by C25 along with OKT3; (b) shows the number of activated T cells expressing CD69 and Ki67 markers; and (c) shows the IL-2 secretion level of CEACAM1-overexpressing Jurkat E6.1 T cells activated by C25 along with OKT3.

FIG. 14 is a graph showing the number of the CEACAM1-overexpressing Jurkat E6.1 T cells activated by C25 along with OKT3 and secretion levels of IL-2. The concentrations of OKT3 and C25 or control Ab were 0.1 μg/ml and 25 μg/ml, respectively:
(a) represents the number of CEACAM1-overexpressing Jurkat E6.1 T cells proliferated by C25 along with OKT3; (b) shows the number of activated T cells expressing CD69 and Ki67 markers; and (c) shows the IL-2 secretion level of CEACAM1-overexpressing Jurkat E6.1 T cells activated by C25 along with OKT3.

FIG. 15 depicts the activation of CEACAM1-overexpressing Jurkat E6.1 T cell line by C25 along with OKT3 through CD69, CD25 and Ki67 marker expression. The concentration of OKT3 was 1 μg/ml.

FIG. 16 is a graph showing the number of the CEACAM1-overexpressing Jurkat E6.1 T cells activated by C25 along with OKT3 and secretion levels of IL-2. The concentrations of OKT3 and C25 or control Ab were 0.1 μg/ml and 10 μg/ml, respectively:
(a) represents the number of CEACAM1-overexpressing Jurkat E6.1 T cells proliferated by C25 along with OKT3; (b) shows the number of activated T cells expressing CD69 and Ki67 markers; and (c) shows the IL-2 secretion level of CEACAM1-overexpressing Jurkat E6.1 T cells activated by C25 along with OKT3.

FIG. 17 is a graph showing the number of the CEACAM1-overexpressing Jurkat E6.1 T cells activated by C25 along with OKT3 and secretion levels of IL-2. The concentrations of OKT3 and C25 or control Ab were 1 µg/ml and 25 µg/ml, respectively:

(a) represents the number of CEACAM1-overexpressing Jurkat E6.1 T cells proliferated by C25 along with OKT3; (b) shows the number of activated T cells expressing CD69 and Ki67 markers; and (c) shows the IL-2 secretion level of CEACAM1-overexpressing Jurkat E6.1 T cells activated by C25 along with OKT3.

FIG. 18 is a graph showing T cell activation by C25 treatment with the aid of TCR-induced NFAT activation. The concentrations of OKT3 and C25 or control Ab were 0.05 µg/ml and 10 µg/ml, respectively:

(a) shows the measurement results of TCR-induced NFAT activation by treating Jurkat-GFP/NFAT-luc cells, which do not express CEACAM1, with C25; and (b) is the measurement results of TCR-induced NFAT activation by treatment of Jurkat-CCM1/NFAT-luc cells overexpressing CEACAM1 with C25.

FIG. 19 is a result of T cell activation by C25 treatment with the aid of TCR-induced NFAT activation. The concentrations of OKT3 and C25 or control Ab were 0.1 µg/ml and 10 µg/ml, respectively:

(a) shows the measurement results of TCR-induced NFAT activation by treatment of Jurkat-GFP/NFAT-luc cells, which do not express CEACAM1, with C25; and (b) is the measurement results of TCR-induced NFAT activation by treatment of Jurkat-CCM1/NFAT-luc cells overexpressing CEACAM1 with C25.

FIG. 20 is a graph showing the increase in NFAT luciferase activity of T cells by anti-CEACAM1 antibodies including C25 in comparison along with the control. The concentrations of OKT3 and anti-CEACAM or control Ab were 0.1 µg/ml and 10 µg/ml, respectively:

FIG. 21 provides photographs showing staining results with C25 to evaluate the degree of CEACAM1 expressions in normal tissues of a human and a monkey.

FIG. 22 provides photographs showing staining results with huIgG4 in normal tissues of a human and a monkey.

FIG. 23 demonstrates the cross reactivity of anti-CEACAM1 antibodies with CEACAM family proteins.

FIG. 24 shows the cross reactivity of anti-CEACAM1 antibodies with CEACAM family proteins.

FIG. 25 shows that C25 (a) and C25-derived anti-CEACAM1 antibody clones (b) do not cross-react with CEACAM3, CEACAM5, CEACAM6 or CEACAM8 expressed on the cell surface.

FIG. 26 depicts that C25 (a) and C25-derived anti-CEACAM1 antibody clones (b) bind not only to human CEACAM1 but also to monkey CEACAM1 by examining the binding ability to a protein expressed on the cell surface.

FIG. 27 illustrates C25-mediated enhancement effect on the anti-cancer activity of CEACAM1⁺ TALL-104 T cells against CEACAM1⁺ cancer cells:

(a) shows the survival rates of cancer cells when TALL-104 T cells and CEACAM1⁺ MNK45 cancer cells were co-cultured in the presence of C25 at various Effector:Target (E:T) ratios; and (b) shows the survival rates of cancer cells when TALL-104 T cells and CEACAM1⁻ MNK1 cancer cells were co-cultured in the presence of C25 at various E:T ratios.

FIG. 28 is a graph showing C25-mediated enhancement effect on the anti-cancer activity of CEACAM1⁺ NK92MI NK cells against CEACAM1⁺ cancer cells:

(a) shows the survival rates of cancer cells when CEACAM1⁺ NK92MI NK cells and CEACAM1⁺ MNK45 cancer cells were co-cultured in the presence of C25 at various E:T ratios; and (b) shows the survival rates of cancer cells when CEACAM1⁺ NK92MI NK cells and CEACAM1⁺ MNK1 cancer cells were co-cultured in the presence of C25 at various E:T ratios.

FIG. 29 is a graph showing the enhancement levels on the anti-cancer activity of CEACAM1⁺ TALL-104 cells activated by C25 and C25-derived antibody clones against CEACAM1⁺ cancer cells:

The cancer cell death by TALL-104 cells promoted by C25 and C25-derived antibody clones was shown as the cancer cell survival rates compared to those by the control antibody when CEACAM1⁺ TALL-104 T cells were co-cultured with CEACAM1⁺ cancer cells (MKN45) at an E:T ratio of 1:1.

BEST MODE FOR CARRYING OUT THE INVENTION

Hereinafter, the present invention is described in detail.

The present invention provides an anti-CEACAM1 antibody or a fragment thereof comprising: light chain CDR1 comprising one of the amino acid sequences selected from the group consisting of SEQ ID NOS: 1 to 8; light chain CDR2 comprising one of the amino acid sequences selected from the group consisting of SEQ ID NOS: 9 to 16; light chain CDR3 comprising one of the amino acid sequences selected from the group consisting of SEQ ID NOS: 17 to 29; heavy chain CDR1 comprising one of the amino acid sequences selected from the group consisting of SEQ ID NOS: 30 to 38; heavy chain CDR2 comprising one of the amino acid sequences selected from the group consisting of SEQ ID NOS: 39 to 46; and heavy chain CDR3 comprising one of the amino acid sequences selected from the group consisting of SEQ ID NOS: 47 to 55.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 17, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 56, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

Further, the antibody or the fragment thereof described above may comprise a light chain comprising the amino acid sequence represented by SEQ ID NO: 106, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 18, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Furthermore, the antibody or the fragment thereof described above may comprise a light chain variable domain comprising the amino acid sequence represented by SEQ ID NO: 58, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

In addition, the antibody or the fragment thereof described above may comprise a light chain comprising the amino acid sequence represented by SEQ ID NO: 107, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 19, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 60, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

Moreover, the antibody or the fragment thereof described above may comprise a light chain comprising the amino acid sequence represented by SEQ ID NO: 108, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 20, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 62, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

Moreover, the antibody or the fragment thereof described above may comprise a light chain comprising the amino acid sequence represented by SEQ ID NO: 109, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 10, light chain CDR3 comprising the amino acid sequence represented by SEQ ID NO: 17, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 64, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

The antibody or the fragment thereof described above may comprise a light chain comprising the amino acid sequence represented by SEQ ID NO: 110, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 10, light chain CDR3 comprising the amino acid sequence represented by SEQ ID NO: 21, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 66, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

Further, the antibody or the fragment thereof described above may comprise a light chain comprising the amino acid sequence represented by SEQ ID NO: 111, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 11, light chain CDR3 comprising the amino acid sequence represented by SEQ ID NO: 22, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 68, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

Furthermore, the antibody or the fragment thereof described above may comprise a light chain comprising the amino acid sequence represented by SEQ ID NO: 112, and a heavy chain comprising the amino acid sequence represented by SEQ ID NO: 121.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 10, light chain CDR3 comprising the amino acid sequence represented by SEQ ID NO: 17, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 48.

Also, the antibody or the fragment thereof described above may comprise a light chain variable domain comprising the amino acid sequence represented by SEQ ID NO: 64, and a heavy chain variable domain comprising the amino acid sequence represented by SEQ ID NO: 88. Herein, if the CDR1, CDR2, and CDR3 of the heavy chain variable domain are identical, the framework portion can be modified. Especially, the amino acid sequences of some of the framework portion can be modified to produce humanized antibodies.

Moreover, the antibody or the fragment thereof described above may comprise a light chain comprising the amino acid sequence represented by SEQ ID NO: 110, and a heavy chain comprising the amino acid sequence represented by SEQ ID NO: 122.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 10, light chain CDR3 comprising the amino acid sequence represented by SEQ ID NO: 17, heavy chain CDR1 comprising the amino acid sequence represented by SEQ ID NO: 31, heavy chain CDR2 comprising the amino acid sequence represented by SEQ ID NO: 39, and heavy chain CDR3 comprising the amino acid sequence represented by SEQ ID NO: 47.

The antibody or the fragment thereof described above may comprise a light chain variable domain comprising the amino acid sequence represented by SEQ ID NO: 64, and a heavy chain variable domain comprising the amino acid sequence represented by SEQ ID NO: 90. Herein, if the CDR1, CDR2, and CDR3 of the heavy chain variable domain are identical, the framework portion can be modified. Especially, the amino acid sequences of some of the framework portion can be modified to produce humanized antibodies.

Also, the antibody or the fragment thereof described above may comprise a light chain comprising the amino acid sequence represented by SEQ ID NO: 110, and a heavy chain comprising the amino acid sequence represented by SEQ ID NO: 123.

Specifically, the anti-CEACAM1 antibody or the fragment thereof described above may comprise light chain CDR1 comprising the amino acid sequence represented by SEQ ID NO: 2, light chain CDR2 comprising the amino acid sequence represented by SEQ ID NO: 12, light chain CDR3 comprising the amino acid sequence represented by SEQ ID NO: 24, heavy chain CDR1 comprising the amino acid sequence represented by SEQ ID NO: 32, heavy chain CDR2 comprising the amino acid sequence represented by SEQ ID NO: 40, and heavy chain CDR3 comprising the amino acid sequence represented by SEQ ID NO: 49.

Further, the antibody or the fragment thereof described above may comprise a light chain variable domain comprising the amino acid sequence represented by SEQ ID NO: 72, and a heavy chain variable domain comprising the amino acid sequence represented by SEQ ID NO: 92. Herein, if the CDR1, CDR2, and CDR3 of the heavy chain variable domain are identical, the framework portion can be modified. Especially, the amino acid sequences of some of the framework portion can be modified to produce humanized antibodies.

Furthermore, the antibody or the fragment thereof described above may comprise a light chain comprising the amino acid sequence represented by SEQ ID NO: 114, and a heavy chain comprising the amino acid sequence represented by SEQ ID NO: 124.

Specifically, the anti-CEACAM1 antibody or the fragment thereof described above may comprise light chain CDR1 comprising the amino acid sequence represented by SEQ ID NO: 3, light chain CDR2 comprising the amino acid sequence represented by SEQ ID NO: 13, light chain CDR3 comprising the amino acid sequence represented by SEQ ID NO: 25, heavy chain CDR1 comprising the amino acid sequence represented by SEQ ID NO: 33, heavy chain CDR2 comprising the amino acid sequence represented by SEQ ID NO: 41, and heavy chain CDR3 comprising the amino acid sequence represented by SEQ ID NO: 50.

Moreover, the antibody or the fragment thereof described above may comprise a light chain variable domain comprising the amino acid sequence represented by SEQ ID NO: 74, and a heavy chain variable domain comprising the amino acid sequence represented by SEQ ID NO: 94. Herein, if the CDR1, CDR2, and CDR3 of the heavy chain variable domain are identical, the framework portion can be modified. Especially, the amino acid sequences of some of the framework portion can be modified to produce humanized antibodies.

The antibody or the fragment thereof described above may comprise a light chain comprising the amino acid sequence represented by SEQ ID NO: 115, and a heavy chain comprising the amino acid sequence represented by SEQ ID NO: 125.

Specifically, the anti-CEACAM1 antibody or the fragment thereof described above may comprise light chain CDR1 comprising the amino acid sequence represented by SEQ ID NO: 4, light chain CDR2 comprising the amino acid sequence represented by SEQ ID NO: 14, light chain CDR3 comprising the amino acid sequence represented by SEQ ID NO: 23, heavy chain CDR1 comprising the amino acid sequence represented by SEQ ID NO: 34, heavy chain CDR2 comprising the amino acid sequence represented by SEQ ID NO: 42, and heavy chain CDR3 comprising the amino acid sequence represented by SEQ ID NO: 51.

Also, the antibody or the fragment thereof described above may comprise a light chain variable domain comprising the amino acid sequence represented by SEQ ID NO: 76, and a heavy chain variable domain comprising the amino acid sequence represented by SEQ ID NO: 96. Herein, if the CDR1, CDR2, and CDR3 of the heavy chain variable domain are identical, the framework portion can be modified. Especially, the amino acid sequences of some of the framework portion can be modified to produce humanized antibodies.

Further, the antibody or the fragment thereof described above may comprise a light chain comprising the amino acid sequence represented by SEQ ID NO: 116, and a heavy chain comprising the amino acid sequence represented by SEQ ID NO: 126.

Specifically, the anti-CEACAM1 antibody or the fragment thereof described above may comprise light chain CDR1 comprising the amino acid sequence represented by SEQ ID NO: 5, light chain CDR2 comprising the amino acid sequence represented by SEQ ID NO: 15, light chain CDR3 comprising the amino acid sequence represented by SEQ ID NO: 26, heavy chain CDR1 comprising the amino acid sequence represented by SEQ ID NO: 35, heavy chain CDR2 comprising the amino acid sequence represented by SEQ ID NO: 43, and heavy chain CDR3 comprising the amino acid sequence represented by SEQ ID NO: 52.

Furthermore, the antibody or the fragment thereof described above may comprise a light chain variable domain comprising the amino acid sequence represented by SEQ ID NO: 78, and a heavy chain variable domain comprising the amino acid sequence represented by SEQ ID NO: 98. Herein, if the CDR1, CDR2, and CDR3 of the heavy chain variable domain are identical, the framework portion can be modified. Especially, the amino acid sequences of some of the framework portion can be modified to produce humanized antibodies.

Moreover, the antibody or the fragment thereof described above may comprise a light chain comprising the amino acid sequence represented by SEQ ID NO: 117, and a heavy chain comprising the amino acid sequence represented by SEQ ID NO: 127.

Specifically, the anti-CEACAM1 antibody or the fragment thereof described above may comprise light chain CDR1 comprising the amino acid sequence represented by SEQ ID NO: 6, light chain CDR2 comprising the amino acid sequence represented by SEQ ID NO: 16, light chain CDR3 comprising the amino acid sequence represented by SEQ ID NO: 27, heavy chain CDR1 comprising the amino acid sequence represented by SEQ ID NO: 36, heavy chain CDR2 comprising the amino acid sequence represented by SEQ ID NO: 44, and heavy chain CDR3 comprising the amino acid sequence represented by SEQ ID NO: 53.

The antibody or the fragment thereof described above may comprise a light chain variable domain comprising the amino acid sequence represented by SEQ ID NO: 80, and a heavy chain variable domain comprising the amino acid sequence represented by SEQ ID NO: 100. Herein, if the CDR1, CDR2, and CDR3 of the heavy chain variable domain are identical, the framework portion can be modified. Especially, the amino acid sequences of some of the framework portion can be modified to produce humanized antibodies.

Also, the antibody or the fragment thereof described above may comprise a light chain comprising the amino acid sequence represented by SEQ ID NO: 118, and a heavy chain comprising the amino acid sequence represented by SEQ ID NO: 128.

Specifically, the anti-CEACAM1 antibody or the fragment thereof described above may comprise light chain CDR1 comprising the amino acid sequence represented by SEQ ID NO: 7, light chain CDR2 comprising the amino acid sequence represented by SEQ ID NO: 14, light chain CDR3 comprising the amino acid sequence represented by SEQ ID NO: 28, heavy chain CDR1 comprising the amino acid sequence represented by SEQ ID NO: 37, heavy chain CDR2 comprising the amino acid sequence represented by SEQ ID NO: 45, and heavy chain CDR3 comprising the amino acid sequence represented by SEQ ID NO: 54.

Further, the antibody or the fragment thereof described above may comprise a light chain variable domain comprising the amino acid sequence represented by SEQ ID NO: 82, and a heavy chain variable domain comprising the amino acid sequence represented by SEQ ID NO: 102. Herein, if the CDR1, CDR2, and CDR3 of the heavy chain variable domain are identical, the framework portion can be modified. Especially, the amino acid sequences of some of the framework portion can be modified to produce humanized antibodies.

Furthermore, the antibody or the fragment thereof described above may comprise a light chain comprising the amino acid sequence represented by SEQ ID NO: 119, and a heavy chain comprising the amino acid sequence represented by SEQ ID NO: 129.

Specifically, the anti-CEACAM1 antibody or the fragment thereof described above may comprise light chain CDR1 comprising the amino acid sequence represented by SEQ ID NO: 8, light chain CDR2 comprising the amino acid sequence represented by SEQ ID NO: 15, light chain CDR3 comprising the amino acid sequence represented by SEQ ID NO: 29, heavy chain CDR1 comprising the amino acid sequence represented by SEQ ID NO: 38, heavy chain CDR2 comprising the amino acid sequence represented by SEQ ID NO: 46, and heavy chain CDR3 comprising the amino acid sequence represented by SEQ ID NO: 55.

Moreover, the antibody or the fragment thereof described above may comprise a light chain variable domain comprising the amino acid sequence represented by SEQ ID NO: 84, and a heavy chain variable domain comprising the amino acid sequence represented by SEQ ID NO: 104. Herein, if the CDR1, CDR2, and CDR3 of the heavy chain variable domain are identical, the framework portion can be modified. Especially, the amino acid sequences of some of the framework portion can be modified to produce humanized antibodies.

The antibody or the fragment thereof described above may comprise a light chain comprising the amino acid sequence represented by SEQ ID NO: 120, and a heavy chain comprising the amino acid sequence represented by SEQ ID NO: 130.

Specifically, the anti-CEACAM1 antibody or the fragment thereof described above may comprise light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 23, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 70, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

Further, the antibody or the fragment thereof described above may comprise a light chain comprising the amino acid sequence represented by SEQ ID NO: 113, and a heavy chain comprising the amino acid sequence represented by SEQ ID NO: 121.

The term "antibody" as used herein refers to an immune protein that binds to an antigen and interferes with the action of the antigen or eliminates the antigen. There are five types of antibodies, IgM, IgD, IgG, IgA and IgE, each of which contains a heavy chain produced from heavy chain constant region genes μ, δ, γ, α, and ε. In an antibody technology, IgG is mainly used. Four kinds of isotypes of IgG are IgG1, IgG2, IgG3 and IgG4, and their structures and functional characteristics may be different.

Also, the IgG has a Y-shaped, highly stable structure (molecular weight, about 150 kDa) composed of two heavy chain proteins (about 50 kDa) and two light chain proteins (about 25 kDa). The light and heavy chains of an antibody are divided into constant regions in which the amino acid sequences are identical among antibodies and variable regions in which the amino acid sequences are different among antibodies. A heavy chain constant region contains the CH1, H (hinge), CH2, and CH3 domains. Each domain is composed of two β-sheets and is linked by a disulfide bond in the molecule. Two variable regions of heavy and light chains are combined to form an antigen binding site. The antigen binding site is present on two arms of an antibody, one at each arm, and such portion that can bind to an antigen is called Fab (antibody binding fragment), and a portion that cannot bind to an antigen is called Fc (crystalizable fragment). The Fab and Fc are connected by a flexible hinge region.

Also, the term "CDR" as used herein refers to a hypervariable region which is a site having a different amino acid sequence for each antibody in the heavy chain and light chain variable regions of the antibody, and refers to an antigen-binding site. With regard to a stereostructure of an antibody, the CDR forms a loop shape on the surface of the antibody, and a framework region (FR) is present under the loop to structurally support the CDR. There are three loop structures in each of the heavy chain and the light chain, and these six loop structures are combined with each other to directly contact an antigen.

Also, the antibody fragment may be one selected from the group consisting of Fab, scFv, F(ab)$_2$, and Fv. An antibody fragment refers to antigen binding domains which excludes the Fc region, which serves an effector function to transfer binding stimuli with an antigen to cells or complements, etc., and may include $3^{rd}$ generation antibody fragments such as a single domain antibody or a minibody, etc.

In addition, the antibody fragments have good permeability into tissues and tumors since they have small sizes compared to a full structure IgG. They have has an advantage of low production cost since they can be produced in bacteria, and can be used when the function of transferring binding stimuli with an antigen to cells or complements is not desired since they have no Fc. Antibody fragments are suitable for in vivo diagnosis due to their short half-life in the human body. However, when some basic, acidic or neutral amino acids among the amino acids constituting the antibody are replaced with each other, the isoelectric point (pI) can be changed. The change in the isoelectric point of the antibody can induce changes such as a decrease in toxic side effects in vivo or an increase in the water solubility of the antibody, and thus, in the case of a therapeutic antibody, a full structure IgG can be used considering its affinity and the structural form.

Also, the light chain variable domain of the anti-CEACAM1 antibody or a fragment thereof of the present invention may have a light chain variable domain sequence comprising the amino acid sequence represented by SEQ ID NOS: 56, 58, 60, 62, 64, 66, 68, 70, 72, 74, 76, 78, 80, 82 or 84, or it may have homology of 97%, 98% or 99% with the above light chain variable domain sequence.

Further, the heavy chain variable domain of the anti-CEACAM1 antibody or a fragment thereof of the present invention may have a heavy chain variable domain sequence comprising the amino acid sequence represented by SEQ ID NOS: 86, 88, 90, 92, 94, 96, 98, 102 or 104, or it may have homology of 97%, 98% or 99% with the above heavy chain variable domain sequence.

Furthermore, the anti-CEACAM1 antibody or a fragment thereof of the present invention may have homology of 97%, 98% or 99% with a light chain variable domain sequence comprising the amino acid sequence represented by SEQ ID NOS: 56, 58, 60, 62, 64, 66, 68, 70, 72, 74, 76, 78, 80, 82 or 84, and a heavy chain variable domain sequence comprising the amino acid sequence represented by SEQ ID NOS: 86, 88, 90, 92, 94, 96, 98, 102 or 104.

Moreover, the anti-CEACAM1 antibody refers to an antibody that binds to CEACAM1. As used herein, the term "C25" is an embodiment of the anti-CEACAM1 antibody. The C25 may comprise light chain CDR1 comprising the amino acid sequence represented by SEQ ID NO: 1, light chain CDR2 comprising the amino acid sequence represented by SEQ ID NO: 9, light chain CDR3 comprising the amino acid sequence represented by SEQ ID NO: 23, heavy chain CDR1 comprising the amino acid sequence represented by SEQ ID NO: 30, heavy chain CDR2 comprising the amino acid sequence represented by SEQ ID NO: 39, and heavy chain CDR3 comprising the amino acid sequence represented by SEQ ID NO: 47.

Also, the antibody or the fragment thereof described above may comprise a light chain variable domain comprising the amino acid sequence represented by SEQ ID NO: 70, and a heavy chain variable domain comprising the amino acid sequence represented by SEQ ID NO: 86. Herein, if the CDR1, CDR2, and CDR3 of the heavy chain variable domain are identical, the framework portion can be modified. Especially, the amino acid sequences of some of the framework portion can be modified to produce humanized antibodies.

The CD25 described above may comprise a light chain comprising the amino acid sequence represented by SEQ ID NO: 113, and a heavy chain comprising the amino acid sequence represented by SEQ ID NO: 121.

A variant of C25 may comprise light chain CDR1 comprising the amino acid sequence represented by SEQ ID NO: 1, light chain CDR2 comprising the amino acid sequence represented by SEQ ID NO: 9, 10 or 11, light chain CDR3 comprising the amino acid sequence represented by SEQ ID NO: 17, 18, 19, 20, 21 or 22, heavy chain CDR1 comprising the amino acid sequence represented by SEQ ID NO: 30 or 31, heavy chain CDR2 comprising the amino acid sequence represented by SEQ ID NO: 39, and heavy chain CDR3 comprising the amino acid sequence represented by SEQ ID NO: 47 or 48. Specifically, in one embodiment of the present invention, the variants of C25 were shown in Table 1 as 1-19, 1-23, 3-07, 3-27, 4R9, 4R20, 4R26, 4R9_H2-2 and 4R9_H4-n20.

Also, the anti-CEACAM1 antibody or the fragment thereof described above recognizes the N-domain and the B-domain of CEACAM1 as an epitope. Also, the antibody does not cross-react with CEACAM3, CEACAM5, CEACAM6 or CAECAM8.

Further, the anti-CEACAM1 antibody of the present invention can be easily prepared by a known monoclonal antibody preparation technique. Methods for preparing monoclonal antibodies can be implemented by preparing hybridomas using B lymphocytes from immunized animals, or by using phage display techniques, but are not limited thereto.

The present invention also provides an anti-cancer agent comprising the anti-CEACAM1 antibody or a fragment thereof as an active ingredient.

The anti-cancer agent of the present invention comprising the anti-CEACAM1 antibody or the fragment thereof as an active ingredient can be used for treating cancers or tumors overexpressing CEACAM1. Specifically, when a T cell receptor (TCR) of a cytotoxic T cell, which plays a role in removing cancer cells, recognizes an epitope of cancer or a tumor cell, the LCK (lymphocyte-specific protein tyrosine kinase) protein bound to the CD4 (cluster of differentiation 4), one component of the TCR phosphorylates CD3ζ (cluster of differentiation 30, another component of the TCR. When ZAP70 (Zeta-chain-associated protein kinase 70) protein is bound to the phosphorylated CD3ζ, the terminal portion of ZAP70 protein is phosphorylated again by LCK protein, thereby activating T cell inflammatory pathways including RAS-MAPK (Ras-MAP kinase) signal transduction, and thus, T cells are activated.

However, in the case of cancer cells or tumor cells overexpressing the CEACAM1, SHP1 (Src homology region 2 domain-containing phosphatase-1) protein is bound to the CEACAM1 ITIM (immunoreceptor tyrosine-based inhibition motif) portion which is phosphorylated by the LCK protein bound to the end of CD4 of the TCR due to the CEACAM1-CEACAM1 interaction. Also, the terminal of CD3ζ is dephosphorylated as well as ZAP70 by the SHP1 protein, and thus, TCR downstream signaling pathways including RAS-MAPK pathway is not activated and, as a result, T cells are not activated.

Thus, the anti-CEACAM1 antibody or the fragment thereof can be used as an anti-cancer agent by blocking the CEACAM1-CEACAM1 interaction in advance through binding to CEACAM1 expressed in cytotoxic T cells, natural killer cells and cancer cells.

Also, the term "anti-cancer" as used herein encompasses "prevention" and "treatment." Herein, "prevention" refers to all actions of preventing cancer proliferation and delaying the progress of cancer by administration of the anti-cancer agent, and "treatment" refers to all actions of improving or ameliorating the symptoms of cancer by administration of the antibody of the present invention.

Also, the term "cancer" as used herein, may be selected from the group consisting of gastric cancer, thyroid cancer, pancreatic cancer, melanoma, lung cancer and myeloma, but, is not limited thereto. It may include solid cancer and blood cancer and is not particularly limited as long as it has CEACAM1 as a receptor and its immune checkpoint pathway is abnormal. Also, the present invention provides an anti-cancer adjuvant comprising the anti-CEACAM1 antibody or a fragment thereof as an active ingredient.

In addition, the present invention provides a composition for treating cancer comprising the anti-cancer adjuvant described above and a cell therapeutic agent. The cell therapy agent may include cytotoxic T cells or natural killer cells.

Also, the term "cell therapeutic agent" as used herein refers to a drug used for the purpose of prevention or treatment through a series of actions that change the biological characteristics by proliferating and selecting living autologous, allogenic, and xenogenic cells in vitro to restore the function of cells and tissues. Specifically, it may be cytotoxic T cells or natural killer cells.

Also, provided is a method for treating cancer using the anti-CEACAM1 antibody or a fragment thereof of the present invention. Specifically, the method may comprise administering to a subject lymphocytes contacted with the anti-CEACAM1 antibody or the fragment thereof. The lymphocytes are a kind of leukocytes, which account for about 25% of all leukocytes, and may be natural killer cells, T cells and B cells. Also, the lymphocytes may be obtained from a subject. Preferably, the lymphocytes may include at least one of cytotoxic T cells and natural killer cells. The cancer is as described above.

Also, the term "subject" as used herein refers to a person who is in a state where a disease can be alleviated, suppressed or treated by administering the anti-cancer adjuvant of the present invention, or is suffering from a disease.

Also, the term "contacting" as used herein also refers to mixing the anti-CEACAM1 antibody or a fragment thereof with cells expressing CEACAM1.

The term "administration" as used herein refers to introduction of an effective amount of a substance into a subject by an appropriate method, and the administration of a composition comprising the anti-CEACAM1 antibody or the fragment thereof of the present invention may be carried out via a general administration route which allows the substance to reach target tissues. Specifically, the administration may be parenteral administration (i.e., intravenous, subcutaneous, intraperitoneal or local administration, etc.) depending on the intended use, and preferably, it may be intravenous administration. In some cases of administration to solid tumors, local administration may be preferable in terms of rapid and easy access of the antibodies. The dosage varies depending on the patient's weight, age, sex, health condition, diet, the administration time, the administration method, the excretion rate, and the severity of a disease. The single dose may be about 0.001 to 10 mg/kg, which may be administered by a daily or weekly basis. The effective amount may be adjusted according to the discretion of a physician treating the patient.

A composition for treating cancer according to the present invention may be administered in a pharmaceutically effective amount to treat cancer cells or their metastasis or to inhibit cancer growth. The dosage may vary depending on the type of cancer, patient's age and weight, the nature and severity of symptoms, the type of current treatment, the number of treatments, the type and route of administration, etc., and can be easily determined by experts in the art.

As for the composition of the present invention, the pharmacological or physiological components described above may be administered concurrently or sequentially, or may be administered in combination with an additional conventional therapeutic agent sequentially or concurrently. Such administration may be single or multiple administrations. It is important to take into account all of the above factors and administer the amount which leads to a maximum effect with a minimal amount without side effects, which can be easily determined by those skilled in the art.

Also, the present invention provides a method for inhibiting proliferation of CEACAM1-expressing tumor cells using the anti-CEACAM1 antibody or a fragment thereof. Specifically, it may comprise contacting the CEACAM1-expressing tumor cells with the anti-CEACAM1 antibody or the fragment thereof.

MODE FOR THE INVENTION

Hereinafter, the present invention is explained in detail by Examples. The following Examples are intended to further illustrate the present invention without limiting its scope.

Example 1. Anti-CEACAM1 Antibody (C25)

Example 1.1 Preparation of Anti-CEACAM1 Antibody

The antibody fragment genes inserted in the pComb3X vector (Addgene; Cat. No. 63891) in the form of a single-chain variable fragment (scFv) were subjected to perform PCR to obtain the light chain variable region genes represented by SEQ ID NOS: 57, 59, 61, 63, 65, 67, 69, 71, 73, 75, 77, 79, 81, 83 or 85, and the heavy chain variable region gene represented by SEQ ID NOS: 87, 89, 91, 93, 95, 97, 99, 101, 103 or 105, which include the sequences recognized by each restriction enzyme. The heavy chain genes were treated with NotI and ApaI restriction enzymes and the light chain genes were treated with NotI and BamHI restriction enzymes.

The heavy and light chain genes were inserted into the pcIW vector (Promega; Cat. No. E1731) digested with the same restriction enzymes as for the heavy or light chain genes. Then, vectors containing both the heavy chain transcription unit and the light chain transcription unit were selected using restriction enzymes. The selected vectors were extracted using QIAGEN Plasmid Plus Midi Kit (QIAGEN; Cat. No. 12943), and the base sequences of the antibodies were finally identified by base sequence analysis using some of the extracted DNA. The amino acid sequences of the antibodies were analyzed based on the above base sequences. The amino acid sequences and base sequences of the analyzed antibodies are shown in Table 1 and Table 2.

TABLE 1

| | Light Chain | | | | | | Heavy chain | | | | | |
|---|---|---|---|---|---|---|---|---|---|---|---|---|
| | CDR1 | SEQ ID NO | CDR2 | SEQ ID NO | CDR3 | SEQ ID NO | CDR1 | SEQ ID NO | CDR2 | SEQ ID NO | CDR3 | SEQ ID NO |
| 1-19 | SSNIGNNY | 1 | ADSKRP | 9 | GAWDLSLNGYV | 17 | GFTFSNYA | 30 | ISHGGGSI | 39 | ARDPTKGYAPTFDY | 47 |
| 1-23 | SSNIGNNY | 1 | ADSKRP | 9 | GAWDVSHNGYV | 18 | GFTFSNYA | 30 | ISHGGGSI | 39 | ARDPTKGYAPTFDY | 47 |
| 3-07 | SSNIGNNY | 1 | ADSKRP | 9 | GAWDQSLNGYV | 19 | GFTFSNYA | 30 | ISHGGGSI | 39 | ARDPTKGYAPTFDY | 47 |
| 3-27 | SSNIGNNY | 1 | ADSKRP | 9 | GAWDSMGNGYV | 20 | GFTFSNYA | 30 | ISHGGGSI | 39 | ARDPTKGYAPTFDY | 47 |
| 4R9 | SSNIGNNY | 1 | ADSRRP | 10 | GAWDLSLNGYV | 17 | GFTFSNYA | 30 | ISHGGGSI | 39 | ARDPTKGYAPTFDY | 47 |
| 4R20 | SSNIGNNY | 1 | ADSRRP | 10 | GAWDASYNGYV | 21 | GFTFSNYA | 30 | ISHGGGSI | 39 | ARDPTKGYAPTFDY | 47 |
| 4R26 | SSNIGNNY | 1 | ADSKRL | 11 | GAWDGRLNGYV | 22 | GFTFSNYA | 30 | ISHGGGSI | 39 | ARDPTKGYAPTFDY | 47 |
| 4R9_H2-2 | SSNIGNNY | 1 | ADSRRP | 10 | GAWDLSLNGYV | 17 | GFTFSNYA | 30 | ISHGGGSI | 39 | ARDPTKGYAPLFDY | 48 |
| 4R9_H4-n20 | SSNIGNNY | 1 | ADSRRP | 10 | GAWDLSLNGYV | 17 | GFNFSNYA | 31 | ISHGGGSI | 39 | ARDPTKGYAPTFDY | 47 |
| C25 | SSNIGNNY | 1 | ADSKRP | 9 | GAWDASLNGYV | 23 | GFTFSNYA | 30 | ISHGGGSI | 39 | ARDPTKGYAPTFDY | 47 |
| C15 | SSSNIGNNY | 2 | ANSNRP | 12 | GTWDASLSAYV | 24 | GFTFSSYS | 32 | ISPNGGNK | 40 | AKDPYNIYQPLFDY | 49 |
| C16 | SSNIGSNT | 3 | ADNNRP | 13 | GTWDYSLSGYV | 25 | GFTFSNYS | 33 | ISSDGGSK | 41 | ARDPRKHVDRYFDY | 50 |
| C17 | SSNIGNNA | 4 | ANSHRP | 14 | GAWDASLNGYV | 23 | GFTFSDYS | 34 | IYPDDGNT | 42 | ARGSIWWLSLIPSSYNAMDV | 51 |
| C18 | SSNIGSNA | 5 | ADSHRP | 15 | GSWDDSLNAYV | 26 | GFTFSNYD | 35 | ISHSSGSK | 43 | ARDPLPCLIPKCSYYYAMDV | 52 |
| C19 | SSNIGSNY | 6 | SNSHRP | 16 | AAWDSSLNGYV | 27 | GFTFSGYA | 36 | IYHDGGST | 44 | ARVTVLCTTYGCSSYDGMDV | 53 |
| C22 | SSNIGSNN | 7 | ANSHRP | 14 | GSWDSSLNAYV | 28 | GFTFSDYD | 37 | IYSGSSSK | 45 | AKAPLPFYFRPKSYYYAMDV | 54 |
| C26 | SSNIGNN | 8 | ADSHRP | 15 | GAWDYSLSGYV | 29 | GFTFSGYD | 38 | ISYGGGSI | 46 | AKDRLPQKAVRHSYANGMDV | 55 |

TABLE 2

|  | Light chain variable region SEQ ID NO | Heavy chain variable region SEQ ID NO | Light chain SEQ ID NO | Heavy chain SEQ ID NO |
| --- | --- | --- | --- | --- |
| 1-19 | SEQ ID NO: 56, 57 | SEQ ID NO: 86, 87 | SEQ ID NO: 106 | SEQ ID NO: 121 |
| 1-23 | SEQ ID NO: 58, 59 | SEQ ID NO: 86, 87 | SEQ ID NO: 107 | SEQ ID NO: 121 |
| 3-07 | SEQ ID NO: 60, 61 | SEQ ID NO: 86, 87 | SEQ ID NO: 108 | SEQ ID NO: 121 |
| 3-27 | SEQ ID NO: 62, 63 | SEQ ID NO: 86, 87 | SEQ ID NO: 109 | SEQ ID NO: 121 |
| 4R9 | SEQ ID NO: 64, 65 | SEQ ID NO: 86, 87 | SEQ ID NO: 110 | SEQ ID NO: 121 |
| 4R20 | SEQ ID NO: 66, 67 | SEQ ID NO: 86, 87 | SEQ ID NO: 111 | SEQ ID NO: 121 |
| 4R26 | SEQ ID NO: 68, 69 | SEQ ID NO: 86, 87 | SEQ ID NO: 112 | SEQ ID NO: 121 |
| 4R9_H2-2 | SEQ ID NO: 64, 65 | SEQ ID NO: 88, 89 | SEQ ID NO: 110 | SEQ ID NO: 122 |
| 4R9_H4-n20 | SEQ ID NO: 64, 65 | SEQ ID NO: 90, 91 | SEQ ID NO: 110 | SEQ ID NO: 123 |
| C25 | SEQ ID NO: 70, 71 | SEQ ID NO: 86, 87 | SEQ ID NO: 113 | SEQ ID NO: 121 |
| C15 | SEQ ID NO: 72, 73 | SEQ ID NO: 92, 93 | SEQ ID NO: 114 | SEQ ID NO: 124 |
| C16 | SEQ ID NO: 74, 75 | SEQ ID NO: 94, 95 | SEQ ID NO: 115 | SEQ ID NO: 125 |
| C17 | SEQ ID NO: 76, 77 | SEQ ID NO: 96, 97 | SEQ ID NO: 116 | SEQ ID NO: 126 |
| C18 | SEQ ID NO: 78, 79 | SEQ ID NO: 98, 99 | SEQ ID NO: 117 | SEQ ID NO: 127 |
| C19 | SEQ ID NO: 80, 81 | SEQ ID NO: 100, 101 | SEQ ID NO: 118 | SEQ ID NO: 128 |
| C22 | SEQ ID NO: 82, 83 | SEQ ID NO: 102, 103 | SEQ ID NO: 119 | SEQ ID NO: 129 |
| C26 | SEQ ID NO: 84, 85 | SEQ ID NO: 104, 105 | SEQ ID NO: 120 | SEQ ID NO: 130 |

Thirty milliliters of ExpiHEK293F cells (ThermoFisher scientific; Cat. No. A14527) at a concentration of $2.5 \times 10^6$ cells/ml were treated and transfected with 30 μg of the extracted antibody DNA. On the next day following the transfection, an enhancer (ThermoFisher; Cat. No. A14524) was added to the transfected ExpiHEK293F cells and cultured in a shaking incubator for 7 days under the condition of 37° C., 8% $CO_2$ and 125 rpm, to produce anti-CEACAM1 antibody.

After the culture, the supernatant separated from the culture medium by centrifugation was incubated with 100 μl of protein A beads (Repligen; Cat. No. CA-PRI-0100) for 2 hours. The beads were then washed with 10 ml of a binding buffer (ThermoFisher Scientific; Cat. No. 21019). Thereafter, 200 μl of an elution buffer (ThermoFisher Scientific; Cat. No. 21004) was added to the beads, to separate the antibodies conjugated to the beads. The separated antibodies were neutralized by the addition of 10 μl of 1.5 M Tris-HCl pH 8.8 solution (Bio-Rad; Cat. No. 210005897).

Experimental Example 1. Evaluation of Binding Ability of Anti-CEACAM1 Antibody

Experimental Example 1.1. Evaluation of Binding Ability of Anti-CEACAM1 Antibody According to CEACAM1 Domain Thirty milliliters of ExpiHEK293F cells (ThermoFisher scientific; Cat. No. A14527) at a concentration of $2.5 \times 10^6$ cells/ml were treated and transfected with 30 μg of the DNA of CEACAM1 mutant proteins conjugated with a human immunoglobulin C kappa domain. Also, the enhancer (ThermoFisher; Cat. No. A14524) was added to the transfected ExpiHEK293F cells and cultured in a shaking incubator for 7 days under the condition of 37° C., 8% $CO_2$ and 125 rpm.

Then, the supernatant was separated from the culture medium and reacted with a kappa selection bead (GE Healthcare; Cat. No. 17-5458-01) for 2 hours. Thereafter, the beads were washed with 10 ml of a binding buffer and added with 200 μl of an elution buffer, to separate and purify the CEACAM1 mutant protein from the beads (FIG. 1). Each of the purified CEACAM1 mutant proteins (2.5 μg) was dissolved in 1,000 μl of PBS and dispensed into each well at 20 μl/well, and then reacted at 4° C. for 16 hours. Also, 1 μl of C25 was diluted in 1,000 μl of PBS and dispensed into each well at 25 μl/well, and then reacted at 37° C. for 1 hour. Then, each well was washed 3 times with a washing buffer prepared by diluting 10 μl of Tween 20 (Sigma-Aldrich; Cat. No. P9146) in 990 μl of PBS. Thereafter, human IgG conjugated with 1 μl of horse radish peroxidase (HRP) (HRP-conjugated anti-human IgG: Sigma; Cat. No. A0170) was diluted in 5000 μl of PBS, which was then dispensed into each well at 25 μl/well and incubated at 37° C. for 1 hour.

After completion of the reaction, the wells were washed three times with the washing buffer, and 25 μl of TMB solution (KPL; Cat. No. 52-00-03) was added to each well to induce color development. Then, 25 μl of 2 M $H_2SO_4$ was added to each well to stop the reaction, and the absorbance was measured at a wavelength of 450 nm.

As a result, in the case of C25, the N-domain and the B-domain were found to be essential sites for binding with full affinity. It was found that A1 and A2 are not necessary for direct binding. Thus, C25 mainly binds to the N-domain of CEACAM1, and for the binding with full affinity, B-domain is additionally required. In contrast, some of the C25-derived mutant clones bind to the N-domain of CEACAM1 with minimal or residual dependence on the B-domain for the binding with their full affinities as compared to C25 (FIG. 2).

Experimental Example 1.2. Evaluation of Binding Ability of Anti-CEACAM1 Antibody to CEACAM1 Protein Two micrograms of the recombinant CEACAM1 protein were dissolved in 1000 μl of PBS, which was dispensed into 96-well plate (Nunc; Cat. No. 467679) at 50 μl/well and incubated at 4° C. for 16 hours. Thereafter, 300 μl of 3% (v/v) bovine serum albumin was added to each well and incubated at 37° C. for 1 hour. C25 antibody (0.75 μg) was dissolved in 1000 μl of PBS. The diluted C25 solution was subjected to serial dilutions in PBS at a 1:1 volume ratio for 14 times. Each of the 15 different diluted C25 solutions was dispensed into each well at 50 μl/well, and incubated at 37° C. for 1 hour. Then, each well was washed 3 times with a washing buffer prepared by diluting 10 μl of Tween 20 (Sigma-Aldrich; Cat. No. P9146) in 990 μl of PBS. Thereafter, human IgG conjugated with 1 μl of HRP was diluted in 5000 μl of PBS, which was then dispensed into each well at 50 μl/well and incubated for 1 hour. The wells were washed three times with the washing buffer, and 50 μl of TMB solution was added to each well to induce color development, and then, 50 µl of 2 M $H_2SO_4$ was added to each well to stop the reaction. The absorbance was measured at a wavelength of 450 nm.

As a result, the $EC_{50}$ (Half maximal effective concentration) value was measured to be 0.35 nM (FIG. 3).

Also, 2.5 µg of the recombinant CEACAM-1/CD66a protein (R&D systems; Cat. No. 2244-CM) was dissolved in 10 ml of PBS, and dispensed into 96-well plate (Nunc; Cat. No. 467679) at 100 µl/well and incubated overnight at 4° C. Thereafter, 300 µl of 1% (v/v) bovine serum albumin was added to each well, which was incubated at 37° C. for 1 hour.

Each of C15, C16, C17, C18, C19, C20, C21, C22, C23, C25 and C26 antibodies (3 µg) was dissolved in 1000 µl of PBS. Each of the diluted antibodies was subjected to serial dilutions in PBS at a 1:1 volume ratio for 6 times. Each of the antibodies diluted to 7 concentrations was dispensed into each well at 100 µl/well, which was incubated at 37° C. for 1 hour. Then, each well was washed 3 times with a washing buffer prepared by diluting 10 µl of Tween 20 (Sigma-Aldrich; Cat. No. P9146) in 990 µl of PBS. Thereafter, 2 µl of human IgG conjugated with HRP was diluted in 10 ml of PBS, which was then dispensed into each well at 100 µl/well and incubated for 1 hour.

After completion of the reaction, the wells were washed three times with the washing buffer, and 100 µl of TMB solution was added to each well to induce color development. Then, 100 µl of 2 M $H_2SO_4$ was added to each well to stop the reaction, and the absorbance was measured at a wavelength of 450 nm.

As a result, it was found that C15, C16, C17, C18, C19, C20, C21, C22, C23, C25 and C26 antibody bind to CEACAM1 protein (FIG. 4).

Experimental Example 1.3. Evaluation of Binding Ability of Anti-CEACAM1 Antibodies to CEACAM1 Protein Expressed on Cell Surface Jurkat T cells (Jurkat E6.1 (ATCC; TIB-152TM)) were transfected with CEACAM1 cDNA, and treated with 700 µg/ml of G418 antibiotic for selection. The selected CEACAM1-Jurkat T cell lines were resuspended in the DPBS supplemented with 2% (v/v) FBS (hereinafter, referred to as FACS buffer), centrifuged at 1,500 rpm, and then resuspended in a FACS buffer such that the number of cells was $3\times10^6$/ml. The cells were dispensed into each well of a U-bottom 96-well plate at 100 µl/well. Then, the cells were centrifuged at 1,500 rpm, and the supernatant was discarded. After resuspending the recovered cells in 50 µl of the FACS buffer to which 0.5 µl of human Fc block (BD Pharmingen; Cat. No. 564220) solution was added, the cells were incubated at 4° C. for 15 minutes (FIG. 5).

Anti-CEACAM1 antibody or human IgG4 (Sigma; Cat. No. 14639) was diluted in 50 µl of the FACS buffer to obtain the concentrations of 20 µg/ml, 10 µg/ml, 5 µg/ml, 2.5 µg/ml, 1.25 µg/ml, 0.625 µg/ml, 0.3125 µg/ml and 0.15625 µg/ml. Fifty microliters of anti-CEACAM1 antibody or human IgG4 diluted above was added to the cells and incubated at 4° C. for 1.5 hour.

The cells incubated with antibodies were repeatedly subjected to the washing procedure of resuspending the cells in a FACS buffer and centrifuging the solution at 1,500 rpm. Goat anti-human $F(ab)_2$ labeled with phycoerythrin (hereinafter, referred to as PE) (Phycoerythrin-conjugated goat anti-human $F(ab)_2$; (Sigma; Cat. No. P8047)) was diluted in the FACS buffer at a volume ratio of 1:200, and then 100 µl of each solution was added to each well, which was incubated at 4° C. for 30 minutes in a dark condition. The cells were repeatedly subjected to the washing procedure of resuspending the cells in a FACS buffer, centrifuging the solution at 1,500 rpm, and discarding the supernatant. The cells were then resuspended in 100 µl of a fixation buffer (BD Cytofix™; Cat. No. 554655) and incubated at 4° C. for 30 minutes in a dark place.

The cells incubated with the fixation buffer were repeatedly subjected to the washing procedure of resuspending the cells in a FACS buffer, centrifuging the solution at 1,500 rpm, and discarding the supernatant. The washed cells were resuspended in 200 µl of a FACS buffer, and the mean fluorescence intensities (MFIs) of PE-labeled cells were compared in a FACS LSR-Fortessa. All FACS analyses were conducted using the FlowJo software.

It was observed that the maximal level of C25 binding to the target (MFI 1800 or more) was reached at 5 µg/ml of concentration, but its binding ability decreased rapidly below the concentration of 5 µg/ml (FIG. 5a).

The CEACAM1-Jurkat T cells prepared above were treated with Fc block solution and incubated for 15 minutes. Then, C25 and C25-derived clones including 4R9, 4R9_H2-2, 4R9_H4-n20 and 4R26 along with human IgG4 were diluted respectively in 50 µl of a FACS buffer to the concentrations of 25 µg/ml, 5 µg/ml, 1 µg/ml, 0.2 µg/ml, 0.04 µg/ml, 0.008 µg/ml, 0.0016 µg/ml and 0.00032 µg, and then dispensed into the cells, which were incubated at 4° C. for 1.5 hour. Herein, it is noted that the cell numbers were adjusted to $1\times10^5$. The cells incubated with the antibodies were repeatedly subjected to the washing procedure of resuspending the cells in a FACS buffer and centrifuging the solution at 1,500 rpm.

PE-conjugated goat anti-human $F(ab)_2$; (Sigma; Cat. No. P8047)) was diluted in the FACS buffer at a volume ratio of 1:200, and then added to the cells at 100 µl/well. Cells were resuspended well and incubated at 4° C. for 30 minutes in a dark condition.

The cells incubated with the fixation buffer were repeatedly subjected to the washing procedure of resuspending the cells in a FACS buffer, centrifuging the solution at 1,500 rpm, and discarding the supernatant. The washed cells were resuspended in 200 µl of a FACS buffer, and the mean fluorescence intensities (MFIs) of the PE-labeled cells were monitored by a FACS LSR-Fortessa. All FACS analyses were conducted using the FlowJo software.

Consistent with the results in FIG. 5a, C25 showed the maximal levels of its target-binding (MFI 8008 or more) at the concentration of 5 µg/ml, but the binding ability rapidly decreased below the concentration of 5 µg/ml. On the other hand, the target-binding abilities of C25-derived clones 4R9, 4R26, and 4R9_H2-2 were maintained up to 80% or higher of their maximal levels even at the concentration of 0.2 µg/ml. In addition, the MFI value of 4R9_H4-n20 clone reached up to 12,000 or more, showing 1.5 times higher in MFI values than those of other clones (12,000 vs 8,000), but, the binding ability decreased rapidly below the concentration of 5 µg/ml similar to that of C25 (FIG. 5b).

Experimental Example 1.4. Measurement of Target-Binding Affinity of Each Anti-CEACAM1 Antibody The quantitative binding abilities of C25, 4R9, 4R26, 4R9_H2-2, 4R9_H4-n20 and 4R9_H4-n20HC+4R26LC to CEACAM1 were measured using Octet QK$^e$ (Pall ForteBio). Antibodies isolated and purified in Example 1 at the concentration of 400 nM were serially 1:1 diluted for 6 times, and the resulting antibody solutions at the concentrations of 400 nM, 200 nM, 100 nM, 50 nM, 25 nM, 12.5 nM and 6.25 nM were dispensed into Greiner 96-well plate (Greiner; Cat. No. 655209) in a row. The last well in each row was with a sample at the antibody concentration of 0 nM. Recombinant human CEACAM1 protein (R&D Systems; Cat. No. 2244-CM) was diluted to obtain a concentration of 6.25 µg/µl, and dispensed into each well of another column at 200 µl/well.

As for the washing buffer, neutralization buffer and baseline buffer, Reagent/Kinetics buffer (10×) (Fortebio; Cat. No. 18-1092) were 1:10 diluted and dispensed into each well of a column in a row at 200 µl/well, and the regeneration buffer was dispensed into each well at 200 µl/well. Greiner 96-well plate was separately prepared, Reagent/Kinetics buffer (1×) was dispensed into each well of the number of biosensors to be used in a row at 200 µl/well, and Biosensors/Anti-His (His1K) (Fortebio; Cat. No. 18-5120) cassette was installed. Association and dissociation periods were set to 300 seconds and 600 seconds respectively, and $K_D$ values were measured.

As a result, their affinities to CEACAM1 were determined as affinity ($K_D$) values of 1.82 nM to 39.0 nM (FIG. 6).

Experimental Example 2. Evaluation of Physical Properties of Anti-CEACAM1 Antibody Experimental Example 2.1. Identification of Isoelectric Point of Anti-CEACAM1 Antibody Twenty milliliters of IEF anode buffer (50×) were mixed with 980 ml of deionized water (hereinafter, referred to as DW) to make a 1× IEF anode buffer, and 20 ml of IEF cathode buffer pH 3-10 (10×) was mixed with 180 ml of DW to make a 1× IEF cathode buffer. 1× IEF anode buffer and 1×IEF cathode buffer were cooled to 4° C. and used.

Using an IEF gel (Invitrogen/pH 3-10 IEF gel; 1.0 mm×10 well/EC6655BOX), the upper chamber was filled with 200 ml of 1× IEF cathode buffer and the lower chamber was filled with 600 ml of 1× IEF anode buffer. Fifteen microliters µl, out of 20 µl of the solution containing 10 µl of C25 at the concentration of 1.12 mg/ml mixed with 10 µl of IEF sample buffer (pH 3-10, 2×) were loaded, and 5 µl of IEF Markers 3-10 (SERVA/10 mg/mL/SERVA Liquid Mix; 39212.01) was used for a marker.

Electrophoresis was carried out with the voltage changed in three steps of 100V: 1 hour, 200V: 1 hour and 500V: 30 minutes, and fixation was carried out using 12% TCA solution for 30 minutes. After fixation, the isoelectric point was evaluated using Coomassie Blue R-250 Intron Biotechnology (IBS-BC006).

As a result, the actual isoelectric point value of C25 turned out 8.0, which was slightly higher than its theoretical value of 7.76 (FIG. 7).

Experimental Example 3. Measurement of Anti-CEACAM1 Antibody Effect on T Cell Activation Experimental Example 3.1. Evaluation of T Cell Activation by Anti-CEACAM1 Antibody Jurkat E6.1 (ATCC; TIB-152TM) cells were resuspended at $1 \times 10^5/200$ µl in complete Iscove's Modified Dulbecco's Medium (IMDM; Invitrogen; Cat. No. 12440053) supplemented with 10% (v/v) Fetal Bovine Serum (Gibco; Cat. No. 16000044) and 1× Penicillin/Streptomycin (100×; Gibco; Cat. No. 15140122), and incubated with plate-coated anti-CD3 (OKT3; 0.1 µg/ml; eBioscience; Cat. No. 16-0037), in the presence of 10 µg/ml or 25 µg/ml, at 37° C. for 96 hours with 5% $CO_2$. HuIgG4 was used as a control.

After 96 hours, the cells and culture medium were recovered and centrifuged at 1,500 rpm. While the supernatant was set aside for IL-2 measurement, the remaining cells were recovered, replaced with a FACS buffer, and subjected to a blocking step with Fc receptor at 4° C. for 15 minutes.

The cells were incubated with anti-CD25-PE-Cy7 antibody or anti-CD69-APC antibody (eBioscience; anti-CD25-PE-Cy7: Cat. No. 25-0259; anti-CD69-APC: Cat. No. 17-0699) at 4° C. for 15 minutes.

Cells were filled with a FACS buffer up to 200 µl, and centrifuged at 1,200 rpm for 5 minutes, with the supernatant removed. After resuspending the cells in a fresh FACS buffer, this procedure was repeated three times for complete removal of unbound antibodies. The cells were resuspended in DPBS supplemented with 1% (v/v) paraformaldehyde and fixed at 4° C. for 30 minutes.

Cells were resuspended in 1× FoxP3 staining buffer (eBioscience; Cat. No. 00-5523-00) and centrifuged. After repeating this procedure twice, anti-Ki67 antibody (eBioscience; Cat. No. 350520) labeled with a different dye was diluted at 1:100 volume ratio in 1× FoxP3 staining buffer, which was added to the cells to obtain the total volume of 50 µl, and then the mixture was incubated at 4° C. for 30 minutes. Cells were filled with 1× FoxP3 staining buffer and centrifuged. After repeated washing three times, cells were applied to flow cytometry for counting activated $CD25^+$ $CD69^+$ cells and further $Ki67^+$ proliferating populations in the FACS LSR-Fortessa device and analyzed using the FlowJo software (FIGS. 8 and 10).

As a result, when Jurkat T cells were treated with C25 at the antibody concentration of 10 µg/ml and 25 µg/ml in the CCM1 induction condition (OKT3: 0.1 µg/ml, culture in cIMDM for 4 days) for Jurkat E6.1 T cells, high levels of activation were observed. More specifically, the percentage and the number of activated $CD25^+$ $CD69^+$ populations of Jurkat T cells were increased two-fold or higher, and the percentage and the number of proliferating $Ki67^+$ cells were also increased two-fold or higher as compared to the control which was treated with huIgG4 (FIGS. 9b and 11b).

Experimental Example 3.2. Evaluation of IL-2 Secretion of T Cells by Anti-CEACAM1 Antibody To evaluate the changes in IL-2 secretion from T cells by anti-CEACAM1 antibody, anti-IL-2 antibodies (capture Ab: eBioscience; Cat. No. 14-7029-85) were diluted in a coating buffer (50 mM carbonate/bicarbonate buffer, pH 9.6) first. Then, the diluted anti-IL-2 antibody solution was dispensed into each well of a 96-well plate at 200 µl/well, and incubated at 4° C. for 16 to 18 hours. Then, the 96-well plate was washed with DPBS and 200 µl of a blocking buffer (SuperBlock™ Blocking Buffer: ThermoFisher Scientific; Cat. No. 37515) was added to each well, which was then incubated at room temperature for 30 minutes.

To obtain a standard curve, IL-2 recombinant protein (R&D Systems; Cat. No. P60568) was diluted in a blocking buffer to obtain a concentration of 20 µg/ml. The diluted IL-2 recombinant protein solution was serially diluted at a volume ratio of 1:1 for 11 times. Twelve IL-2 recombinant protein samples and the supernatants from the Jurkat E6.1 cell culture stored at −80° C. in Example 3.1 were dispensed into each well of a 96-well plate coated with anti-IL-2 antibody at 100 µl/well, and incubated at room temperature for 2 hours.

After washing the 96-well plate 4 times with a washing buffer prepared by diluting 10 µl of Tween 20 (Sigma-Aldrich; Cat. No. P9146) in 990 µl of PBS, a solution prepared by diluting biotin-conjugated anti-IL-2 antibodies (Detection antibody: eBioscience; Cat. No. 13-7028) in a blocking buffer at a volume ratio of 1:1,000 was dispensed into each well at 100 µl/well, which was then incubated at room temperature for 2 hours.

After washing the 96-well plate with a washing buffer 4 times, a solution prepared by diluting a peroxidase-labeled streptavidin (Sigma; Cat. No. 55512) in a blocking buffer at a volume ratio of 1:1,000 was dispensed into each well at 100 µl/well, which was incubated at room temperature for 2 hours.

After washing the 96-well plate 4 times again with a washing buffer, TMB peroxidase substrate solution (KPL; Cat. No. 52-00-02) was dispensed into each well at 100 µl/well, which was incubated for 10 minutes. Then, a stop solution (KPL; Cat. No. 50-85-05) was added to the wells at 100 µl/well, to stop the reaction. The O.D values were measured at a wavelength of 450 nm using a molecular dynamics reader device. The measured values were analyzed using SoftMax Pro 5.4.1.

As a result, when the cells were treated with C25 at the antibody concentration of 10 µg/ml and 25 µg/ml in the CEACAM1 induction condition (OKT3 at 0.1 µg/ml, culture for 4 days) for Jurkat E6.1, the secreted IL-2 levels measured using the supernatants were about three times higher than those of the control (FIGS. 9c and 11c).

Experimental Example 3.3. Evaluation of Activation of T Cells Overexpressing CEACAM1 by Anti-CEACAM-1 Antibody EF1 promoter-CEACAM1-GFP vector was transfected into Jurkat E6.1 T cells, and then treated with G418 disulfate salt solution (Sigma; G8168) at a concentration of 700 µg/ml, for selection. GFP$^+$ CEACAM1$^+$ cells were separated using Fluorescence-Activated Cell Sorter, to construct Jurkat cells overexpressing CEACAM1 (CEACAM1-Jurkat T cells).

CEACAM1-Jurkat T cells derived from Jurkat E6.1 (ATCC; TIB-152TM) cells were resuspended in 200 µl of IMDM supplemented with 10% FBS and 1× Penicillin/Streptomycin to obtain a cell number of $1 \times 10^5$, and then stimulated with plate-coated OKT3 (0.1 or 1 µg/ml; eBioscience; 16-0037), in the presence of 10 µg/ml or 25 µg/ml of C25, for 48 hours. HuIgG4 was used as a control.

After 48 hours, the cells and culture medium were recovered and centrifuged at 1,500 rpm. The supernatant was stored at −80° C. for IL-2 ELISA, and the remaining cells were recovered, replaced with a FACS buffer, and subjected to blocking of the Fc receptor at 4° C. for 15 minutes. Cells were treated with CD25-PE-Cy7 antibody or anti-CD69-APC antibody, and incubated at 4° C. for 15 minutes.

Cells were recovered, and filled with a FACS buffer up to 200 µl, and centrifuged at 1,200 rpm for 5 minutes. After resuspending the cells in a fresh FACS buffer, this procedure was repeated three times, for complete removal of unbound antibodies. The cells were resuspended in DPBS supplemented with 1% (v/v) paraformaldehyde and fixed at 4° C. for 30 minutes.

Cells were filled in 1× FoxP3 staining buffer up to 200 µl, and centrifuged at 1,200 rpm for 5 minutes, to remove the supernatant. After repeating this procedure twice, anti-Ki67 antibody labeled with a different dye was diluted at 1:100 volume ratio, which was added to the cells to obtain the total volume of 50 µl, and then the mixture was incubated at 4° C. for 30 minutes.

Cells were filled in 1× FoxP3 staining buffer up to 200 µl, and centrifuged at 1,200 rpm for 5 minutes, to remove the supernatant. After repeating this procedure three times, and replacing with FACS buffer finally, activated CD25$^+$ CD69$^+$ cells and proliferating Ki67$^+$ cells among them were identified in the FACS LSR-Fortessa device and analyzed using the FlowJo software (FIGS. 12 and 15).

As a result, CEACAM1-Jurkat T cells by a low concentration of OKT3 (0.1 µg/ml) in the presence of anti-CEACAM1 showed high levels of activation. More specifically, CD25$^+$ CD69$^+$ populations of CEACAM1-Jurkat T cells were increased by 1.5-fold (C25 at 25 µg/ml) or 4-fold or higher (C25 at 10 µg/ml) as compared to those of the huIgG4-treated group (FIGS. 13b and 14b).

Also, CEACAM1-Jurkat T cells by a high concentration of OKT3 (1 µg/ml) in the presence of anti-CEACAM1 showed high levels of activation. More specifically, CD25$^+$ CD69$^+$ populations of CEACAM1-Jurkat T cells were increased by 2-fold (C25 at 25 µg/ml) or by 6-fold or higher (C25 at 10 µg/ml) as compared to those of the huIgG4-treated group (FIGS. 16b and 17b).

Experimental Example 3.4. Evaluation of IL-2 Secretion of CEACAM1-Overexpressing T Cells by Anti-CEACAM1 Antibody To evaluate the anti-CEACAM1 antibody-induced changes in secreted IL-2 levels of CEACAM1-overexpressing T cells, the supernatant separated from CEACAM1-Jurkat E6.1 T cells stored at −80° C. in Experimental Example 3.3 was subjected to ELISA by the same method as in Experimental Example 3.2.

As a result, when the CEACAM1-Jurkat T cells overexpressing CEACAM1, were treated with C25 at the antibody concentrations of 10 µg/ml and 25 µg/ml in a culture condition (OKT3 at the concentration of 0.1 µg/ml, culture for 2 days), the IL-2 secretion levels were measured using the supernatants were 20 times or more higher than the control (FIGS. 13c and 14c).

Further, when the CEACAM1-Jurkat T cells overexpressing CEACAM1 were treated with C25 at the antibody concentrations of 10 µg/ml and 25 µg/ml in another culture condition (OKT3 at the concentration of 1 µg/ml, culture for 2 days), the IL-2 secretion levels were measured using the supernatants were 1.5 times or more higher than the control (FIGS. 16c and 17c).

Experimental Example 3.5. Evaluation of T Cell Activation by Anti-CEACAM1 Antibody Using NFAT-Luciferase Assay Jurkat-GFP/NFAT-luc cells (cells not expressing CEACAM1, NFAT-luciferase reporter-overexpressing cells) or Jurkat-CCM1/NFAT-luc cells (CEACAM1-overexpressing cells, NFAT-luciferase reporter-overexpressing cells) were resuspended in each well at a cell number of $6 \times 10^5$, and dispensed into 96-well plate coated with 0.05 or 0.1 µg/ml of OKT3, and added with each antibody at a concentration of 10 µg/ml prepared in Example 1 and anti-CD28 (28.2; eBioscience; Cat. No. 16-0289-85; at 1 µg/ml). Human IgG4 was used as a negative control.

After incubation for 6 hours, the cells were harvested, washed once with PBS, and lysed with 80 μl of a passive lysis buffer. Twenty microliters of the cell lysate were dispensed into each well of a white 96-well-assay plate, which was then placed in a luminometer device. A luciferase buffer was loaded in a luminometer injector, and 80 μl of the luciferase buffer was injected into each well, to measure the activity of luciferase.

As a result, the inhibitory effect by C25 on CCM1-dependent T cell inhibition was not observed in Jurkat-GFP/NFAT-luc which did not express CEACAM1 in a 6-hour culture condition, whereas enhancement levels of TCR-induced NFAT activation by C25 during 6-hour duration was 2 times or more higher in Jurkat-CCM1/NFAT-luc cells with the OKT3 at both the concentrations of 0.05 and 0.1 μg/ml (FIGS. 18 and 19).

Also, the experimental group treated with C25-derived anti-CEACAM1 antibodies showed 1.5 to 2 times higher NFAT-luc luciferase activities than that of the IgG4-treated group at 0.1 μg/ml of OKT3 concentration, which were statistically significant (FIG. 20).

Experimental Example 4. Evaluation of Expression of CEACAM1 in Human and Monkey Tissues A 10 mM solution of EZ-Link™ Sulo-NHS-LC-LC-Biotin (ThermoFisher Scientific; Cat. No. 21338) was prepared and 13.3 μl of the solution per 1 mg of C25 was added and biotinylated at 4° C. for 2 hours. Human and monkey TMA slides were deparaffinized in an oven at 60° C. for 1 hour. Hydration was progressively carried out in the order of xylene (100%), alcohol (90%), alcohol (80%) and alcohol (alcohol-DW).

For antigen retrieval, the TMA slides were treated in a constant temperature water bath containing 1.5 L of Tris-EDTA pH 9.0 buffer, which were incubated at 100° C. for 20 minutes. To prevent intracellular peroxidase activity, 100 μl of 3% hydrogen peroxide was added thereto and incubated for 6 minutes, and then 100 μl of 5% (v/v) normal horse serum was added thereto and incubated for 30 minutes.

The primary antibodies (biotin-conjugated hIgG4 or C25; 1 mg/ml) were diluted in 100 μl of a staining buffer at a 1:1 or 1:5 volume ratio, and incubated at room temperature for 2 hours. One hundred microliters of ABC reagent were added and incubated for 30 minutes. DAB substrate kit (VECTOR LABORATORIES; Cat. No. SK-4100) was added, followed by color development for 2 minutes and comparative staining with hematoxylin for analysis. Since CEACAM1 expression levels in normal cells were very low, the antibodies were used at relatively high concentrations.

The staining intensities of C25 on normal tissues of Cynomolgus monkeys were similar to those on human normal tissues, and the levels of CEACAM1 expression in normal tissues were very low. Therefore, CEACAM1 expression was detected only when the tissues were treated with high concentrations of C25 (FIG. 21). Human IgG4 was used at the same concentration, as a control for C25 (FIG. 22).

Experimental Example 5. Evaluation of Cross-Reactivity of Anti-CEACAM1 Antibody

Experimental Example 5.1. Evaluation of Cross-Reactivity of Anti-CEACAM1 Antibody to CEACAM Family Proteins Using Human IgG Fab Antibody All of the recombinant human CEACAM-1/CD66a protein (R&D systems; Cat. No. 2244-CM, HCCM1), recombinant human CEACAM-5/CD66e protein (R&D systems; Cat. No. 4128-CM, HCCM5), recombinant human CEACAM-6/CD66c protein (R&D systems; Cat. No. 3934-CM, HCCM6), recombinant human CEACAM-3/CD66d protein (Sino Biological; Cat. No. 11933-H08H, HCCM3), recombinant mouse PD-1 Fc chimeric protein (R&D systems; Cat. No. 1021-PD, mPD-1-Fc), recombinant CEACAM1-Fc (IgG4) protein (Mogam, in-house production, HCCM1-Fc), recombinant human CEACAM-1/CD66a protein Bulk (R&D systems; Cat. No. 2244-CM, HCCM1 (bulk)) and mouse CEACAM1/CD66a protein (Sino Biological; Cat. No. 50571-M08H, mouse CCM1) (2.5 μg each) were dissolved in 10 ml of PBS, respectively and dispensed into a 96-well plate (Nunc; Cat. No. 467679) at 100 μl/well, which was incubated overnight at 4° C. Thereafter, each well was treated with 300 μl of 1% (v/v) bovine serum albumin, which was incubated at 37° C. for 1 hour.

Three micrograms of C15, C16, C17, C18, C19, C20, C21, C22, C23, C25 and C26 antibodies were dissolved in 1000 μl of PBS, respectively. The diluted antibodies were dispensed into each well coated with each protein at 100 μl/well, which was incubated at 37° C. for 1 hour. Then, each well was washed 3 times with a washing buffer prepared by diluting 10 μl of Tween 20 (Sigma-Aldrich; Cat. No. P9146) in 990 μl of PBS. Thereafter, 2 μl of HRP-conjugated human anti-IgG-Fab antibody (anti-human IgG Fab; Sigma; Cat. No. A0293) was diluted in 10 ml of PBS, added to the wells at 100 μl/well, and incubated for 1 hour.

After completion of the reaction, the wells were washed three times with the washing buffer, and 100 μl of TMB solution was added to each well to induce color development. Then, 100 μl of 2 M $H_2SO_4$ was added to each well to stop the reaction, and the absorbance was measured at a wavelength of 450 nm.

As a result, all of the C15, C16, C17, C18, C19, C20, C21, C22, C23, C25 and C26 antibodies showed high levels of binding ability to HCCM1, HCCM1 (bulk) and HCCM1-Fc. The CEACAM1 antibodies excluding C17, C19, C22 showed basal levels of binding ability to HCCM3, HCCM5 and HCCM6 (FIG. 23). Thus, it was concluded that the anti-CEACAM antibodies of the present invention bind specifically to CEACAM1 only.

Experimental Example 5.2. Cross-Reactivity of CEACAM Family Protein with Anti-CEACAM1 Antibody Using Human IgG Fc Antibody All of the recombinant human CEACAM-1/CD66a protein (R&D systems; Cat No. 2244-CM, HCCM1), recombinant human CEACAM-5/CD66e protein (R&D systems; Cat. No. 4128-CM, HCCM5), recombinant human CEACAM-6/CD66c protein (R&D systems; Cat. No. 3934-CM, HCCM6), recombinant human CEACAM-3/CD66d protein (Sino Biological; Cat. No. 11933-H08H, HCCM3), human B7-H5/Gi24/VISTA protein (Sino Biological; Cat. No. 13482-H08H, HVISTA), recombinant human CEACAM-1/CD66a protein Bulk (R&D systems; Cat. No. 2244-CM, HCCM1 (bulk)), recombinant human CEACAM1-N domain-Kappa protein (Mogam, in-house production, HCCM1-N domain-kappa), and BSA protein (2.5 μg each) were dissolved in 10 ml of PBS, respectively, and dispensed into a 96-well plate at 100 μl/well, which was incubated at 4° C. overnight. Thereafter, each well was treated with 300 μl of 1% (v/v) bovine serum albumin, and incubated at 37° C. for 1 hour.

Each of C15, C16, C17, C18, C19, C20, C21, C22, C23, C25 and C26 antibodies (3 μg) was dissolved in 1000 μl of PBS. The diluted antibodies were dispensed into each well coated with each protein at 100 μl/well, and incubated at 37° C. for 1 hour. Then, each well was washed 3 times with a washing buffer prepared by diluting 10 μl of Tween 20 (Sigma-Aldrich; Cat. No. P9146) in 990 μl of PBS. Thereafter, 2 μl of HRP-conjugated human anti-IgG-Fc antibody (anti-human IgG Fc, Sigma Cat. No. A0170) was diluted in 10 ml of PBS, added to the wells at 100 μl/well, and incubated for 1 hour.

After completion of the reaction, the wells were washed three times with the washing buffer, and 100 μl of TMB solution was added to each well to induce color development. Then, 100 μl of 2 M $H_2SO_4$ was added to each well to stop the reaction, and the absorbance was measured at a wavelength of 450 nm.

As a result, all of the C15, C16, C17, C18, C19, C20, C21, C22, C23, C25 and C26 antibodies showed high levels of binding ability to HCCM1, HCCM1 (bulk) and HCCM1-N-domain-kappa, and the CEACAM1 antibodies excluding C17, C19, C22 showed basal levels of binding ability to HCCM3, HCCM5 and HCCM6 (FIG. 24).

Thus, it was found that the anti-CEACAM1 antibodies of the present invention bind specifically to CEACAM1 only.

Experimental Example 5.3. Evaluation of Cross-Reactivity of CEACAM Family Protein Expressed on Cell Surface with Anti-CEACAM1 Antibody HEK293 cells were added with 10 μg of each pEF1α-AcGFP-N1 vector (Clontech, Cat. No. 631973) as a control vector, CEACAM1, CEACAM3, CEACAM5, CEACAM6 and CEACAM8 plasmid vectors, followed by transfection under the condition of pulse voltage 1,100 V, pulse width 20 ms and pulse number 2. After 48 hours of transfection, GFP expression was confirmed by fluorescence microscopy. The cells were detached by treatment with 1 ml of TrypLE Express Solution (ThermoFisher Scientific; Cat. No. 12605010), resuspended in 9 ml of DMEM (Gibco, Cat. No. 11995-065) supplemented with 10% (v/v) FBS, and centrifuged at 1,200 rpm for 5 minutes, to remove the resulting supernatant.

After washing once with PBS, the cells were resuspended in a FACS buffer to obtain a concentration of $5\times10^5$ cells/100 μl. Human Fc Block solution was added to the samples at 1 μl/sample, which were incubated at 4° C. for 10 minutes. The cells were treated with huIgG4 or one of the anti-CEACAM1 clones listed at 1 μg/$5\times10^5$ cells, which were incubated at 4° C. for 10 minutes. After washing with FACS buffer, the PE-labeled goat-anti-huIgG4 antibodies were diluted at a ratio of 1:200 in a FACS buffer, and added to the samples at 100 μl/sample, which were incubated at 4° C. for 30 minutes. The samples were filled with a FACS buffer up to 200 μl, and then centrifuged at 1,200 rpm for 5 minutes, to remove the resulting supernatant. The fixation buffer (300 μl) was added to resuspend the cells. The cells expressing GFP were selected in the FACS LSR-Fortessa device, and the expression of CEACAM members were evaluated respectively using the antibody specific to each CEACAM member (Table 3). Also, the binding of anti-CEACAM1 antibodies was evaluated by PE fluorescence channel and analyzed using the FlowJo software.

TABLE 3

| Type | Form | Substance name | Purchased from: |
|---|---|---|---|
| CEACAM1 | cDNA clone | CEACAM1 | R&D Systems, RDC0951 |
| | Isotype | MouseIgG1 Isotype Control PE | R&D Systems, IC002P |
| | Anti-CEACAM1 antibody | Human CEACAM1/CD66a PEconjugated Antibody | R&D Systems, FAB2244P |
| CEACAM3 | cDNA clone | CEACAM3-GFP | Origene, RG217469 |
| | Isotype | Sheep IgG | R&D systems, 5-001-A |
| | Anti-CEACAM3 antibody | HUMAN CEACAM-3/CD66d Antibody | R&D systems, AF4166P |
| | Secondary antibody | Donkey Anti-Sheep IgG (H + L) Phycoerythrin | R&D Systems, F0126 |
| CEACAM5 | cDNA clone | CEACAM5-GFP | Origene, RG206434 |
| | Isotype | MouseIgG2a Isotype Control PE | R&D Systems, IC003P |
| | Anti-CEACAM5 antibody | HUMAN CEACAM-5/CD66e PE-conjugated Antibody | R&D systems, FAB41281P |
| CEACAM6 | cDNA clone | CEACAM6-GFP | Origene, RG202454 |
| | Isotype | Mouse IgG1 K Isotype Control PE | eBioscience, 12-4714-82 |
| | Anti-CEACAM6 antibody | Human CD66c-PE | eBioscience, 12-0667-42 |
| CEACAM8 | cDNA clone | CEACAM8 | Origene/RG204740 |
| | Isotype | MouseIgG1 Isotype Control PE | R&D Systems, IC002P |
| | Anti-CEACAM8 antibody | Human CEACAM8 PE-conjugated Antibody | R&D systems/FAB4246P |

As a result, it was found that C25 and C25-derived clones specifically bound to CEACAM1 only among the CEACAM members to which CEACAM1 belonged (FIG. 25).

Further, HEK293 cells were mixed with 10 μg of each control vector, Cynomolgus CEACAM1 plasmid vector and human CEACAM1 plasmid vector, followed by transfection using a Neon transfection system under the condition of pulse voltage 1,100 V, pulse width 20 ms and pulse number 2. After 48 hours of transfection, GFP expression was confirmed by a fluorescence microscope, and the cells were detached by treatment with TrypLE Express Solution, and transferred to the FACS buffer, to stop the reaction.

After washing once with PBS, the cells were resuspended in a FACS buffer to obtain a concentration of $5\times10^5$ cells/100 μl. Human Fc Block solution was added to the samples at 1 μl/sample, which were incubated at 4° C. for 10 minutes. The samples were treated with human IgG4 or C25 at a concentration of 1 μg/$5\times10^5$ cells, which were incubated at 4° C. for 1 hour. After washing with FACS buffer, the PE-labeled goat-anti-huIgG4 antibodies were diluted at a ratio of 1:200 in a FACS buffer, and added to the samples at 100 μl/sample, which were incubated at 4° C. for 30 minutes. The samples were filled with a FACS buffer up to 200 µl, and then centrifuged at 1,200 rpm for 5 minutes, to remove the resulting supernatant. The fixation buffer (300 µl) was added to resuspend the cells. The cells expressing GFP were selected in the FACS LSR-Fortessa device, and the expression of each of CEACAM members was evaluated using the antibody specific to each member of CEA family. Also, the binding with C25 was evaluated by PE fluorescence channel and analyzed using the FlowJo software.

As a result, it was found that C25 recognized not only human CEACAM1 but also monkey (Cynomolgus) CEACAM1 (FIG. 26a). C25-derived clones also recognized the CEACAM1 of cynomolgus as well as the human protein (FIG. 26b).

Experimental Example 6. Evaluation of Anti-Cancer Effect of Anti-CEACAM1 Antibody Cancer cells (MKN45: JCRB Cell Bank; Cat. No. JCRB0254; MKN1: JCRB Cell Bank; Cat. No. JCRB0252) were resuspended in RPMI 1640 medium (ThermoFisher Scientific; Cat. No. 11875093) at a concentration of $1 \times 10^4$/200 µl, and dispensed into each well of the 96-well plate at 200 µl/well, and cultured overnight under the condition of 37° C. and 5% $CO_2$. Unconjugated cells were removed along with the medium, and TALL-104 (ATCC; Cat. No. CRL-11386TM) or NK92MI (ATCC; Cat. No. CRL-2408TM) cells were added thereto at various ratios relative to cancer cells (0:1, 0.1:1:1:1, 10:1). Herein, C25 was also added to the wells at a concentration of 10 µg/ml. As a control, huIgG4 was treated in the same manner.

After co-culture for 6 hours, unconjugated soluble cells were removed along with the medium, and Cell Titer 96 Aqueous One Solution (Promega; Cat. No. G3582), an MTS assay reagent, was diluted at a ratio of 1:4 in RPMI 1640 medium. The diluted solution was added to the wells at 200 µl/well, and further cultured in a dark place for 3 hours. Thereafter, O.D value of each sample was measured with a spectrophotometer at a wavelength of 490 nm, and the measured values were analyzed using SoftMax Pro 5.4.1 program.

As a result, when the anti-cancer effects of CTL (FIG. 27: TALL-104) or NK (FIG. 28: NK-92MI) cells were evaluated by the method of evaluating the in vitro efficacy of C25, it was found that C25 increased the anti-cancer immune reactions of CTLs and natural killer cells in the case of MKN45 gastric cancer cell line in which CEACAM1 was expressed at a high level, whereas no anti-cancer effect of C25 was observed in the case of MKN1, a gastric cancer cell line, in which CEACAM1 expression was not detected (FIGS. 27 and 28).

In addition, when the in vitro effect of C25-derived anti-CEACAM1 antibody clones were tested in the CEACAM1+ MKN45 cancer cell line in the same manner as above, cancer cell death by anti-CEACAM1 antibodies reached 40 to 50% levels as compared to those of the control (FIG. 29).

The invention claimed is:

1. An anti-CEACAM1 antibody or an antigen-binding fragment thereof, comprising:
light chain CDR1 comprising the amino acid sequence of SEQ ID NO: 1;
light chain CDR2 comprising one of the amino acid sequences selected from the group consisting of SEQ ID NOS: 9 to 16;
light chain CDR3 comprising one of the amino acid sequences selected from the group consisting of SEQ ID NOS: 17 to 29;
heavy chain CDR1 comprising one of the amino acid sequences selected from the group consisting of SEQ ID NOS: 30 to 38;
heavy chain CDR2 comprising the amino acid sequence of SEQ ID NO: 39; and
heavy chain CDR3 comprising one of the amino acid sequences selected from the group consisting of SEQ ID NOS: 47 to 55.

2. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 9, light chain CDR3 comprising the amino acid sequence of SEQ ID NO: 17, heavy chain CDR1 comprising the amino acid sequence of SEQ ID NO: 30, heavy chain CDR2 comprising the amino acid sequence represented by SEQ ID NO: 39, and heavy chain CDR3 comprising the amino acid sequence of SEQ ID NO: 47.

3. The anti-CEACAM1 antibody or the antigen-binding fragment thereof of claim 2, wherein the antibody comprises a light chain variable domain comprising the amino acid sequence of SEQ ID NO: 56, and a heavy chain variable domain comprising the amino acid sequence of SEQ ID NO: 86.

4. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 9, light chain CDR3 comprising the amino acid sequence of SEQ ID NO: 18, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

5. The anti-CEACAM1 antibody or the antigen-binding fragment thereof of claim 4, wherein the antibody comprises a light chain variable domain comprising the amino acid sequence of SEQ ID NO: 58, and a heavy chain variable domain comprising the amino acid sequence of SEQ ID NO: 86.

6. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 9, light chain CDR3 comprising the amino acid sequence of SEQ ID NO: 19, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

7. The anti-CEACAM1 antibody or the antigen-binding fragment thereof of claim 6, wherein the antibody comprises a light chain variable domain comprising the amino acid sequence of SEQ ID NO: 60, and a heavy chain variable domain comprising the amino acid sequence of SEQ ID NO: 86.

8. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 9, light chain CDR3 comprising the amino acid sequence of SEQ ID NO: 20, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

9. The anti-CEACAM1 antibody or the antigen-binding fragment thereof of claim 8, wherein the antibody comprises a light chain variable domain comprising the amino acid sequence of SEQ ID NO: 62, and a heavy chain variable domain comprising the amino acid sequence of SEQ ID NO: 86.

10. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 10, light chain CDR3 comprising the amino acid sequence of SEQ ID NO: 17, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

11. The anti-CEACAM1 antibody or the antigen-binding fragment thereof of claim 10, wherein the antibody comprises a light chain variable domain comprising the amino acid sequence of SEQ ID NO: 64, and a heavy chain variable domain comprising the amino acid sequence of SEQ ID NO: 86.

12. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 10, light chain CDR3 comprising the amino acid sequence of SEQ ID NO: 21, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

13. The anti-CEACAM1 antibody or the antigen-binding fragment thereof of claim 12, wherein the antibody comprises a light chain variable domain comprising the amino acid sequence of SEQ ID NO: 66, and a heavy chain variable domain comprising the amino acid sequence of SEQ ID NO: 86.

14. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 11, light chain CDR3 comprising the amino acid sequence of SEQ ID NO: 22, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

15. The anti-CEACAM1 antibody or the antigen-binding fragment thereof of claim 14, wherein the antibody comprises a light chain variable domain comprising the amino acid sequence of SEQ ID NO: 68, and a heavy chain variable domain comprising the amino acid sequence of SEQ ID NO: 86.

16. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 10, light chain CDR3 comprising the amino acid sequence of SEQ ID NO: 17, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 48.

17. The anti-CEACAM1 antibody or the antigen-binding fragment thereof of claim 16, wherein the antibody comprises a light chain variable domain comprising the amino acid sequence of SEQ ID NO: 64, and a heavy chain variable domain comprising the amino acid sequence of SEQ ID NO: 88.

18. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 10, light chain CDR3 comprising the amino acid sequence of SEQ ID NO: 17, heavy chain CDR1 comprising the amino acid sequence of SEQ ID NO: 31, heavy chain CDR2 comprising the amino acid sequence of SEQ ID NO: 39, and heavy chain CDR3 comprising the amino acid sequence of SEQ ID NO: 47.

19. The anti-CEACAM1 antibody or the antigen-binding fragment thereof of claim 18, wherein the antibody comprises a light chain variable domain comprising the amino acid sequence of SEQ ID NO: 64, and a heavy chain variable domain comprising the amino acid sequence of SEQ ID NO: 90.

20. The anti-CEACAM1 antibody or the antigen-binding fragment thereof of claim 1, wherein the antibody comprises light chain CDR1 comprising the amino acid sequence of SEQ ID NO: 1, light chain CDR2 comprising the amino acid sequence of SEQ ID NO: 9, light chain CDR3 comprising the amino acid sequence of SEQ ID NO: 23, heavy chain CDR1 comprising the amino acid sequence of SEQ ID NO: 30, heavy chain CDR2 comprising the amino acid sequence of SEQ ID NO: 39, and heavy chain CDR3 comprising the amino acid sequence of SEQ ID NO: 47.

21. The anti-CEACAM1 antibody or the antigen-binding fragment thereof of claim 20, wherein the antibody comprises a light chain variable domain comprising the amino acid sequence of SEQ ID NO: 70, and a heavy chain variable domain comprising the amino acid sequence of SEQ ID NO: 86.

22. The anti-CEACAM1 antibody or the antigen-binding fragment thereof according to claim 1, wherein the antigen-binding fragment is one selected from the group consisting of Fab, scFv, F(ab)$^2$ and Fv.

23. An anti-cancer agent comprising the anti-CEACAM1 antibody or the antigen-binding fragment thereof according to claim 1 as an active ingredient.

24. The anti-cancer agent of claim 23, wherein the cancer is one selected from the group consisting of gastric cancer, pancreatic cancer, melanoma, lung cancer, thyroid cancer and myeloma.

25. An anti-cancer adjuvant comprising the anti-CEACAM1 antibody or the antigen-binding fragment thereof according to claim 1 as an active ingredient.

26. A composition comprising the anti-cancer adjuvant of claim 25 and a cell therapeutic agent.

27. The composition of claim 26, wherein the cell therapeutic agent is cytotoxic T cells or natural killer cells.

28. A method for treating cancer comprising administering to a subject in need thereof (i) the anti-CEACAM1 antibody or the antigen-binding fragment thereof according to claim 1; and/or (ii) lymphocytes contacted with the anti-CEACAM1 antibody or the antigen-binding fragment thereof according to claim 1.

29. The method for treating cancer of claim 28, wherein the lymphocytes comprise at least one of cytotoxic T cells and natural killer cells.

30. The method for treating cancer of claim 28, wherein the lymphocytes are obtained from the subject.

31. The method for treating cancer of claim 28, wherein the cancer is selected from the group consisting of gastric cancer, pancreatic cancer, melanoma, lung cancer, thyroid cancer, and myeloma.

32. A method for inhibiting proliferation of CEACAM1-expressing tumor cells, comprising contacting the CEACAM1-expressing tumor cells with the anti-CEACAM1 antibody or the antigen-binding fragment thereof of claim 1.

* * * * *

SEQUENCE LISTING

```
<160> NUMBER OF SEQ ID NOS: 130

<210> SEQ ID NO 1
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR1 (VL)

<400> SEQUENCE: 1

Ser Ser Asn Ile Gly Asn Asn Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Amino acid seqeunce for anti-CEACAM1 antibody
      of  CDR1 (VL)

<400> SEQUENCE: 2

Ser Ser Ser Asn Ile Gly Asn Asn Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR1 (VL)

<400> SEQUENCE: 3

Ser Ser Asn Ile Gly Ser Asn Thr
```

<210> SEQ ID NO 4
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VL)

<400> SEQUENCE: 4

Ser Ser Asn Ile Gly Asn Asn Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VL)

<400> SEQUENCE: 5

Ser Ser Asn Ile Gly Ser Asn Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VL)

<400> SEQUENCE: 6

Ser Ser Asn Ile Gly Ser Asn Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VL)

<400> SEQUENCE: 7

Ser Ser Asn Ile Gly Ser Asn Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VL)

<400> SEQUENCE: 8

Ser Ser Asn Ile Gly Asn Asn
1               5

<210> SEQ ID NO 9
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody of CDR2 (VL)

<400> SEQUENCE: 9

Ala Asp Ser Lys Arg Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VL)

<400> SEQUENCE: 10

Ala Asp Ser Arg Arg Pro
1               5

<210> SEQ ID NO 11
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VL)

<400> SEQUENCE: 11

Ala Asp Ser Lys Arg Leu
1               5

<210> SEQ ID NO 12
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VL)

<400> SEQUENCE: 12

Ala Asn Ser Asn Arg Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VL)

<400> SEQUENCE: 13

Ala Asp Asn Asn Arg Pro
1               5

<210> SEQ ID NO 14
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VL)

<400> SEQUENCE: 14

Ala Asn Ser His Arg Pro
1               5

<210> SEQ ID NO 15

```
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of  CDR2 (VL)

<400> SEQUENCE: 15

Ala Asn Ser His Arg Pro
1               5

<210> SEQ ID NO 16
<211> LENGTH: 6
<212> TYPE: PRT
<213> ORGANISM: Artificial Sequence
<220> FEATURE:
<223> OTHER INFORMATION: Amino acid seqeunce for anti-CEACAM1 antibody
      of  CDR2 (VL)

<400> SEQUENCE: 16

Ser Asn Ser His Arg Pro
1               5

<210> SEQ ID NO 17
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 17

Gly Ala Trp Asp Leu Ser Leu Asn Gly Tyr Val
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 18

Gly Ala Trp Asp Val Ser His Asn Gly Tyr Val
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 19

Gly Ala Trp Asp Gln Ser Leu Asn Gly Tyr Val
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 20
```

```
Gly Ala Trp Asp Ser Met Gly Asn Gly Tyr Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 21

Gly Ala Trp Asp Ala Ser Tyr Asn Gly Tyr Val
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 22

Gly Ala Trp Asp Gly Arg Leu Asn Gly Tyr Val
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 23

Gly Ala Trp Asp Ala Ser Leu Asn Gly Tyr Val
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 24

Gly Thr Trp Asp Ala Ser Leu Ser Ala Tyr Val
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 25

Gly Thr Trp Asp Tyr Ser Leu Ser Gly Tyr Val
1               5                   10

<210> SEQ ID NO 26
<211> LENGTH: 11
<212> TYPE: PRT
<213> ORGANISM: Artificial Sequence
<220> FEATURE:
```

```
<223> OTHER INFORMATION: Amino acid seqeunce for anti-CEACAM1 antibody
      of  CDR3 (VL)

<400> SEQUENCE: 26

Gly Ser Trp Asp Asp Ser Leu Asn Ala Tyr Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 27

Ala Ala Trp Asp Ser Ser Leu Asn Gly Tyr Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 28

Gly Ser Trp Asp Ser Ser Leu Asn Ala Tyr Val
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VL)

<400> SEQUENCE: 29

Gly Ala Trp Asp Tyr Ser Leu Ser Gly Tyr Val
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR1 (VH)

<400> SEQUENCE: 30

Gly Phe Thr Phe Ser Asn Tyr Ala
1               5

<210> SEQ ID NO 31
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR1 (VH)

<400> SEQUENCE: 31

Gly Phe Asn Phe Ser Asn Tyr Ala
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VH)

<400> SEQUENCE: 32

Gly Phe Thr Phe Ser Ser Tyr Ser
1               5

<210> SEQ ID NO 33
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VH)

<400> SEQUENCE: 33

Gly Phe Thr Phe Ser Asn Tyr Ser
1               5

<210> SEQ ID NO 34
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VH)

<400> SEQUENCE: 34

Gly Phe Thr Phe Ser Asp Tyr Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VH)

<400> SEQUENCE: 35

Gly Phe Thr Phe Ser Asn Tyr Asp
1               5

<210> SEQ ID NO 36
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VH)

<400> SEQUENCE: 36

Gly Phe Thr Phe Ser Gly Tyr Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR1 (VH)

<400> SEQUENCE: 37
```

```
Gly Phe Thr Phe Ser Asp Tyr Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR1 (VH)

<400> SEQUENCE: 38

Gly Phe Thr Phe Ser Gly Tyr Asp
1               5

<210> SEQ ID NO 39
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR2 (VH)

<400> SEQUENCE: 39

Ile Ser His Gly Gly Gly Ser Ile
1               5

<210> SEQ ID NO 40
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR2 (VH)

<400> SEQUENCE: 40

Ile Ser Pro Asn Gly Gly Asn Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR2 (VH)

<400> SEQUENCE: 41

Ile Ser Ser Asp Gly Gly Ser Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of  CDR2 (VH)

<400> SEQUENCE: 42

Ile Tyr Pro Asp Asp Gly Asn Thr
1               5

<210> SEQ ID NO 43
<211> LENGTH: 8
<212> TYPE: PRT
<213> ORGANISM: Artificial Sequence
```

```
<220> FEATURE:
<223> OTHER INFORMATION: Amino acid seqeunce for anti-CEACAM1 antibody
      of CDR2 (VH)

<400> SEQUENCE: 43

Ile Ser His Ser Ser Gly Ser Lys
1               5

<210> SEQ ID NO 44
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VH)

<400> SEQUENCE: 44

Ile Tyr His Asp Gly Gly Ser Thr
1               5

<210> SEQ ID NO 45
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VH)

<400> SEQUENCE: 45

Ile Tyr Ser Gly Ser Ser Ser Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Amino acid seqeunce for anti-CEACAM1 antibody
      of CDR2 (VH)

<400> SEQUENCE: 46

Ile Ser Tyr Gly Gly Gly Ser Ile
1               5

<210> SEQ ID NO 47
<211> LENGTH: 14
<212> TYPE: PRT
<213> ORGANISM: Artificial Sequence
<220> FEATURE:
<223> OTHER INFORMATION: Amino acid seqeunce for anti-CEACAM1 antibody
      of CDR3 (VH)

<400> SEQUENCE: 47

Ala Arg Asp Pro Thr Lys Gly Tyr Ala Pro Thr Phe Asp Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Amino acid seqeunce for anti-CEACAM1 antibody
      of CDR3 (VH)

<400> SEQUENCE: 48

Ala Arg Asp Pro Thr Lys Gly Tyr Ala Pro Leu Phe Asp Tyr
1               5                   10
```

```
<210> SEQ ID NO 49
<211> LENGTH: 14
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 49

Ala Lys Asp Pro Tyr Asn Ile Tyr Gln Pro Leu Phe Asp Tyr
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 50

Ala Arg Asp Pro Arg Lys His Val Asp Arg Tyr Phe Asp Tyr
1               5                   10

<210> SEQ ID NO 51
<211> LENGTH: 20
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 51

Ala Arg Gly Ser Ile Trp Trp Leu Ser Leu Ile Pro Ser Ser Tyr Asn
1               5                   10                  15

Ala Met Asp Val
            20

<210> SEQ ID NO 52
<211> LENGTH: 20
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 52

Ala Arg Asp Pro Leu Pro Cys Leu Ile Pro Lys Cys Ser Tyr Tyr Tyr
1               5                   10                  15

Ala Met Asp Val
            20

<210> SEQ ID NO 53
<211> LENGTH: 20
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 53

Ala Arg Val Thr Val Leu Cys Thr Thr Tyr Gly Cys Ser Ser Tyr Asp
1               5                   10                  15

Gly Met Asp Val
            20
```

```
<210> SEQ ID NO 54
<211> LENGTH: 20
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 54

Ala Lys Ala Pro Leu Pro Phe Tyr Phe Arg Pro Lys Ser Tyr Tyr Tyr
1               5                   10                  15

Ala Met Asp Val
            20

<210> SEQ ID NO 55
<211> LENGTH: 20
<212> TYPE: PRT
<213> ORGANISM: Artificial Sequence
<220> FEATURE:
<223> OTHER INFORMATION: Amino acid seqeunce for anti-CEACAM1 antibody
      of  CDR3 (VH)

<400> SEQUENCE: 55

Ala Lys Asp Arg Leu Pro Gln Lys Ala Val Arg His Ser Tyr Ala Asn
1               5                   10                  15

Gly Met Asp Val
            20

<210> SEQ ID NO 56
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Leu Ser Leu
                85                  90                  95

Asn Gly Tyr Val Phe Gly Gly Gly Thr Lys Leu Thr Val Leu Gly
            100                 105                 110

<210> SEQ ID NO 57
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of  variable region (VL)

<400> SEQUENCE: 57
cagtctgtgc tgactcagcc accctcagcg tctgggaccc ccgggcagag ggtcaccatc    60
```

```
tcttgtagtg gctcttcatc caatattggc aataattatg tctcctggta ccagcagctc    120
ccaggaacgg cccccaaact cctcatctat gctgatagta agcggccaag cggggtccct    180
gaccgattct ctggctccaa gtctggcacc tcagcctccc tggccatcag tgggctccgg    240
tccgaggatg aggctgatta ttactgtggt gcttgggatt tgagcctgaa tggttatgtc    300
ttcggcggag gcaccaagct gaccgtccta ggt                                 333
```

<210> SEQ ID NO 58
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 58

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Val Ser His
                85                  90                  95

Asn Gly Tyr Val Phe Gly Gly Gly Thr Lys Leu Thr Val Leu Gly
            100                 105                 110
```

<210> SEQ ID NO 59
<211> LENGTH: 333
<212> TYPE: DNA
<213> ORGANISM: Artificial Sequence
<220> FEATURE:
<223> OTHER INFORMATION: Nucleotide seqeunce  for anti-CEACAM1 antibody
      of  variable region (VL)

<400> SEQUENCE: 59

```
cagtctgtgc tgactcagcc accctcagcg tctgggaccc ccgggcagag ggtcaccatc     60
tcttgtagtg gctcttcatc caatattggc aataattatg tctcctggta ccagcagctc    120
ccaggaacgg cccccaaact cctcatctat gctgatagta agcggccaag cggggtccct    180
gaccgattct ctggctccaa gtctggcacc tcagcctccc tggccatcag tgggctccgg    240
tccgaggatg aggctgatta ttactgtggt gcttgggatg ttagccataa tggttatgtc    300
ttcggcggag gcaccaagct gaccgtccta ggt                                 333
```

<210> SEQ ID NO 60
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 60

```
Gln Ser Val Leu Thr Gln Pro Pro Ser Ala Ser Gly Thr Pro Gly Gln
1               5                   10                  15
```

```
Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Gln Ser Leu
                85                  90                  95

Asn Gly Tyr Val Phe Gly Gly Gly Thr Lys Leu Thr Val Leu Gly
            100                 105                 110
```

<210> SEQ ID NO 61
<211> LENGTH: 333
<212> TYPE: DNA
<213> ORGANISM: Artificial Sequence
<220> FEATURE:
<223> OTHER INFORMATION: Nucleotide seqeunce  for anti-CEACAM1 antibody
      of  variable region (VL)

<400> SEQUENCE: 61

```
cagtctgtgc tgactcagcc accctcagcg tctgggaccc ccgggcagag ggtcaccatc      60
tcttgtagtg ctcttcatc caatattggc aataattatg tctcctggta ccagcagctc     120
ccaggaacgg cccccaaact cctcatctat gctgatagta agcggccaag cggggtccct    180
gaccgattct ctggctccaa gtctggcacc tcagcctccc tggccatcag tgggctccgg    240
tccgaggatg aggctgatta ttactgtggt gcttgggatc agagcctgaa tggttatgtc    300
ttcggcggag gcaccaagct gaccgtccta ggt                                 333
```

<210> SEQ ID NO 62
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 62

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Met Gly
                85                  90                  95

Asn Gly Tyr Val Phe Gly Gly Gly Thr Lys Leu Thr Val Leu Gly
            100                 105                 110
```

<210> SEQ ID NO 63
<211> LENGTH: 333
<212> TYPE: DNA
<213> ORGANISM: Artificial Sequence
<220> FEATURE:

<223> OTHER INFORMATION: Nucleotide seqeunce for anti-CEACAM1 antibody
of variable region (VL)

<400> SEQUENCE: 63
cagtctgtgc tgactcagcc accctcagcg tctgggaccc ccgggcagag ggtcaccatc    60
tcttgtagtg gctcttcatc caatattggc aataattatg tctcctggta ccagcagctc   120
ccaggaacgg cccccaaact cctcatctat gctgatagta agcggccaag cggggtccct   180
gaccgattct ctggctccaa gtctggcacc tcagcctccc tggccatcag tgggctccgg   240
tccgaggatg aggctgatta ttactgtggt gcttgggatt cgatgggtaa tggttatgtc   300
ttcggcggag gcaccaagct gaccgtccta ggt                                333

<210> SEQ ID NO 64
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
of variable region (VL)

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Arg Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Leu Ser Leu
                85                  90                  95

Asn Gly Tyr Val Phe Gly Gly Gly Thr Lys Leu Thr Val Leu Gly
            100                 105                 110

<210> SEQ ID NO 65
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
of variable region (VL)

<400> SEQUENCE: 65
cagtctgtgc tgactcagcc accctcagcg tctgggaccc ccgggcagag ggtcaccatc    60
tcttgtagtg gctcttcatc caatattggc aataattatg tctcctggta ccagcagctc   120
ccaggaacgg cccccaaact cctcatctat gctgatagta ggcggccaag cggggtccct   180
gaccgattct ctggctccaa gtctggcacc tcagcctccc tggccatcag tgggctccgg   240
tccgaggatg aggctgatta ttactgtggt gcttgggatc tgagcctgaa tggttatgtc   300
ttcggcggag gcaccaagct gaccgtccta ggt                                333

<210> SEQ ID NO 66
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody of variable region (VL)

<400> SEQUENCE: 66

Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Ala Asp Ser Arg Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gly Ala Trp Asp Ala Ser Tyr
                85                  90                  95
Asn Gly Tyr Val Phe Gly Gly Gly Thr Lys Leu Thr Val Leu Gly
            100                 105                 110

<210> SEQ ID NO 67
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of variable region (VL)

<400> SEQUENCE: 67
cagtctgtgc tgactcagcc accctcagcg tctgggaccc ccgggcagag ggtcaccatc      60
tcttgtagtg gctcttcatc caatattggc aataattatg tctcctggta ccagcagctc     120
ccaggaacgg cccccaaact cctcatctat gctgatagta ggcggccaag cggggtccct     180
gaccgattct ctggctccaa gtctggcacc tcagcctccc tggccattag tgggctccgg     240
tccgaggatg aggctgatta ttactgtggt gcttgggatg ctagctataa tggttatgtc     300
ttcggcggag gcaccaagct gaccgtccta ggt                                  333

<210> SEQ ID NO 68
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of variable region (VL)

<400> SEQUENCE: 68

Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Ala Asp Ser Lys Arg Leu Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gly Ala Trp Asp Gly Arg Leu
                85                  90                  95
Asn Gly Tyr Val Phe Gly Gly Gly Thr Lys Leu Thr Val Leu Gly
            100                 105                 110

<210> SEQ ID NO 69
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of  variable region (VL)

<400> SEQUENCE: 69

```
cagtctgtgc tgactcagcc accctcagcg tctgggaccc ccgggcagag ggtcaccatc    60
tcttgtagtg gctcttcatc caatattggc aataattatg tctcctggta ccagcagctc   120
ccaggaacgg cccccaaact cctcatctat gctgatagta agcggctaag cggggtccct   180
gaccgattct ctggctccaa gtctggcacc tcagcctccc tggccatcag tgggctccgg   240
tccgaggatg aggctgatta ttactgtggt gcttgggatg tcgtctgaa tggttatgtc    300 ttcggcggag gcaccaagct gaccgtccta ggt                                333
```

<210> SEQ ID NO 70
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 70

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ala Ser Leu
                85                  90                  95

Asn Gly Tyr Val Phe Gly Gly Gly Thr Lys Leu Thr Val Leu Gly
            100                 105                 110
```

<210> SEQ ID NO 71
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of  variable region (VL)

<400> SEQUENCE: 71

```
cagtctgtgc tgactcagcc accctcagcg tctgggaccc ccgggcagag ggtcaccatc    60
tcttgtagtg gctcttcatc caatattggc aataattatg tctcctggta ccagcagctc   120
ccaggaacgg cccccaaact cctcatctat gctgatagta agcggccaag cggggtccct   180
gaccgattct ctggctccaa gtctggcacc tcagcctccc tggccatcag tgggctccgg   240
tccgaggatg aggctgatta ttactgtggt gcttgggatg ctagcctgaa tggttatgtc   300
ttcggcggag gcaccaagct gaccgtccta ggt                                333
```

<210> SEQ ID NO 72
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 72

Gln Ser Val Leu Thr Gln Pro Leu Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Asn Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Glu Glu Ala Asp Tyr Tyr Cys Gly Thr Trp Asp Ala Ser Leu
                85                  90                  95

Ser Ala Tyr Val Phe Gly Gly Gly Thr Lys Leu Thr Val Leu Gly
            100                 105                 110

<210> SEQ ID NO 73
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of  variable region (VL)

<400> SEQUENCE: 73
cagtctgtgc tgactcagcc actctcagcg tctgggaccc ccgggcagag ggtcaccatc      60
tcttgtagtg gctcttcatc taatattggc aataattatg tcaactggta ccagcagctc     120
ccaggaacgg ccccccaaact cctcatctat gctaatagta atcggccaag cggggtccct    180
gaccgattct ctggctccaa gtctggcacc tcagcctccc tggccatcag tgggctccgg     240
tccgaggagg aggctgatta ttactgtggt acttgggatg ctagcctgag tgcttatgtc     300
ttcggcggag gcaccaagct gaccgtccta ggt                                  333

<210> SEQ ID NO 74
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 74

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln Gln Leu Pro Gly Thr Ala Pro Lys Leu Leu
        35                  40                  45

Ile Tyr Ala Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Gly Thr Trp Asp Tyr Ser Leu
                    85                  90                  95

Ser Gly Tyr Val Leu Gly Gly Gly Thr Lys Leu Thr Val Leu Gly
                100                 105                 110
```

<210> SEQ ID NO 75
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of  variable region (VL)

<400> SEQUENCE: 75

```
cagtctgtgc tgactcagcc accctcagcg tctgggaccc ccgggcagag ggtcaccatc        60
tcttgtagtg gctcttcatc taatattggc agtaatactg tctcctggta ccagcagctc       120
ccaggaacgg cccccaaact cctcatctat gctgataata atcggccaag cggggtccct       180
gaccgattct ctggctccaa gtctggcacc tcagcctccc tggccatcag tgggctccgg       240
tccgaggatg aggctgatta ttactgtggt acttgggatt atagcctgag tggttatgtc       300
ttaggcggag gcaccaagct gaccgtccta ggt                                    333
```

<210> SEQ ID NO 76
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of  variable region (VL)

<400> SEQUENCE: 76

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Ala Asn Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ala Ser Leu
                    85                  90                  95

Asn Gly Tyr Val Phe Gly Gly Gly Thr Lys Leu Thr Val Leu Gly
                100                 105                 110
```

<210> SEQ ID NO 77
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of  variable region (VL)

<400> SEQUENCE: 77

```
cagtctgtgc tgactcagcc accctcagcg tctgggaccc ccgggcagag ggtcaccatc        60
tcttgtagtg gctcttcatc taatattggc aataatgctg tcaactggta ccagcagctc       120
ccaggaacgg cccccaaact cctcatctat gctaatagtc atcggccaag cggggtccct       180
```

```
gaccgattct ctggctccaa gtctggcacc tcagcctccc tggccatcag tgggctccgg        240
tccgaggatg aggctgatta ttactgtggt gcttgggatg ctagcctgaa tggttatgtc        300
ttcggcggag gcaccaagct gaccgtccta ggt                                    333
```

```
<210> SEQ ID NO 78
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of variable region (VL)

<400> SEQUENCE: 78
```

```
Gln Ser Val Leu Thr Gln Pro Pro Ser Ala Pro Gly Thr Pro Gly Gln
1               5                   10                  15

Arg Val Thr Ile Ser Cys Ser Gly Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Asp Ser Leu
                85                  90                  95

Asn Ala Tyr Val Phe Gly Gly Gly Thr Lys Leu Thr Val Leu Gly
            100                 105                 110
```

```
<210> SEQ ID NO 79
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of variable region (VL)

<400> SEQUENCE: 79
```

```
cagtctgtgc tgactcagcc accctcagcg cctgggaccc ccgggcagag ggtcaccatc        60
tcttgtagtg gctcttcatc taatattggc agtaatgctg tcacctgcta ccagcagctc       120
ccaggaacgg cccccaaact cctcatctat gctgatagtc atcggccaag cggggtccct       180
gaccgattct ctggctccaa gtctggcacc tcagcctccc tggccatcag tgggctccgg       240
tccgaggatg aggctgatta ttactgtggt tcttgggatg atagcctgaa tgcttatgtc       300
ttcggcggag gcaccaagct gaccgtccta ggt                                    333
```

```
<210> SEQ ID NO 80
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of variable region (VL)

<400> SEQUENCE: 80
```

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30
```

```
Tyr Val Asn Trp Tyr Gln Gln Leu Pro Gly Thr Ala Pro Lys Leu Leu
             35                  40                  45

Ile Tyr Ser Asn Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Ser Ser Leu
                 85                  90                  95

Asn Gly Tyr Val Phe Gly Gly Gly Thr Lys Leu Thr Val Leu Gly
                100                 105                 110

<210> SEQ ID NO 81
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of variable region (VL)

<400> SEQUENCE: 81
cagtctgtgc tgactcagcc accctcagcg tctgggaccc ccgggcagag ggtcaccatc    60
tcttgtactg gctcttcatc taatattggc agtaattatg tcaactggta ccagcagctc   120
ccaggaacgg cccccaaact cctcatctat tctaatagtc atcggccaag cggggtccct   180
gaccgattct ctggctccaa gtctggcacc tcagcctccc tggccatcag tgggctccgg   240
tccgaggatg aggctgatta ttactgtgct gcttgggatt ctagcctgaa tggttatgtc   300
ttcggcggag gcaccaagct gaccgtccta ggt                                333

<210> SEQ ID NO 82
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
      of variable region (VL)

<400> SEQUENCE: 82

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Asn Val Thr Trp Tyr Gln Gln Leu Pro Gly Thr Ala Pro Lys Leu Leu
             35                  40                  45

Ile Tyr Ala Asn Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ser Ser Leu
                 85                  90                  95

Asn Ala Tyr Val Phe Gly Gly Gly Thr Lys Leu Thr Val Leu Gly
                100                 105                 110

<210> SEQ ID NO 83
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
      of variable region (VL)
```

<400> SEQUENCE: 83

```
cagtctgtgc tgactcagcc accctcagcg tctgggaccc ccgggcagag ggtcaccatc    60
tcttgtagtg gctcttcatc taatattggc agtaataatg tcacctggta ccagcagctc   120
ccaggaacgg ccccaaaact cctcatctat gctaatagtc atcggccaag cggggtccct   180
gaccgattct ctggctccaa gtctggcacc tcagcctccc tggccatcag tgggctccgg   240
tccgaggatg aggctgatta ttactgtggt tcttgggatt ctagcctgaa tgcttatgtc   300
ttcggcggag gcaccaagct gaccgtccta ggt                                333
```

<210> SEQ ID NO 84
<211> LENGTH: 111
<212> TYPE: PRT
<213> ORGANISM: Artificial Sequence
<220> FEATURE:
<223> OTHER INFORMATION: Amino acid seqeunce for anti-CEACAM1 antibody
     of variable region (VL)

<400> SEQUENCE: 84

```
Gln Ser Val Leu Thr Gln Pro Pro Ser Ala Ser Gly Thr Pro Gly Gln
1               5                  10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Ser Gly Tyr Val Phe Gly Gly Gly Thr Lys Leu Thr Val Leu Gly
            100                 105                 110
```

<210> SEQ ID NO 85
<211> LENGTH: 333
<212> TYPE: DNA
<213> ORGANISM: Artificial Sequence
<220> FEATURE:
<223> OTHER INFORMATION: Nucleotide seqeunce for anti-CEACAM1 antibody
     of variable region (VL)

<400> SEQUENCE: 85

```
cagtctgtgc tgactcagcc accctcagcg tctgggaccc ccgggcagag ggtcaccatc    60
tcttgtagtg gctcttcatc taatattggc aataattatg tcacctggta ccagcagctc   120
ccaggaacgg ccccaaaact cctcatctat gctgatagtc atcggccaag cggggtccct   180
gaccgattct ctggctccaa gtctggcacc tcagcctccc tggccatcag tgggctccgg   240
tccgaggacg aggctgatta ttactgtggt gcttgggatt atagcctgag tggttatgtc   300
ttcggcggag gcaccaagct gaccgtccta ggt                                333
```

<210> SEQ ID NO 86
<211> LENGTH: 121
<212> TYPE: PRT
<213> ORGANISM: Artificial Sequence
<220> FEATURE:
<223> OTHER INFORMATION: Amino acid seqeunce for anti-CEACAM1 antibody
     of variable region (VH)

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Gly Ser Ile Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Lys Gly Tyr Ala Pro Thr Phe Asp Tyr Trp Gly
            100                 105                 110

Gln Gly Thr Leu Val Thr Val Ser Ser
            115                 120

<210> SEQ ID NO 87
<211> LENGTH: 363
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 87
gaggtgcagc tgttggagtc tgggggaggc ttggtacagc ctggggggtc cctgagactc      60
tcctgtgcag cctctggatt cacctttagc aattatgcta tgagctgggt ccgccaggct    120
ccagggaagg gctggagtg gtctcagtg atctctcatg gtggtggtag tatatattac      180
gctgattctg taaaaggtcg gctcaccatc tccagagaca attccaagaa cacgctgtat    240
ctgcaaatga acagcctgag agccgaggac acggccgtgt attactgtgc gagagatcct    300
actaaggggt atgctcctac tttcgactac tggggccagg gtacactggt caccgtgagc    360
tca                                                                  363

<210> SEQ ID NO 88
<211> LENGTH: 121
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Gly Ser Ile Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Lys Gly Tyr Ala Pro Leu Phe Asp Tyr Trp Gly
            100                 105                 110

Gln Gly Thr Leu Val Thr Val Ser Ser
        115                 120

<210> SEQ ID NO 89
<211> LENGTH: 363
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 89
gaggtgcagc tgttggagtc tggggagggc ttggtacagc ctggggggtc cctgagactc      60
tcctgtgcag cctctggatt cacctttagc aattatgcta tgagctgggt ccgccaggct     120
ccagggaagg gctggagtg gtctcagtg atctctcatg gtggtggtag tatatattac       180
gctgattctg taaaaggtcg gctcaccatc tccagagaca attccaagaa cacgctgtat     240
ctgcaaatga acagcctgag agccgaggac acggccgtgt attactgtgc gagagatcct    300
actaaggggt atgctccttt gttcgactac tggggccagg gtacactggt caccgtgagc    360
tca                                                                  363

<210> SEQ ID NO 90
<211> LENGTH: 121
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Gly Ser Ile Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Lys Gly Tyr Ala Pro Thr Phe Asp Tyr Trp Gly
            100                 105                 110

Gln Gly Thr Leu Val Thr Val Ser Ser
        115                 120

<210> SEQ ID NO 91
<211> LENGTH: 363
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 91
gaggtgcagc tgttggagtc tggggagggc ttggtacagc ctggggggtc cctgagactc      60

```
tcctgtgcag cctctggatt caactttagc aattatgcta tgagctgggt ccgccaggct    120
ccagggaagg ggctggagtg ggtctcagtg atctctcatg gtggtggtag tatatattac    180
gctgattctg taaaaggtcg gctcaccatc tccagagaca attccaagaa cacgctgtat    240
ctgcaaatga acagcctgag agccgaggac acggccgtgt attactgtgc gagagatcct    300
actaaggggt atgctcctac tttcgattac tggggccagg gtacactggt caccgtgagc    360
tca                                                                  363
```

<210> SEQ ID NO 92
<211> LENGTH: 121
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 92

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Pro Asn Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Val Tyr Tyr Cys
                85                  90                  95

Ala Lys Asp Pro Tyr Asn Ile Tyr Gln Pro Leu Phe Asp Tyr Trp Gly
            100                 105                 110

Gln Gly Thr Leu Val Thr Val Ser Ser
        115                 120
```

<210> SEQ ID NO 93
<211> LENGTH: 362
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 93

```
gaggtgcagc tgttggagtc tgggggaggc ttggtacagc ctggggggtc cctgagactc    60
tcctgtgcag ctctggattc acctttagca gttattctat gagctgggtc cgccaggctc    120
cagggaaggg gctggagtgg gtctcatcga tctctcctaa tggtggtaat aaatattacg    180
ctgattctgt aaaaggtcgg ttcaccatct ccagagacaa ttccaagaac acgctgtatc    240
tgcaaatgaa cagcctggga gccgaggaca cggccgtgta ttactgtgcg aaagatcctt    300
ataatattta tcagcctttg ttcgactact ggggcaggg tacactggtc accgtgagct    360
ca                                                                  362
```

<210> SEQ ID NO 94
<211> LENGTH: 121
<212> TYPE: PRT
<213> ORGANISM: Artificial Sequence
<220> FEATURE:
<223> OTHER INFORMATION: Amino acid seqeunce for anti-CEACAM1 antibody of variable region (VH)

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ala Ile Ser Ser Asp Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Lys His Val Arg Tyr Phe Asp Tyr Trp Gly
            100                 105                 110

Gln Gly Thr Leu Val Thr Val Ser Ser
        115                 120

<210> SEQ ID NO 95
<211> LENGTH: 363
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 95
gaggtgcagc tgttggagtc tgggggaggc ttggtacagc ctggggggtc cctgagactc    60
tcctgtgcag cctctggatt cacctttagc aattattcta tgagctgggt ccgccaggct   120
ccagggaagg gctggagtg gtctcagcg atctcttctg atggtggtag taaatattac    180
gctgattctg taaaaggtcg gttcaccatc tccagagaca attccaagaa cacgctgtat   240
ctgcaaatga acagcctgag agccgaggac acggccgtgt attactgtgc gagagatcct   300
cgtaagcatg tggatcgtta tttcgactac tggggccagg gtacactggt caccgtgagc   360
tca                                                                 363

<210> SEQ ID NO 96
<211> LENGTH: 127
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Gly Ser Ile Trp Trp Leu Ser Leu Ile Pro Ser Ser Tyr Asn
            100                 105                 110

Ala Met Asp Val Trp Gly Gln Gly Thr Leu Val Ala Val Ser Ser
        115                 120                 125

<210> SEQ ID NO 97
<211> LENGTH: 381
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 97
gaggtgcagc tgttggagtc tgggggaggc ttggtacagc ctggggggtc cctgagactc      60
tcctgtgcag cctctggatt cacctttagc gattattcta tgagctgggt ccgccaggct     120
ccagggaagg ggctggagtg ggtctcagtg atctatcctg atgatggtaa tacatattac     180
gctgattctg taaaaggtcg gttcaccatc tccagagaca attccaagaa cacgctgtat     240
ctgcaaatga acagcctgag agccgaggac acggccgtgt attactgtgc gagaggtagt     300
atttggtggc tgtctttgat tccttcttct tataatgcta tggacgtctg gggccagggt     360
acactggtca ccgtgagctc a                                                381

<210> SEQ ID NO 98
<211> LENGTH: 127
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Gly Ile Ser His Ser Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Asp Pro Leu Pro Cys Leu Ile Pro Lys Cys Ser Tyr Tyr Tyr
            100                 105                 110

Ala Met Asp Val Trp Gly Gln Gly Thr Leu Val Thr Val Ser Ser
        115                 120                 125

<210> SEQ ID NO 99
<211> LENGTH: 381
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 99

```
gaggtgcagc tgttggagtc tgggggaggc ttggtacagc ctgggggtc cctgagactc        60 tcctgtgcag cctctggatt caccttttagc aattatgata tgagctgggt ccgccaggct      120
ccagggaagg ggctggagtg ggtctcaggg atctctcata gtagtggtag taaatattac      180
gctgattctg taaaaggtcg gttcaccatc tccagagaca attccaagaa cacgctgtat      240
ctgcaaatga acagcctgag agccgaggac acggccgtgt attactgtgc gagagatcct      300
cttccgtgtc ttattcctaa gtgttcttat tattatgcta tggacgtctg gggccagggt      360
acactggtca ccgtgagctc a                                                 381
```

<210> SEQ ID NO 100
<211> LENGTH: 127
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 100

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Gly Ile Tyr His Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Val Leu Cys Thr Thr Tyr Gly Cys Ser Ser Tyr Asp
            100                 105                 110

Gly Met Asp Val Trp Gly Gln Gly Thr Leu Val Thr Val Ser Ser
        115                 120                 125
```

<210> SEQ ID NO 101
<211> LENGTH: 381
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 101

```
gaggtgcagc tgttggagtc tgggggaggc ttggtacagc ctgggggtc cctgagactc        60 tcctgtgcag cctctggatt caccttttagc ggttatgcta tgagctgggt ccgccaggct      120
ccagggaagg ggctggagtg ggtctcaggg atctatcatg atggtggtag tacatattac      180
gctgattctg taaaaggtcg gttcaccatc tccagagaca attccaagaa cacgctgtat      240
ctgcaaatga acagcctgag agccgaggac acggccgtgt attactgtgc gagagttact      300
gttctgtgta cgacgtatgg ttgttcttct tatgatggta tggacgtctg gggccagggt      360
acactggtca ccgtgagctc a                                                 381
```

<210> SEQ ID NO 102
<211> LENGTH: 127
<212> TYPE: PRT

<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Met Ile Tyr Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Leu Pro Phe Tyr Phe Arg Pro Lys Ser Tyr Tyr Tyr
            100                 105                 110

Ala Met Asp Val Trp Gly Gln Gly Thr Leu Val Thr Val Ser Ser
        115                 120                 125

<210> SEQ ID NO 103
<211> LENGTH: 381
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 103
gaggtgcagc tgttggagtc cggggggaggc ttggtacagc ctggggggtc cctgagactc      60
tcctgtgcag cctctggatt cacctttagc gattatgata tgagctgggt ccgccaggct     120
ccagggaagg ggctggagtg ggtctcaatg atctattctg gtagtagtag taaatattac     180
gctgattctg taaaaggtcg gttcaccatc tccagagaca attccaagaa cacgctgtat     240
ctgcaaatga acagcctgag agccgaggac acggccgtgt attactgtgc gaaagctcct     300
cttccgtttt attttcggcc taagtcttat tattatgcta tggacgtctg gggccagggt     360
acactggtca ccgtgagctc a                                                381

<210> SEQ ID NO 104
<211> LENGTH: 127
<212> TYPE: PRT
<213> ORGANISM: Artificial Sequence
<220> FEATURE:
<223> OTHER INFORMATION: Amino acid seqeunce for anti-CEACAM1 antibody
      of variable region (VH)

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Trp Ile Ser Tyr Gly Gly Gly Ser Ile Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Pro Gln Lys Ala Val Arg His Ser Tyr Ala Asn
            100                 105                 110

Gly Met Asp Val Trp Gly Gln Gly Thr Leu Val Thr Val Ser Ser
            115                 120                 125
```

<210> SEQ ID NO 105
<211> LENGTH: 381
<212> TYPE: DNA
<213> ORGANISM: Artificial Sequence
<220> FEATURE:
<223> OTHER INFORMATION: Nucleotide seqeunce for anti-CEACAM1 antibody
      of variable region (VH)

<400> SEQUENCE: 105

```
gaggtgcagc tgttggagtc tggggggaggc ttggtacagc ctgggggtc cctgagactc      60 tcctgtgcag cctctggatt caccttagc ggttatgata tgagctgggt ccgccaggct     120
ccagggaagg gctggagtg gtctcatgg atctcttatg gtggtggtag tatatattac      180
gctgattctg taaaaggtcg gttcaccatc tccagagaca attccaagaa cacgctgtat     240
ctgcaaatga acagcctgag agccgaggac acggccgtgt attactgtgc gaaagatcgt     300
cttcctcaga aggctgtgcg gcattcttat gctaatggta tggacgtctg gggccagggt     360
acactggtca ccgtgagctc a                                                381
```

<210> SEQ ID NO 106
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 106

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Ala Asp Ser Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Leu Ser Leu
                 85                  90                  95

Asn Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
```

```
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 107
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of  light chain

<400> SEQUENCE: 107

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Val Ser His
                85                  90                  95

Asn Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 108
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of  light chain

<400> SEQUENCE: 108

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
```

```
            20                  25                  30
Tyr Val Ser Trp Tyr Gln Gln Leu Pro Gly Thr Ala Pro Lys Leu Leu
        35                  40                  45
Ile Tyr Ala Asp Ser Lys Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gly Ala Trp Asp Gln Ser Leu
                85                  90                  95
Asn Gly Tyr Val Phe Gly Gly Gly Thr Lys Leu Thr Val Leu Gly Gln
            100                 105                 110
Pro Lys Ala Asn Pro Thr Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys
    210                 215

<210> SEQ ID NO 109
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 109

Gln Ser Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Ala Asp Ser Lys Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Gly Ala Trp Asp Ser Met Gly
                85                  90                  95
Asn Gly Tyr Val Phe Gly Gly Gly Thr Lys Leu Thr Val Leu Gly Gln
            100                 105                 110
Pro Lys Ala Asn Pro Thr Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Gly Ser Pro Val Lys
145                 150                 155                 160
```

Ala Gly Val Glu Thr Thr Lys Pro Ser Lys Gln Ser Asn Asn Lys Tyr
         165                 170                 175

Ala Ala Ser Ser Tyr Leu Ser Leu Thr Pro Glu Gln Trp Lys Ser His
         180                 185                 190

Arg Ser Tyr Ser Cys Gln Val Thr His Glu Gly Ser Thr Val Glu Lys
         195                 200                 205

Thr Val Ala Pro Thr Glu Cys
         210                 215

<210> SEQ ID NO 110
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 110

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Ala Asp Ser Arg Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Leu Ser Leu
                85                  90                  95

Asn Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 111
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 111

Gln Ser Val Leu Thr Gln Pro Pro Ser Ala Ser Gly Thr Pro Gly Gln
1               5                   10                  15

```
Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Arg Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ala Ser Tyr
                85                  90                  95

Asn Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 112
<211> LENGTH: 216
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Ala Asp Ser Lys Arg Leu Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Gly Arg Leu
                85                  90                  95

Asn Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160
```

Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Arg Ser His
            180                 185                 190

Arg Ser Tyr Ser Cys Gln Val Thr His Glu Gly Glu His Arg Gly Lys
            195                 200                 205

Arg Gln Trp Pro Pro Thr Glu Cys
            210                 215

<210> SEQ ID NO 113
<211> LENGTH: 216
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 113

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ala Ser Leu
            85                  90                  95

Asn Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
            165                 170                 175

Ala Ala Ser Ser Tyr Leu Ser Leu Thr Pro Glu Gln Trp Arg Ser His
            180                 185                 190

Arg Ser Tyr Ser Cys Gln Val Thr His Glu Gly Glu His Arg Gly Lys
            195                 200                 205

Arg Gln Trp Pro Pro Thr Glu Cys
            210                 215

<210> SEQ ID NO 114
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of light chain

<400> SEQUENCE: 114

Gln Ser Val Leu Thr Gln Pro Leu Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Asn Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Glu Glu Ala Asp Tyr Tyr Cys Gly Thr Trp Asp Ala Ser Leu
                85                  90                  95

Ser Ala Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 115
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of  light chain

<400> SEQUENCE: 115

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Tyr Gln Gln Leu Pro Gly Thr Ala Pro Lys Leu Leu
        35                  40                  45

Ile Tyr Ala Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Asp Ser Leu
                85                  90                  95

Ser Gly Tyr Val Leu Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys

```
                145                 150                 155                 160
Ala Gly Val Glu Thr Thr Lys Pro Ser Lys Gln Ser Asn Asn Lys Tyr
                    165                 170                 175

Ala Ala Ser Ser Tyr Leu Ser Leu Thr Pro Glu Gln Trp Lys Ser His
                    180                 185                 190

Arg Ser Tyr Ser Cys Gln Val Thr His Glu Gly Ser Thr Val Glu Lys
                    195                 200                 205

Thr Val Ala Pro Thr Glu Cys
                    210                 215

<210> SEQ ID NO 116
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of  light chain

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ala Ser Leu
                85                  90                  95

Asn Gly Tyr Val Phe Gly Gly Gly Thr Lys Leu Thr Val Leu Gly Gln
                    100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                    165                 170                 175

Ala Ala Ser Ser Tyr Leu Ser Leu Thr Pro Glu Gln Trp Lys Ser His
                    180                 185                 190

Arg Ser Tyr Ser Cys Gln Val Thr His Glu Gly Ser Thr Val Glu Lys
                    195                 200                 205

Thr Val Ala Pro Thr Glu Cys
                    210                 215

<210> SEQ ID NO 117
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody
      of  light chain

<400> SEQUENCE: 117

Gln Ser Val Leu Thr Gln Pro Pro Ser Ala Pro Gly Thr Pro Gly Gln
```

```
                1               5                  10                 15
            Arg Val Thr Ile Ser Cys Ser Gly Ser Ser Asn Ile Gly Ser Asn
                            20                 25                 30

Ala Val Thr Trp Tyr Gln Gln Leu Pro Gly Thr Ala Pro Lys Leu Leu
                            35                 40                 45

Ile Tyr Ala Asp Ser His Arg Pro Ser Gly Val Pro Asp Arg Phe Ser
                        50                 55                 60

Gly Ser Lys Ser Gly Thr Ser Ala Ser Leu Ala Ile Ser Gly Leu Arg
             65                 70                 75                 80

Ser Glu Asp Glu Ala Asp Tyr Tyr Cys Gly Ser Trp Asp Ser Ser Leu
                                85                 90                 95

Asn Ala Tyr Val Phe Gly Gly Gly Thr Lys Leu Thr Val Leu Gly Gln
                           100                105                110

Pro Lys Ala Asn Pro Thr Val Thr Leu Phe Pro Pro Ser Ser Glu Glu
                           115                120                125

Leu Gln Ala Asn Lys Ala Thr Leu Val Cys Leu Ile Ser Asp Phe Tyr
                           130                135                140

Pro Gly Ala Val Thr Val Ala Trp Lys Ala Asp Gly Ser Pro Val Lys
            145                150                155                160

Ala Gly Val Glu Thr Thr Lys Pro Ser Lys Gln Ser Asn Asn Lys Tyr
                               165                170                175

Ala Ala Ser Ser Tyr Leu Ser Leu Thr Pro Glu Gln Trp Lys Ser His
                           180                185                190

Arg Ser Tyr Ser Cys Gln Val Thr His Glu Gly Ser Thr Val Glu Lys
                           195                200                205

Thr Val Ala Pro Thr Glu Cys
                           210                215

<210> SEQ ID NO 118
            <211> LENGTH: 215
            <212> TYPE: PRT
            <213> ORGANISM: Artificial Sequence
            <220> FEATURE:
            <223> OTHER INFORMATION: Amino acid seqeunce for anti-CEACAM1 antibody
                  of  light chain

<400> SEQUENCE: 118

Gln Ser Val Leu Thr Gln Pro Pro Ser Ala Ser Gly Thr Pro Gly Gln
             1               5                  10                 15

Arg Val Thr Ile Ser Cys Thr Gly Ser Ser Asn Ile Gly Ser Asn
                            20                 25                 30

Tyr Val Asn Trp Tyr Gln Gln Leu Pro Gly Thr Ala Pro Lys Leu Leu
                            35                 40                 45

Ile Tyr Ser Asn Ser His Arg Pro Ser Gly Val Pro Asp Arg Phe Ser
                        50                 55                 60

Gly Ser Lys Ser Gly Thr Ser Ala Ser Leu Ala Ile Ser Gly Leu Arg
             65                 70                 75                 80

Ser Glu Asp Glu Ala Asp Tyr Tyr Cys Ala Ala Trp Asp Ser Ser Leu
                                85                 90                 95

Asn Gly Tyr Val Phe Gly Gly Gly Thr Lys Leu Thr Val Leu Gly Gln
                           100                105                110

Pro Lys Ala Asn Pro Thr Val Thr Leu Phe Pro Pro Ser Ser Glu Glu
                           115                120                125

Leu Gln Ala Asn Lys Ala Thr Leu Val Cys Leu Ile Ser Asp Phe Tyr
                           130                135                140
```

```
Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215
```

<210> SEQ ID NO 119
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody of light chain

<400> SEQUENCE: 119

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Asn Val Thr Trp Tyr Gln Gln Leu Pro Gly Thr Ala Pro Lys Leu Leu
                35                  40                  45

Ile Tyr Ala Asn Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ser Ser Leu
                85                  90                  95

Asn Ala Tyr Val Phe Gly Gly Gly Thr Lys Leu Thr Val Leu Gly Gln
                100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215
```

<210> SEQ ID NO 120
<211> LENGTH: 215
<212> TYPE: PRT
<213> ORGANISM: Artificial Sequence
<220> FEATURE:
<223> OTHER INFORMATION: Amino acid seqeunce for anti-CEACAM1 antibody of light chain

<400> SEQUENCE: 120

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys
    210                 215

<210> SEQ ID NO 121
<211> LENGTH: 448
<212> TYPE: PRT
<213> ORGANISM: Artificial Sequence
<220> FEATURE:
<223> OTHER INFORMATION: Amino acid seqeunce for anti-CEACAM1 antibody
      of  heavy chain

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Val Ile Ser His Gly Gly Gly Ser Ile Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Lys Gly Tyr Ala Pro Thr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Gly Lys
        435                 440                 445

<210> SEQ ID NO 122
<211> LENGTH: 448
<212> TYPE: PRT
<213> ORGANISM: Artificial Sequence
<220> FEATURE:
<223> OTHER INFORMATION: Amino acid seqeunce for anti-CEACAM1 antibody
      of heavy chain

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Gly Ser Ile Tyr Tyr Ala Asp Ser Val
```

```
            50                  55                  60
Lys Gly Arg Leu Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Thr Lys Gly Tyr Ala Pro Leu Phe Asp Tyr Trp Gly
            100                 105                 110

Gln Gly Thr Leu Val Thr Val Ser Ser Ala Ser Thr Lys Gly Pro Ser
             115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
             195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
             275                 280                 285

Lys Thr Lys Pro Arg Glu Glu Gln Phe Asn Ser Thr Tyr Arg Val Val
             290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
             355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
             435                 440                 445

<210> SEQ ID NO 123
<211> LENGTH: 448
<212> TYPE: PRT
<213> ORGANISM: Artificial Sequence
```

<220> FEATURE:
<223> OTHER INFORMATION: Amino acid seqeunce for anti-CEACAM1 antibody of heavy chain

<400> SEQUENCE: 123

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Ser Asn Tyr
            20                  25                  30

Ala Met Ser Trp Val Arg Gln Ala Pro Gly Lys Gly Leu Glu Trp Val
        35                  40                  45

Ser Val Ile Ser His Gly Gly Ser Ile Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Thr Lys Gly Tyr Ala Pro Thr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
                385                 390                 395                 400
Ser Asp Gly Ser Phe Phe Leu Tyr Ser Arg Leu Thr Val Asp Lys Ser
                    405                 410                 415

Arg Trp Gln Glu Gly Asn Val Phe Ser Cys Ser Val Met His Glu Ala
                    420                 425                 430

Leu His Asn His Tyr Thr Gln Lys Ser Leu Ser Leu Ser Leu Gly Lys
                    435                 440                 445

<210> SEQ ID NO 124
<211> LENGTH: 448
<212> TYPE: PRT
<213> ORGANISM: Artificial Sequence
<220> FEATURE:
<223> OTHER INFORMATION: Amino acid seqeunce for anti-CEACAM1 antibody
      of heavy chain

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Ser Trp Val Arg Gln Ala Pro Gly Lys Gly Leu Glu Trp Val
                35                  40                  45

Ser Ser Ile Ser Pro Asn Gly Gly Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Val Tyr Tyr Cys
                85                  90                  95

Ala Lys Asp Pro Tyr Asn Ile Tyr Gln Pro Leu Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300
```

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 125
<211> LENGTH: 448
<212> TYPE: PRT
<213> ORGANISM: Artificial Sequence
<220> FEATURE:
<223> OTHER INFORMATION: Amino acid seqeunce for anti-CEACAM1 antibody
      of heavy chain

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Ser Trp Val Arg Gln Ala Pro Gly Lys Gly Leu Glu Trp Val
        35                  40                  45

Ser Ala Ile Ser Ser Asp Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Lys His Val Asp Arg Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
    435                 440                 445

<210> SEQ ID NO 126
<211> LENGTH: 454
<212> TYPE: PRT
<213> ORGANISM: Artificial Sequence
<220> FEATURE:
<223> OTHER INFORMATION: Amino acid seqeunce for anti-CEACAM1 antibody
      of heavy chain

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Ser Ile Trp Trp Leu Ser Leu Ile Pro Ser Ser Tyr Asn
        100                 105                 110

Ala Met Asp Val Trp Gly Gln Gly Thr Leu Val Ala Val Ser Ser Ala
    115                 120                 125

Ser Thr Lys Gly Pro Ser Val Phe Pro Leu Ala Pro Cys Ser Arg Ser

```
            130                 135                 140
Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 127
<211> LENGTH: 454
<212> TYPE: PRT
<213> ORGANISM: Artificial Sequence
<220> FEATURE:
<223> OTHER INFORMATION: Amino acid seqeunce for anti-CEACAM1 antibody
      of  heavy chain

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Asp Met Ser Trp Val Arg Gln Ala Pro Gly Lys Gly Leu Glu Trp Val
         35                  40                  45

Ser Gly Ile Ser His Ser Gly Ser Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Pro Leu Pro Cys Leu Ile Pro Lys Cys Ser Tyr Tyr Tyr
            100                 105                 110

Ala Met Asp Val Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Lys Thr Tyr
    195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
    275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Leu Gly Lys
```

450

<210> SEQ ID NO 128
<211> LENGTH: 454
<212> TYPE: PRT
<213> ORGANISM: Artificial Sequence
<220> FEATURE:
<223> OTHER INFORMATION: Amino acid seqeunce for anti-CEACAM1 antibody
    of heavy chain

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Gly Ile Tyr His Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Val Leu Cys Thr Thr Tyr Gly Cys Ser Ser Tyr Asp
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Lys Thr Tyr
        195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

```
Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 129
<211> LENGTH: 454
<212> TYPE: PRT
<213> ORGANISM: Artificial Sequence
<220> FEATURE:
<223> OTHER INFORMATION: Amino acid seqeunce for anti-CEACAM1 antibody
      of heavy chain

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Met Ile Tyr Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Leu Pro Phe Tyr Phe Arg Pro Lys Ser Tyr Tyr Tyr
            100                 105                 110

Ala Met Asp Val Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 130
<211> LENGTH: 454
<212> TYPE: PRT
<213> ORGANISM: Artificial Sequence
<220> FEATURE:
<223> OTHER INFORMATION: Amino acid seqeunce for anti-CEACAM1 antibody
      of  heavy chain

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Trp Ile Ser Tyr Gly Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Pro Gln Lys Ala Val Arg His Ser Tyr Ala Asn
            100                 105                 110

Gly Met Asp Val Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
```

-continued

```
145                 150                 155                 160
Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
        210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
            435                 440                 445

Ser Leu Ser Leu Gly Lys
    450
```